(12) United States Patent
Andreini et al.

(10) Patent No.: US 9,242,943 B2
(45) Date of Patent: Jan. 26, 2016

(54) 1,4 OXAZINES AS BACE1 AND/OR BACE2 INHIBITORS

(75) Inventors: Matteo Andreini, Siena (IT); Emanuele Gabellieri, Siena (IT); Wolfgang Guba, Muellheim (DE); Hans Hilpert, Muenchenstein (CH); Alexander V. Mayweg, Shanghai (CN); Robert Narquizian, Zaessingue (FR); Eoin Power, Blackrock (IE); Massimiliano Travagli, Siena (IT); Thomas Woltering, Freiburg (DE); Wolfgang Wostl, Grenzach-Wyhlen (DE); Harald Mauser, Riehen (CH)

(73) Assignees: SIENA BIOTECH S.P.A., Siena (IT); HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 13/348,675

(22) Filed: Jan. 12, 2012

(65) Prior Publication Data
US 2012/0184540 A1 Jul. 19, 2012

(30) Foreign Application Priority Data
Jan. 18, 2011 (EP) .................................... 11151294

(51) Int. Cl.
C07D 265/30 (2006.01)
C07D 413/12 (2006.01)
A61K 31/5375 (2006.01)
A61K 31/5377 (2006.01)
A61P 25/28 (2006.01)

(52) U.S. Cl.
CPC ............ C07D 265/30 (2013.01); C07D 413/12 (2013.01)

(58) Field of Classification Search
CPC .. C07D 265/30; C07D 417/12; C07D 413/12; A61K 31/5377; A61K 31/5375
USPC ................. 514/228.8, 211.15, 211.09; 544/98
See application file for complete search history.

(56) References Cited

U.S. PATENT DOCUMENTS

| | | | |
|---|---|---|---|
| 8,673,894 B2 * | 3/2014 | Banner et al. ............. | 514/211.01 |
| 8,748,418 B2 * | 6/2014 | Gabellieri et al. ........ | 514/211.01 |
| 8,785,436 B2 * | 7/2014 | Hilpert et al. ............. | 514/228.8 |
| 2007/0225267 A1 | 9/2007 | Broughton et al. | |
| 2011/0021520 A1 * | 1/2011 | Badiger ............... | C07D 265/30 514/233.2 |
| 2011/0190279 A1 | 8/2011 | Hori et al. | |
| 2011/0312937 A1 * | 12/2011 | Banner et al. ............. | 514/211.09 |
| 2012/0238548 A1 * | 9/2012 | Gabellieri et al. ........ | 514/211.15 |
| 2012/0295900 A1 * | 11/2012 | Hilpert et al. ............. | 514/230.5 |

FOREIGN PATENT DOCUMENTS

| | | |
|---|---|---|
| WO | 2009/151098 | 12/2009 |
| WO | 2010128058 | 11/2010 |
| WO | 2011020806 | 2/2011 |

OTHER PUBLICATIONS

Lagos et al., "Blood" 109(4):1550-1558 (2007).
Woodard-Grice et al., "J. Biol. Chem." 283(39):26364-26373 (2008).
Kihara et al., "Proceedings of the National Academy of Sciences of the USA" 106(51):21807-21812 (2009).
Akpinar et al., "Cell Metabolism" 2:385-397 (2005).
Desnues et al., "Clinical & Vaccine Immunology" 13(2):170-178 (2006).
Kondoh et al., "Breast Cancer Research Treatment" 78(1):37-44 (2003).
Hodges et al., "Human Molecular Genetics" 15(6):965-977 (2006).
Finzi et al., "Ultrastruct. Pathol." 32(6):246-251 (2008).
Basset et al., "Scandinavian Journal of Immunology" 51(3):307-311 (2000).
Vassar et al., "Science" ((5440)), 286:735-741 (1999).
Hoffmeister et al., "Journal of the Pancreas" 10(5):501-506 (2009).
Greenberg et al., "Annals of Neurology" 57(5):664-678 (2005).
Kim et al., "Neurobiology of Disease" 22(2):346-356 (2006).
Toegel et al., "Osteoarthritis & Cartilage" 18(2):240-248 (2010).
Li et al., "Aging Cell." 5(2):153-165 (2006).
Hedlund et al., "Cancer Research" 68(2):388-394 (2008).
International Search Report—PCT/EP2012/050537 mailed Feb. 21, 2012.
Grewal et al., "Molecular & Cellular Biology" 26(13):4970-4981 (2006).
Sugimoto et al., "J. Biol. Chem." 282(48):34896-34903 (2007).
Kuhn et al., "Journal of Biological Chemistry" 282(16):11982-11995 (2007).
Selkoe et al., "Annual Review Cell Biology" 10:373-403 (1994).
Gatchel et al., "Proceedings of the National Academy of Sciences of the USA" 105(4):1291-1296 (2008).
Maugeri et al., "Srp Arh Celok Lek" ((Suppl. 1)), 138:50-52 (2010).
Kiljanski et al., "Thyroid" 15(7):645-652 (2005).

(Continued)

*Primary Examiner* — Sreeni Padmanabhan
*Assistant Examiner* — Irina Neagu

(57) ABSTRACT

The present invention relates to 1,4 Oxazines of formula I

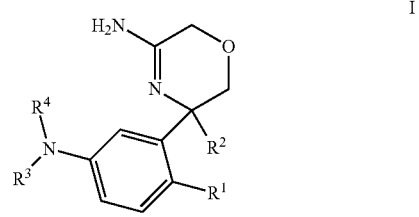

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

17 Claims, No Drawings

(56) References Cited

OTHER PUBLICATIONS

Zimmet et al., "Nature" 414:782-787 (2001).
McConlogue et al., "J. Biol. Chem." 282(36):26326-26334 (2007).
Wild et al., "Diabetes care" 27(5):1047-1053 (2004).
Talantov et al., "Clinical Cancer Research" 11(20):7234-7242 (2005).
Barbiero et al., "Experimental Neurology" 182(2):335-345 (2003).
Prentki et al., "The Journal of Clinical Investigation" 116(7):1802-1812 (2006).
Hardy et al., "Science" ((5580)), 297:353-356.
Baggio et al., "Annual Review of Medicine" 57:265-281 (2006).
Roberds et al., "Human Molecular Genetics" 10(12):1317-1324 (2001).
Koistinen et al., "Muscle & Nerve" 34(4):444-450 (2006).
Luo et al., "Nature Neuroscience" 3:231-232 (2001).
Hussain et al., "Molecular & Cellular Neurosciences" 16:609-619 (2000).
Merten et al., "Zeitschrift fur Kardiologie" ((English language Summary is attached to the reference)), 93(11):855-863 (2004).
Vattemi et al., "Lancet" ((9297)), 358:1962-1964 (2001).
Lichtenthaler et al., "J. Biol. Chem." 278(49):48713-48719 (2003).
The English translation of the Japanese Office Action, issued on Sep. 1, 2015, in the related Japanese Patent Application No. 2013-549780.

* cited by examiner

1,4 OXAZINES AS BACE1 AND/OR BACE2 INHIBITORS

PRIORITY TO RELATED APPLICATION(S)

This application claims the benefit of European Patent Application No. 11151294.3, filed Jan. 18, 2011, which is hereby incorporated by reference in its entirety.

FIELD OF THE INVENTION

The present invention relates to 3-Amino-5-phenyl-5,6-dihydro-2H-[1,4]oxazines having BACE1 and/or BACE2 inhibitory properties, their manufacture, pharmaceutical compositions containing them and their use as therapeutically active substances.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space, their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the trans-membrane aspartic protease BACE, *Science.* 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci.* 2001 March; 4(3):231-2, Roberds et al., BACE knockout mice are healthy despite lacking the primary beta-secretase activity in brain: implications for Alzheimer's disease therapeutics, *Hum Mol Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem.* 2007 Sep. 7; 282(36):26326). It is thus presumed that inhibitors of BACE1 activity can be useful agents for therapeutic intervention in Alzheimer's Disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting β-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases:
IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 Jan. 29; 105(4):1291-6), Dermatomyositis (Greenberg S. A. et al., Ann Neurol. 2005 May; 57(5):664-78 and Greenberg S. A. et al., *Neurol* 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol. Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. Oct. 15; 11(20):7234-42), Sjogren syndrome (Basset C. et al., Scand J. Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2): 388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

The present invention provides novel compounds of formula I, their manufacture, medicaments based on a compound in accordance with the invention and their production as well as the use of compounds of formula I in the control or prevention of illnesses such as Alzheimer's disease and type 2 diabetes. Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

SUMMARY OF THE INVENTION

The present invention provides a compounds of formula I,

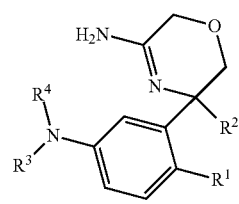

wherein the substituents and variables are as described below and in the claims, or a pharmaceutically acceptable salt thereof.

The present compounds have Asp2 (β-secretase, BACE1 or Memapsin-2) inhibitory activity and can therefore be used in the therapeutic and/or prophylactic treatment of diseases and disorders characterized by elevated β-amyloid levels and/or β-amyloid oligomers and/or β-amyloid plaques and further deposits, particularly Alzheimer's disease. And/or the present compounds have BACE2 inhibitory activity and can therefore be used in the therapeutic and/or prophylactic treatment of diseases and disorders such as type 2 diabetes and other metabolic disorders.

DETAILED DESCRIPTION OF THE INVENTION

The present invention provides compounds of formula I and their pharmaceutically acceptable salts, their preparation, pharmaceutical compositions containing them, and their manufacture as well as the use of the compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Optional" or "optionally" means that the subsequently described event or circumstance may, but need not, occur and that the description includes instances where the event or circumstance occurs and instances in which it does not.

The term "$C_{1-6}$-alkyl", alone or in combination with other groups, stands for a hydrocarbon radical which can be linear or branched, with single or multiple branching, whereby the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular alkyl groups are groups with 1 to 5 carbon atoms. Specific alkyl groups are methyl, ethyl, propyl, butyl, isopentyl, 2-ethyl-propyl and 1,2-dimethyl-propyl. Most specific is methyl.

The term "cyano-$C_{1-6}$-alkyl", alone or in combination with other groups, refers to $C_{1-6}$-alkyl as defined herein, which is substituted by one or multiple cyano, in particular 1-5 cyano, more particular 1 cyano. Examples are cyano-methyl and the like.

The term "halogen-$C_{1-6}$-alkyl", alone or in combination with other groups, refers to $C_{1-6}$-alkyl as defined herein, which is substituted by one or multiple halogen atoms, particularly 1-5 halogen atoms, more particularly 1-3 halogen atoms, most particularly 1 halogen atom or 3 halogen atoms. A particular halogen is fluoro. Examples are difluoromethyl, chloromethyl, fluoromethyl and the like. Specific examples are 2,2,3,3,3-pentafluoropropyl, 2,2-difluoroethyl and 2,2,2-trifluoroethyl.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy groups as defined herein. Examples are MeO-Me, 1MeO-Et, 2MeO-Et, 1MeO-2EtO-propyl and the like.

The term "$C_{1-6}$-alkyl-S—", alone or in combination with other groups, refers to $C_{1-6}$-alkyl, which is linked via S. Examples include methyl-S—.

The term "cyano", alone or in combination with other groups, refers to N≡C—(NC—).

The term "amido", alone or in combination with other groups, refers to —C(=O)—NH$_2$.

The term "amino", alone or in combination with other groups, refers to —NH$_2$.

The term "nitro", alone or in combination with other groups, refers to —NO$_2$.

The term "benzyl", alone or in combination with other groups, refers to phenyl-CH$_2$—.

The term "hydroxy", alone or in combination with other groups, refers to —OH.

The term "halogen", alone or in combination with other groups, denotes chloro (Cl), iodo (I), fluoro (F) and bromo (Br). Particular halogen are Cl and F, more specifically F.

The term "aryl", alone or in combination with other groups, refers to an aromatic carbocyclic group containing 6 to 14, particularly 6 to 10, carbon atoms and having at least one aromatic ring or multiple condensed rings in which at least one ring is aromatic. Examples of "aryl" include biphenyl, indanyl, naphthyl, phenyl (Ph) and the like. Particular "aryl" is phenyl.

The term "aryl-$C_{1-6}$-alkyl", alone or in combination with other groups, refers to an aryl group as defined herein linked via a $C_{1-6}$-alkyl group as defined herein. Examples include benzyl and phenyl-CH(CH$_3$)—.

The term "heteroaryl", alone or in combination with other groups, refers to a cyclic aromatic group having a single 4 to 8 membered ring or multiple condensed rings containing 6 to 14, in particular 6 to 10 ring atoms, of which 1, 2 or 3 of the ring atoms are heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular are pyridinyl, quinolinyl, isoxazolyl, 1H-indazolyl and 1H-benzoimidazolyl, 1H-pyrazolyl, benzooxazolyl and 6,7-dihydro-5H-[1]pyrindinyl. Specific are pyridine-2-yl, quinolin-8-yl, isoxazol-3-yl, 1H-indazol-3-yl and 1H-benzoimidazol-5-yl, 1H-pyrazol-3-yl, benzooxazol-4-yl and 6,7-dihydro-5H-[1]pyrindin-7-yl.

The term "heteroaryl-$C_{1-6}$-alkyl", alone or in combination with other groups, refers to a heteroaryl as defined herein linked via an "$C_{1-6}$-alkyl" as defined herein. Examples include pyridinyl-CH(CH(CH$_3$)$_2$)—, The term "heterocyclyl", alone or in combination with other groups, denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, or dihydropyranyl. A particular "heterocyclyl" is tetrahydrofuranyl. Other specific "heterocyclyl" are tetrahydrofuran-2-yl and tetrahydrofuran-3-yl.

The term "heterocyclyl-$C_{1-6}$-alkyl", alone or in combination with other groups, refers to a heterocyclyl group as defined herein linked via an "$C_{1-6}$-alkyl" as defined herein. Examples include tetrahydrofuranyl-$CH_2$—.

The term "$C_{1-6}$-alkoxy", alone or in combination with other groups, stands for an —O—$C_{1-6}$-alkyl radical which can be linear or branched, with single or multiple branching, whereby the alkyl group in general comprises 1 to 6 carbon atoms, for example, methoxy (OMe, MeO), ethoxy (OEt, propoxy, isopropoxy (i-propoxy), n-butoxy, i-butoxy (isobutoxy), 2-butoxy (sec-butoxy), t-butoxy (tert-butoxy), isopentyloxy (i-pentyloxy) and the like. Particular "$C_{1-6}$-alkoxy" groups are groups with 1 to 4 carbon atoms. Specific examples are methoxy and ethoxy.

The term "halogen-$C_{1-6}$-alkoxy", alone or in combination with other groups, refers to $C_{1-6}$-alkoxy as defined herein, which is substituted by one or multiple halogens, in particular fluoro. A particular "halogen-$C_{1-6}$-alkoxy" group is fluoro-$C_{1-6}$-alkoxy. Other specific "halogen-$C_{1-6}$-alkoxy" groups are difluoromethoxy, 2-fluoro-ethoxy, 2,2-difluoro-ethoxy and 2,2,2-trifluoro-ethoxy.

The term "$C_{3-7}$-cycloalkyl-$C_{1-6}$-alkoxy", alone or in combination with other groups, refers to $C_{1-6}$-alkoxy as defined herein, which is substituted by one cycloalkyl as defined herein. Examples are cyclopropyl-ethoxy, cyclopropyl-methoxy and the like.

The term "$C_{3-7}$-cycloalkyl", alone or in combination with other groups, denotes a monovalent saturated monocyclic or bicyclic hydrocarbon group of 3 to 7 ring carbon atoms, particularly a monovalent saturated monocyclic hydrocarbon group of 3 to 6 ring carbon atoms. Bicyclic means consisting of two saturated carbocycles having two carbon atoms in common, i.e. the bridge separating the two rings is either a single bond or a chain of one or two carbon atoms. Particular cycloalkyl groups are monocyclic. Examples for monocyclic cycloalkyl are cyclopropyl, cyclobutanyl, cyclopentyl, cyclohexyl and cycloheptyl. Examples for bicyclic cycloalkyl are bicyclo[2.2.1]heptanyl, bicyclo[2.2.2]octanyl and adamantanyl. Particular cycloalkyl groups are cyclopropyl, cyclobutyl, cyclopentyl, cyclohexyl and bicyclo[2.2.1]heptanyl. Specific examples are cyclopropyl, cyclobutyl, cyclopentyl, cyclohexyl and bicyclo[2.2.1]heptane-2-yl.

The term "$C_{3-7}$-cycloalkyl-$C_{1-6}$-alkyl", alone or in combination with other groups, refers to a $C_{3-7}$-cycloalkyl as defined herein linked via a "$C_{1-6}$-alkyl" as defined herein. Examples include cyclopropyl-$CH_2$—.

The term "$C_{3-7}$-cycloalkyl-$C_{2-6}$-alkenyl", alone or in combination with other groups, refers to a $C_{3-7}$-cycloalkyl as defined herein linked via a "$C_{2-6}$-alkenyl" as defined herein. Examples include cyclopropyl-CH═CH—.

The term "$C_{3-7}$-cycloalkyl-$C_{2-6}$-alkynyl", alone or in combination with other groups, refers to a $C_{3-7}$-cycloalkyl as defined herein linked via a "$C_{2-6}$-alkynyl" as defined herein. Examples include cyclopropyl-C≡C—.

The term "$C_{2-6}$-alkenyl", alone or in combination with other groups, denotes a monovalent linear or branched hydrocarbon group of 2 to 6 carbon atoms, in particular 2 to 4 carbon atoms, with at least one double bond. Examples of $C_{2-6}$-alkenyl include ethenyl, propenyl, prop-2-enyl, isopropenyl, n-butenyl, i-butenyl, and t-butenyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and containing one, two or three triple bonds. Examples of $C_{2-6}$-alkynyl include ethynyl, propynyl, prop-2-ynyl, isopropynyl and n-butynyl.

The term "pharmaceutically acceptable salts" refers to salts that are suitable for use in contact with the tissues of humans and animals. Suitable salts are those formed with inorganic and organic acids such as, but are not limited to, acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular salts are formed from formic acid, trifluoroacetic acid and hydrochloric acid, more specifically hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product containing specified ingredients in pre-determined amounts or proportions, as well as any product that results, directly or indirectly, from combining specified ingredients in specified amounts. In particular it encompasses a product containing one or more active ingredients, and an optional carrier containing inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "treating" or "treatment" of a disease state includes (1) preventing the disease state, i.e. causing the clinical symptoms of the disease state not to develop in a subject that can be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as in particular, more particular and most particular definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group, a bis(dimethoxyphenyl)-phenylmethyl and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

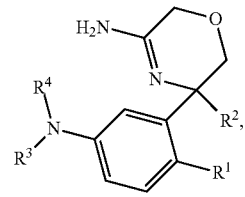

wherein
$R^1$ is selected from the group consisting of
i) hydrogen,
ii) halogen, and
iii) $C_{1-6}$-alkyl;
$R^2$ is $C_{1-6}$-alkyl;
$R^3$ is selected from the group consisting of
i) aryl,
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
iii) aryl-$C_{1-6}$-alkyl,
iv) aryl-$C_{1-6}$-alkyl, wherein the aryl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
v) heteroaryl,
vi) heteroaryl substituted by 1-4 substituents individually selected from amido, cyano, cyano-$C_{1-6}$-alkyl, $C_{3-7}$-cycloalkyl, $C_{3-7}$-cycloalkyl-$C_{2-6}$-alkenyl, $C_{3-7}$-cycloalkyl-$C_{2-6}$-alkynyl, $C_{3-7}$-cycloalkyl-$C_{1-6}$-alkyl, $C_{3-7}$-cycloalkyl-$C_{1-6}$-alkoxy, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl, $C_{1-6}$-alkyl and nitro;
vii) heteroaryl-$C_{1-6}$-alkyl,
viii) heteroaryl-$C_{1-6}$-alkyl, wherein the heteroaryl is substituted by 1-4 substituents individually selected from amido, cyano, cyano-$C_{1-6}$-alkyl, $C_{3-7}$-cycloalkyl, $C_{3-7}$-cycloalkyl-$C_{2-6}$-alkenyl, $C_{3-7}$-cycloalkyl-$C_{2-6}$-alkynyl, $C_{3-7}$-cycloalkyl-$C_{1-6}$-alkyl, $C_{3-7}$-cycloalkyl-$C_{1-6}$-alkoxy, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl, $C_{1-6}$-alkyl and nitro,
ix) $C_{1-6}$-alkyl,
x) $C_{1-6}$-alkyl substituted by 1-5 substituents individually selected from cyano, halogen, hydroxy, $C_{1-6}$-alkyl-S— and $C_{1-6}$-alkoxy,
xi) $C_{3-7}$-cycloalkyl,
xii) $C_{3-7}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, hydroxy, $C_{1-6}$-alkoxy, $C_{1-6}$-alkoxy-$C_{1-6}$-alkyl and $C_{1-6}$-alkyl, xiii) $C_{3-7}$-cycloalkyl-$C_{1-6}$-alkyl, xiv) $C_{3-7}$-cycloalkyl-$C_{1-6}$-alkyl, wherein the $C_{3-7}$-cycloalkyl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl, xv) heterocyclyl, xvi) heterocyclyl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl, xvii) heterocyclyl-$C_{1-6}$-alkyl, and xviii) heterocyclyl-$C_{1-6}$-alkyl, wherein the heterocyclyl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl; and $R^4$ is hydrogen;

or pharmaceutically acceptable salts thereof.

A certain embodiment of the invention provides a compound of formula I as described herein, wherein $R^1$ is selected from the group consisting of i) hydrogen, and ii) halogen;

$R^2$ is $C_{1-6}$-alkyl;

$R^3$ is selected from the group consisting of i) aryl substituted by 1-2 substituents individually halogen and halogen-$C_{1-6}$-alkoxy, ii) aryl-$C_{1-6}$-alkyl, wherein the aryl is substituted by 1-2 halogen;

iii) heteroaryl, iv) heteroaryl substituted by 1-2 substituents individually selected from $C_{3-7}$-cycloalkyl, $C_{3-7}$-cycloalkyl-$C_{1-6}$-alkoxy, halogen, halogen-$C_{1-6}$-alkoxy, $C_{1-6}$-alkoxy and $C_{1-6}$-alkyl, v) heteroaryl-$C_{1-6}$-alkyl, wherein the heteroaryl is substituted by 1-2 substituents individually selected from halogen and $C_{1-6}$-alkyl, vi) $C_{1-6}$-alkyl, vii) $C_{1-6}$-alkyl substituted by 1-5 halogen or $C_{1-6}$-alkyl-S—, viii) $C_{3-7}$-cycloalkyl, ix) $C_{3-7}$-cycloalkyl substituted by 1-2 substituents individually selected from hydroxy and $C_{1-6}$-alkyl, x) $C_{3-7}$-cycloalkyl-$C_{1-6}$-alkyl, xi) heterocyclyl, and xii) heterocyclyl-$C_{1-6}$-alkyl; and $R^4$ is hydrogen.

A certain embodiment of the invention provides a compound of formula I as described herein, wherein $R^1$ is halogen.

A certain embodiment of the invention provides a compound of formula I as described herein, wherein $R^1$ is F.

A certain embodiment of the invention provides a compound of formula I as described herein, wherein $R^1$ is hydrogen.

A certain embodiment of the invention provides a compound of formula I as described herein, wherein $R^2$ is methyl.

A certain embodiment of the invention provides a compound of formula I as described herein, wherein $R^4$ is hydrogen.

A certain embodiment of the invention provides a compound of formula I as described herein, wherein $R^3$ is selected from the group consisting of i) aryl substituted by 1-2 substituents individually selected from halogen and halogen-$C_{1-6}$-alkoxy, ii) aryl-$C_{1-6}$-alkyl, wherein the aryl is substituted by 1-2 halogen, iii) heteroaryl, iv) heteroaryl substituted by 1-2 substituents individually selected from $C_{3-7}$-cycloalkyl, $C_{3-7}$-cycloalkyl-$C_{1-6}$-alkoxy, halogen, halogen-$C_{1-6}$-alkoxy, $C_{1-6}$-alkoxy and $C_{1-6}$-alkyl, v) heteroaryl-$C_{1-6}$-alkyl, wherein the heteroaryl is substituted by 1-2 substituents individually selected from halogen and halogen-$C_{1-6}$-alkyl, vi) $C_{1-6}$-alkyl, vii) $C_{1-6}$-alkyl substituted by 1-5 halogen or $C_{1-6}$-alkyl-S—, viii) $C_{3-7}$-cycloalkyl, ix) $C_{3-7}$-cycloalkyl substituted by 1-2 substituents individually selected from hydroxy and $C_{1-6}$-alkyl, x) $C_{3-7}$-cycloalkyl-$C_{1-6}$-alkyl, xi) heterocyclyl, and xii) heterocyclyl-$C_{1-6}$-alkyl.

A certain embodiment of the invention provides a compound of formula I as described herein, wherein $R^3$ is aryl substituted by 1-2 substituents individually selected from halogen and halogen-$C_{1-6}$-alkoxy.

A certain embodiment of the invention provides a compound of formula I as described herein, wherein $R^3$ is 2-(2,2-difluoro-ethoxy)-phenyl.

A certain embodiment of the invention provides a compound of formula I as described herein, wherein $R^3$ is 2-(2,2,2-trifluoro-ethoxy)-phenyl.

A certain embodiment of the invention provides a compound of formula I as described herein, wherein $R^3$ is 2-(2-fluoro-ethoxy)-phenyl.

A certain embodiment of the invention provides a compound of formula I as described herein, wherein $R^3$ is 2-difluoromethoxy-phenyl.

A certain embodiment of the invention provides a compound of formula I as described herein, wherein $R^3$ is 5-chloro-indan-1-yl.

A certain embodiment of the invention provides a compound of formula I as described herein, wherein $R^3$ is aryl-$C_{1-6}$-alkyl, wherein the aryl is substituted by 1-2 halogen.

A certain embodiment of the invention provides a compound of formula I as described herein, wherein $R^3$ is 3-chloro-benzyl.

A certain embodiment of the invention provides a compound of formula I as described herein, wherein $R^3$ is 4-chloro-benzyl.

A certain embodiment of the invention provides a compound of formula I as described herein, wherein $R^3$ is 2,4-dichloro-benzyl.

A certain embodiment of the invention provides a compound of formula I as described herein, wherein $R^3$ is 4-chloro-phenyl-CH(CH$_3$)—.

A certain embodiment of the invention provides a compound of formula I as described herein, wherein $R^3$ is heteroaryl.

A certain embodiment of the invention provides a compound of formula I as described herein, wherein $R^3$ is quinolin-8-yl.

A certain embodiment of the invention provides a compound of formula I as described herein, wherein $R^3$ is isoxazol-3-yl.

A certain embodiment of the invention provides a compound of formula I as described herein, wherein $R^3$ is heteroaryl substituted by 1-2 substituents individually selected from $C_{3-7}$-cycloalkyl, $C_{3-7}$-cycloalkyl-$C_{1-6}$-alkoxy, halogen, halogen-$C_{1-6}$-alkoxy, $C_{1-6}$-alkoxy and $C_{1-6}$-alkyl.

A certain embodiment of the invention provides a compound of formula I as described herein, wherein $R^3$ is 2-cyclopropyl-benzooxazol-4-yl.

A certain embodiment of the invention provides a compound of formula I as described herein, wherein $R^3$ is 3-chloro-6,7-dihydro-5H-[1]pyrindin-7-yl.

A certain embodiment of the invention provides a compound of formula I as described herein, wherein $R^3$ is 3-chloro-quinolin-8-yl.

A certain embodiment of the invention provides a compound of formula I as described herein, wherein $R^3$ is 3,6-dichloro-quinolin-8-yl.

A certain embodiment of the invention provides a compound of formula I as described herein, wherein $R^3$ is 3-chloro-6-fluoro-quinolin-8-yl.

A certain embodiment of the invention provides a compound of formula I as described herein, wherein $R^3$ is 3-difluoromethoxy-quinolin-8-yl.

A certain embodiment of the invention provides a compound of formula I as described herein, wherein $R^3$ is 3-(2-fluoro-ethoxy)-quinolin-8-yl.

A certain embodiment of the invention provides a compound of formula I as described herein, wherein $R^3$ is 3-cyclopropylmethoxy-6-fluoro-quinolin-8-yl.

A certain embodiment of the invention provides a compound of formula I as described herein, wherein $R^3$ is 3-(2,2,2-trifluoro-ethoxy)-quinolin-8-yl.

A certain embodiment of the invention provides a compound of formula I as described herein, wherein $R^3$ is 3-methoxy-quinolin-8-yl.

A certain embodiment of the invention provides a compound of formula I as described herein, wherein $R^3$ is 1,2-dimethyl-1H-benzoimidazol-5-yl.

A certain embodiment of the invention provides a compound of formula I as described herein, wherein $R^3$ is 6-chloro-1-methyl-1H-indazol-3-yl.

A certain embodiment of the invention provides a compound of formula I as described herein, wherein $R^3$ is heteroaryl-$C_{1-6}$-alkyl, wherein the heteroaryl is substituted by 1-2 substituents individually selected from halogen and halogen-$C_{1-6}$-alkyl.

A certain embodiment of the invention provides a compound of formula I as described herein, wherein $R^3$ is 4-chloro-1-(difluoromethyl)-1H-pyrazol-3-yl)methyl.

A certain embodiment of the invention provides a compound of formula I as described herein, wherein $R^3$ is 5-chloro-pyridin-2-yl-CH(CH(CH$_3$)$_2$).

A certain embodiment of the invention provides a compound of formula I as described herein, wherein $R^3$ is $C_{1-6}$-alkyl.

A certain embodiment of the invention provides a compound of formula I as described herein, wherein $R^3$ is butyl.

A certain embodiment of the invention provides a compound of formula I as described herein, wherein $R^3$ is isopentyl.

A certain embodiment of the invention provides a compound of formula I as described herein, wherein $R^3$ is 2-ethyl-propyl.

A certain embodiment of the invention provides a compound of formula I as described herein, wherein $R^3$ is 1,2-dimethyl-propyl.

A certain embodiment of the invention provides a compound of formula I as described herein, wherein $R^3$ is $C_{1-6}$-alkyl substituted by 1-5 halogen or $C_{1-6}$-alkyl-S—.

A certain embodiment of the invention provides a compound of formula I as described herein, wherein $R^3$ is 2,2,2-trifluoroethyl.

A certain embodiment of the invention provides a compound of formula I as described herein, wherein $R^3$ is 2,2-difluoroethyl.

A certain embodiment of the invention provides a compound of formula I as described herein, wherein $R^3$ is 2,2,3,3,3-pentafluoropropyl.

A certain embodiment of the invention provides a compound of formula I as described herein, wherein $R^3$ is 3,3,3-trifluoropropyl.

A certain embodiment of the invention provides a compound of formula I as described herein, wherein $R^3$ is 3-(methylthio)propyl.

A certain embodiment of the invention provides a compound of formula I as described herein, wherein $R^3$ is $C_{3-7}$-cycloalkyl.

A certain embodiment of the invention provides a compound of formula I as described herein, wherein $R^3$ is cyclobutyl.

A certain embodiment of the invention provides a compound of formula I as described herein, wherein $R^3$ is cyclopropyl.

A certain embodiment of the invention provides a compound of formula I as described herein, wherein $R^3$ is cyclohexyl.

A certain embodiment of the invention provides a compound of formula I as described herein, wherein $R^3$ is $C_{3-7}$-cycloalkyl substituted by 1-2 substituents individually selected from hydroxy and $C_{1-6}$-alkyl.

A certain embodiment of the invention provides a compound of formula I as described herein, wherein $R^3$ is 7,7-dimethyl bicyclo[2.2.1]heptane-2-yl.

A certain embodiment of the invention provides a compound of formula I as described herein, wherein $R^3$ is 2-hydroxy-cyclopent-1-yl.

A certain embodiment of the invention provides a compound of formula I as described herein, wherein $R^3$ is $C_{3-7}$-cycloalkyl-$C_{1-6}$-alkyl.

A certain embodiment of the invention provides a compound of formula I as described herein, wherein $R^3$ is cyclopropylmethyl.

A certain embodiment of the invention provides a compound of formula I as described herein, wherein $R^3$ is heterocyclyl.

A certain embodiment of the invention provides a compound of formula I as described herein, wherein $R^3$ is tetrahydro-furan-3-yl.

A certain embodiment of the invention provides a compound of formula I as described herein, wherein $R^3$ is heterocyclyl-$C_{1-6}$-alkyl.

A certain embodiment of the invention provides a compound of formula I as described herein, wherein $R^3$ is tetrahydrofuran-2-yl-methyl.

A certain embodiment of the invention provides a compound of formula I as described herein, wherein $R^3$ is selected from the group consisting of
i) aryl substituted by 1-2 substituents individually selected from halogen and halogen-$C_{1-6}$-alkoxy,
ii) $C_{3-7}$-cycloalkyl,
iii) heteroaryl substituted by 1-2 substituents individually selected from halogen and $C_{1-6}$-alkoxy, and
iv) heteroaryl-$C_{1-6}$-alkyl, wherein the heteroaryl is substituted by 1-2 substituents individually selected from halogen and halogen-$C_{1-6}$-alkyl.

A certain embodiment of the invention provides a compound of formula I as described herein, wherein $R^3$ is selected from the group consisting of i) benzyl substituted by 1 or 2 chloro;
ii) phenyl-CH(CH$_3$)—, wherein the phenyl is substituted by chloro,
iii) phenyl substituted by difluoromethoxy, 2-fluoro-ethoxy, 2,2-difluoro-ethoxy or 2,2,2-trifluoro-ethoxy,
iv) ethyl substituted by 1 or 2 or 3 fluoro,
v) propyl substituted by 1 or 2 or 3 or 4 or 5 fluoro,
vi) propyl substituted —S—CH$_3$,
vii) butyl,
viii) isopentyl,
ix) 2-ethyl-propyl,
x) 1,2-dimethyl-propyl,
xi) cyclopropyl unsubstituted or substituted by OH,
xii) cyclobutyl,
xiii) cyclopentyl substituted by OH,
xiv) cyclohexyl,
xv) bicyclo[2.2.1]heptanyl substituted by 1 or 2 methyl,
xvi) tetrahydrofuranyl,
xvii) cyclopropyl-CH$_2$—,
xviii) tetrahydrofuranyl-CH$_2$—,
xix) pyridinyl-CH(CH(CH$_3$)$_2$)—, wherein the pyridinyl is substituted by chloro,
xx) quinolinyl unsubstituted or substituted by 1 or 2 chloro, fluoro and chloro, difluoromethoxy, 2-fluoro-ethoxy, fluoro and cyclopropylmethoxy, 2,2,2-trifluoro-ethoxy or methoxy,
xxi) isoxazolyl,
xxii) 1H-indazolyl substituted by chloro and methyl,
xxiii) indanyl substituted by chloro,
xxiv) 1H-benzoimidazolyl substituted by 1 or 2 methyl,
xxv) 6,7-dihydro-5H-[1]pyrindinyl substituted by chloro,
xxvi) 1H-pyrazolyl substituted by difluoromethyl and chloro, and
xxvii) benzoxazolyl substituted by cyclopropyl.

A certain embodiment of the invention provides a compound of formula I as described herein, wherein R$^3$ is selected from the group consisting of
i) phenyl substituted by 2,2-difluoro-ethoxy,
ii) cyclopropyl,
iii) quinolinyl substituted by chloro,
iv) quinolinyl substituted by chloro and fluoro,
v) quinolinyl substituted by methoxy,
vi) indanyl substituted by chloro, and
vii) 1H-pyrazolyl substituted by difluoromethyl and chloro.

A certain embodiment of the invention provides a compound of formula I as described herein, selected from the group consisting of
5-[3-(3-Chloro-benzylamino)-phenyl]-5-methyl-5,6-dihydro-2H-[1,4]oxazin-3-ylamine,
(1R,2S)-2-(3-((R)-5-amino-3-methyl-3,6-dihydro-2H-1,4-oxazin-3-yl)-4-fluorophenylamino)cyclopentanol,
(1S,2S)-2-(3-((R)-5-amino-3-methyl-3,6-dihydro-2H-1,4-oxazin-3-yl)-4-fluorophenylamino)cyclopentanol,
(5R)-5-(2-fluoro-5-(3-methylbutan-2-ylamino)phenyl)-5-methyl-5,6-dihydro-2H-1,4-oxazin-3-amine,
(R)-5-(2-fluoro-5-(((R)-tetrahydrofuran-2-yl)methylamino) phenyl)-5-methyl-5,6-dihydro-2H-1,4-oxazin-3-amine,
(R)-5-(2-fluoro-5-(2,2,2-trifluoroethylamino)phenyl)-5-methyl-5,6-dihydro-2H-1,4-oxazin-3-amine,
(R)-5-(2-fluoro-5-(2,2,3,3,3-pentafluoropropylamino)phenyl)-5-methyl-5,6-dihydro-2H-1,4-oxazin-3-amine,
(R)-5-(2-fluoro-5-(3-(methylthio)propylamino)phenyl)-5-methyl-5,6-dihydro-2H-1,4-oxazin-3-amine,
(R)-5-(2-fluoro-5-(3,3,3-trifluoropropylamino)phenyl)-5-methyl-5,6-dihydro-2H-1,4-oxazin-3-amine,
(R)-5-(2-fluoro-5-(isopentylamino)phenyl)-5-methyl-5,6-dihydro-2H-1,4-oxazin-3-amine,
(R)-5-(2-fluoro-5-(pentan-3-ylamino)phenyl)-5-methyl-5,6-dihydro-2H-1,4-oxazin-3-amine,
5-[(R)-5-((1R,2R,4R)-7,7-dimethyl-bicyclo[2.2.1]hept-2-ylamino)-2-fluoro-phenyl]-5-methyl-5,6-dihydro-2H-[1,4]oxazin-3-ylamine,
(R)-5-(5-((4-chloro-1-(difluoromethyl)-1H-pyrazol-3-yl) methylamino)-2-fluorophenyl)-5-methyl-5,6-dihydro-2H-1,4-oxazin-3-amine,
(R)-5-[5-(2,2-Difluoro-ethylamino)-2-fluoro-phenyl]-5-methyl-5,6-dihydro-2H-[1,4]oxazin-3-ylamine,
(R)-5-(5-(butylamino)-2-fluorophenyl)-5-methyl-5,6-dihydro-2H-1,4-oxazin-3-amine,
(R)-5-(5-(cyclohexylamino)-2-fluorophenyl)-5-methyl-5,6-dihydro-2H-1,4-oxazin-3-amine,
(R)-5-(5-(cyclopentylamino)-2-fluorophenyl)-5-methyl-5,6-dihydro-2H-1,4-oxazin-3-amine,
(R)-5-(5-(cyclopropylmethylamino)-2-fluorophenyl)-5-methyl-5,6-dihydro-2H-1,4-oxazin-3-amine,
(R)-5-(5-Cyclobutylamino-2-fluoro-phenyl)-5-methyl-5,6-dihydro-2H-[1,4]oxazin-3-ylamine,
(R)-5-[2-Fluoro-5-(isoxazol-3-ylamino)-phenyl]-5-methyl-5,6-dihydro-2H-[1,4]oxazin-3-ylamine,
(R)-5-[2-Fluoro-5-(tetrahydro-furan-3-ylamino)-phenyl]-5-methyl-5,6-dihydro-2H-[1,4]oxazin-3-ylamine,
(R)-5-{2-Fluoro-5-[2-(2,2,2-trifluoro-ethoxy)-phenylamino]-phenyl}-5-methyl-5,6-dihydro-2H-[1,4]oxazin-3-ylamine,
(R)-5-{2-Fluoro-5-[2-(2-fluoro-ethoxy)-phenylamino]-phenyl}-5-methyl-5,6-dihydro-2H-[1,4]oxazin-3-ylamine,
(R)-5-{5-[1-(5-Chloro-pyridin-2-yl)-2-methyl-propylamino]-2-fluoro-phenyl}-5-methyl-5,6-dihydro-2H-[1,4]oxazin-3-ylamine,
(R)-5-{5-[2-(2,2-Difluoro-ethoxy)-phenylamino]-2-fluoro-phenyl}-5-methyl-5,6-dihydro-2H-[1,4]oxazin-3-ylamine,
(S)-5-(5-(6-chloro-1-methyl-1H-indazol-3-ylamino)-2-fluorophenyl)-5-methyl-5,6-dihydro-2H-1,4-oxazin-3-amine,
(S)-5-[5-(5-Chloro-indan-1-ylamino)-2-fluoro-phenyl]-5-methyl-5,6-dihydro-2H-[1,4]oxazin-3-ylamine,
[3-((R)-5-Amino-3-methyl-3,6-dihydro-2H-[1,4]oxazin-3-yl)-4-fluoro-phenyl]-(3-chloro-quinolin-8-yl)-amine,
[3-((R)-5-Amino-3-methyl-3,6-dihydro-2H-[1,4]oxazin-3-yl)-4-fluoro-phenyl]-(3,6-dichloro-quinolin-8-yl)-amine,
[3-((R)-5-Amino-3-methyl-3,6-dihydro-2H-[1,4]oxazin-3-yl)-4-fluoro-phenyl]-(3-chloro-6-fluoro-quinolin-8-yl)-amine,
[3-((R)-5-Amino-3-methyl-3,6-dihydro-2H-[1,4]oxazin-3-yl)-4-fluoro-phenyl]-(3-difluoromethoxy-quinolin-8-yl)-amine,
[3-((R)-5-Amino-3-methyl-3,6-dihydro-2H-[1,4]oxazin-3-yl)-4-fluoro-phenyl]-[3-(2-fluoro-ethoxy)-quinolin-8-yl]-amine,
[3-((R)-5-Amino-3-methyl-3,6-dihydro-2H-[1,4]oxazin-3-yl)-4-fluoro-phenyl]-(3-cyclopropylmethoxy-6-fluoro-quinolin-8-yl)-amine,
[3-((R)-5-Amino-3-methyl-3,6-dihydro-2H-[1,4]oxazin-3-yl)-4-fluoro-phenyl]-[3-(2,2,2-trifluoro-ethoxy)-quinolin-8-yl]-amine,
[3-((R)-5-Amino-3-methyl-3,6-dihydro-2H-[1,4]oxazin-3-yl)-4-fluoro-phenyl]-(3-chloro-6,7-dihydro-5H-[1]pyrindin-7-yl)-amine,
[3-(5-Amino-3-methyl-3,6-dihydro-2H-[1,4]oxazin-3-yl)-phenyl]-(1,2-dimethyl-1H-benzoimidazol-5-yl)-amine,
[3-(5-Amino-3-methyl-3,6-dihydro-2H-[1,4]oxazin-3-yl)-phenyl]-(2-cyclopropyl-benzooxazol-4-yl)-amine,
[3-(5-Amino-3-methyl-3,6-dihydro-2H-[1,4]oxazin-3-yl)-phenyl]-(3-chloro-quinolin-8-yl)-amine,

[3-(5-Amino-3-methyl-3,6-dihydro-2H-[1,4]oxazin-3-yl)-phenyl]-(3-chloro-6-fluoro-quinolin-8-yl)-amine,
[3-(5-Amino-3-methyl-3,6-dihydro-2H-[1,4]oxazin-3-yl)-phenyl]-(3-methoxy-quinolin-8-yl)-amine,
[3-(5-Amino-3-methyl-3,6-dihydro-2H-[1,4]oxazin-3-yl)-phenyl]-quinolin-8-yl-amine,
5-[3-(2,4-Dichloro-benzylamino)-phenyl]-5-methyl-5,6-dihydro-2H-[1,4]oxazin-3-ylamine,
5-[3-(2-Difluoromethoxy-phenylamino)-phenyl]-5-methyl-5,6-dihydro-2H-[1,4]oxazin-3-ylamine,
5-[3-(4-Chloro-benzylamino)-phenyl]-5-methyl-5,6-dihydro-2H-[1,4]oxazin-3-ylamine,
5-[3-(5-Chloro-indan-1-ylamino)-phenyl]-5-methyl-5,6-dihydro-2H-[1,4]oxazin-3-ylamine, and
5-{3-[1-(4-Chloro-phenyl)-ethylamino]-phenyl}-5-methyl-5,6-dihydro-2H-[1,4]oxazin-3-ylamine, or a pharmaceutical acceptable salt thereof.

A certain embodiment of the invention provides a compound of formula I as described herein, selected from the group consisting of
(R)-5-(5-(cyclopentylamino)-2-fluorophenyl)-5-methyl-5,6-dihydro-2H-1,4-oxazin-3-amine,
(R)-5-(5-((4-chloro-1-(difluoromethyl)-1H-pyrazol-3-yl)methylamino)-2-fluorophenyl)-5-methyl-5,6-dihydro-2H-1,4-oxazin-3-amine hydrochloride,
(R)-5-{5-[2-(2,2-Difluoro-ethoxy)-phenylamino]-2-fluoro-phenyl}-5-methyl-5,6-dihydro-2H-[1,4]oxazin-3-ylamine hydrochloride,
(S)-5-[5-(5-Chloro-indan-1-ylamino)-2-fluoro-phenyl]-5-methyl-5,6-dihydro-2H-[1,4]oxazin-3-ylamine hydrochloride,
[3-((R)-5-Amino-3-methyl-3,6-dihydro-2H-[1,4]oxazin-3-yl)-4-fluoro-phenyl]-(3-chloro-quinolin-8-yl)-amine hydrochloride,
[3-((R)-5-Amino-3-methyl-3,6-dihydro-2H-[1,4]oxazin-3-yl)-4-fluoro-phenyl]-(3-chloro-6-fluoro-quinolin-8-yl)-amine hydrochloride,
[3-(5-Amino-3-methyl-3,6-dihydro-2H-[1,4]oxazin-3-yl)-phenyl]-(3-chloro-quinolin-8-yl)-amine hydrochloride,
[3-(5-Amino-3-methyl-3,6-dihydro-2H-[1,4]oxazin-3-yl)-phenyl]-(3-methoxy-quinolin-8-yl)-amine hydrochloride, and
5-[3-(5-Chloro-indan-1-ylamino)-phenyl]-5-methyl-5,6-dihydro-2H-[1,4]oxazin-3-ylamine.

A certain embodiment of the invention provides a compound of formula I as described herein, selected from the group consisting of
5-[3-(3-Chloro-benzylamino)-phenyl]-5-methyl-5,6-dihydro-2H-[1,4]oxazin-3-ylamine,
(1R,2S)-2-(3-((R)-5-amino-3-methyl-3,6-dihydro-2H-1,4-oxazin-3-yl)-4-fluorophenylamino) cyclopentanol,
(1S,2S)-2-(3-((R)-5-amino-3-methyl-3,6-dihydro-2H-1,4-oxazin-3-yl)-4-fluorophenylamino) cyclopentanol,
(5R)-5-(2-fluoro-5-(3-methylbutan-2-ylamino)phenyl)-5-methyl-5,6-dihydro-2H-1,4-oxazin-3-amine,
(R)-5-(2-fluoro-5-(((R)-tetrahydrofuran-2-yl)methylamino)phenyl)-5-methyl-5,6-dihydro-2H-1,4-oxazin-3-amine,
(R)-5-(2-fluoro-5-(2,2,2-trifluoroethylamino)phenyl)-5-methyl-5,6-dihydro-2H-1,4-oxazin-3-amine,
(R)-5-(2-fluoro-5-(2,2,3,3,3-pentafluoropropylamino)phenyl)-5-methyl-5,6-dihydro-2H-1,4-oxazin-3-amine,
(R)-5-(2-fluoro-5-(3-(methylthio)propylamino)phenyl)-5-methyl-5,6-dihydro-2H-1,4-oxazin-3-amine,
(R)-5-(2-fluoro-5-(3,3,3-trifluoropropylamino)phenyl)-5-methyl-5,6-dihydro-2H-1,4-oxazin-3-amine,
(R)-5-(2-fluoro-5-(isopentylamino)phenyl)-5-methyl-5,6-dihydro-2H-1,4-oxazin-3-amine,
(R)-5-(2-fluoro-5-(pentan-3-ylamino)phenyl)-5-methyl-5,6-dihydro-2H-1,4-oxazin-3-amine,
5-[(R)-5-(((1R,2R,4R)-7,7-dimethyl-bicyclo[2.2.1]hept-2-ylamino)-2-fluoro-phenyl]-5-methyl-5,6-dihydro-2H-[1,4]oxazin-3-ylamine,
(R)-5-(5-((4-chloro-1-(difluoromethyl)-1H-pyrazol-3-yl)methylamino)-2-fluorophenyl)-5-methyl-5,6-dihydro-2H-1,4-oxazin-3-amine,
(R)-5-[5-(2,2-Difluoro-ethylamino)-2-fluoro-phenyl]-5-methyl-5,6-dihydro-2H-[1,4]oxazin-3-ylamine,
(R)-5-(5-(butylamino)-2-fluorophenyl)-5-methyl-5,6-dihydro-2H-1,4-oxazin-3-amine,
(R)-5-(5-(cyclohexylamino)-2-fluorophenyl)-5-methyl-5,6-dihydro-2H-1,4-oxazin-3-amine,
(R)-5-(5-(cyclopentylamino)-2-fluorophenyl)-5-methyl-5,6-dihydro-2H-1,4-oxazin-3-amine,
(R)-5-(5-(cyclopropylmethylamino)-2-fluorophenyl)-5-methyl-5,6-dihydro-2H-1,4-oxazin-3-amine,
(R)-5-(5-Cyclobutylamino-2-fluoro-phenyl)-5-methyl-5,6-dihydro-2H-[1,4]oxazin-3-ylamine,
(R)-5-[2-Fluoro-5-(isoxazol-3-ylamino)-phenyl]-5-methyl-5,6-dihydro-2H-[1,4]oxazin-3-ylamine trifluoro acetate,
(R)-5-[2-Fluoro-5-(tetrahydro-furan-3-ylamino)-phenyl]-5-methyl-5,6-dihydro-2H-[1,4]oxazin-3-ylamine,
(R)-5-{2-Fluoro-5-[2-(2,2,2-trifluoro-ethoxy)-phenylamino]-phenyl}-5-methyl-5,6-dihydro-2H-[1,4]oxazin-3-ylamine hydrochloride,
(R)-5-{2-Fluoro-5-[2-(2-fluoro-ethoxy)-phenylamino]-phenyl}-5-methyl-5,6-dihydro-2H-[1,4]oxazin-3-ylamine hydrochloride,
(R)-5-{5-[1-(5-Chloro-pyridin-2-yl)-2-methyl-propylamino]-2-fluoro-phenyl}-5-methyl-5,6-dihydro-2H-[1,4]oxazin-3-ylamine hydrochloride,
(R)-5-{5-[2-(2,2-Difluoro-ethoxy)-phenylamino]-2-fluoro-phenyl}-5-methyl-5,6-dihydro-2H-[1,4]oxazin-3-ylamine hydrochloride,
(S)-5-(5-(6-chloro-1-methyl-1H-indazol-3-ylamino)-2-fluorophenyl)-5-methyl-5,6-dihydro-2H-1,4-oxazin-3-amine,
(S)-5-[5-(5-Chloro-indan-1-ylamino)-2-fluoro-phenyl]-5-methyl-5,6-dihydro-2H-[1,4]oxazin-3-ylamine hydrochloride,
[3-((R)-5-Amino-3-methyl-3,6-dihydro-2H-[1,4]oxazin-3-yl)-4-fluoro-phenyl]-(3-chloro-quinolin-8-yl)-amine hydrochloride,
[3-((R)-5-Amino-3-methyl-3,6-dihydro-2H-[1,4]oxazin-3-yl)-4-fluoro-phenyl]-(3,6-dichloro-quinolin-8-yl)-amine hydrochloride,
[3-((R)-5-Amino-3-methyl-3,6-dihydro-2H-[1,4]oxazin-3-yl)-4-fluoro-phenyl]-(3-chloro-6-fluoro-quinolin-8-yl)-amine hydrochloride,
[3-((R)-5-Amino-3-methyl-3,6-dihydro-2H-[1,4]oxazin-3-yl)-4-fluoro-phenyl]-(3-difluoromethoxy-quinolin-8-yl)-amine hydrochloride,
[3-((R)-5-Amino-3-methyl-3,6-dihydro-2H-[1,4]oxazin-3-yl)-4-fluoro-phenyl]-[3-(2-fluoro-ethoxy)-quinolin-8-yl]-amine hydrochloride,
[3-((R)-5-Amino-3-methyl-3,6-dihydro-2H-[1,4]oxazin-3-yl)-4-fluoro-phenyl]-(3-cyclopropylmethoxy-6-fluoro-quinolin-8-yl)-amine hydrochloride,
[3-((R)-5-Amino-3-methyl-3,6-dihydro-2H-[1,4]oxazin-3-yl)-4-fluoro-phenyl]-[3-(2,2,2-trifluoro-ethoxy)-quinolin-8-yl]-amine hydrochloride,
[3-((R)-5-Amino-3-methyl-3,6-dihydro-2H-[1,4]oxazin-3-yl)-4-fluoro-phenyl]-(3-chloro-6,7-dihydro-5H-[1]pyridin-7-yl)-amine,
[3-(5-Amino-3-methyl-3,6-dihydro-2H-[1,4]oxazin-3-yl)-phenyl]-(1,2-dimethyl-1H-benzoimidazol-5-yl)-amine,

[3-(5-Amino-3-methyl-3,6-dihydro-2H-[1,4]oxazin-3-yl)-phenyl]-(2-cyclopropyl-benzooxazol-4-yl)-amine hydrochloride,
[3-(5-Amino-3-methyl-3,6-dihydro-2H-[1,4]oxazin-3-yl)-phenyl]-(3-chloro-quinolin-8-yl)-amine hydrochloride,
[3-(5-Amino-3-methyl-3,6-dihydro-2H-[1,4]oxazin-3-yl)-phenyl]-(3-chloro-6-fluoro-quinolin-8-yl)-amine hydrochloride,
[3-(5-Amino-3-methyl-3,6-dihydro-2H-[1,4]oxazin-3-yl)-phenyl]-(3-methoxy-quinolin-8-yl)-amine hydrochloride,
[3-(5-Amino-3-methyl-3,6-dihydro-2H-[1,4]oxazin-3-yl)-phenyl]-quinolin-8-yl-amine hydrochloride,
5-[3-(2,4-Dichloro-benzylamino)-phenyl]-5-methyl-5,6-dihydro-2H-[1,4]oxazin-3-ylamine,
5-[3-(2-Difluoromethoxy-phenylamino)-phenyl]-5-methyl-5,6-dihydro-2H-[1,4]oxazin-3-ylamine hydrochloride,
5-[3-(4-Chloro-benzylamino)-phenyl]-5-methyl-5,6-dihydro-2H-[1,4]oxazin-3-ylamine,
5-[3-(5-Chloro-indan-1-ylamino)-phenyl]-5-methyl-5,6-dihydro-2H-[1,4]oxazin-3-ylamine hydrochloride, and
5-{3-[1-(4-Chloro-phenyl)-ethylamino]-phenyl}-5-methyl-5,6-dihydro-2H-[1,4]oxazin-3-ylamine.

A certain embodiment of the invention provides a process to synthesize a compound of formula I as described herein, which process comprises deprotecting a compound of formula XVI.

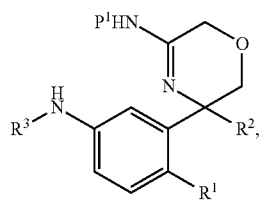

XVI wherein $R^1$, $R^2$ and $R^3$ are as herein described and $P^1$ is an amino-protecting group as herein described, in particular a tert-butoxycarbonyl group, a bis(dimethoxyphenyl)-phenyl-methyl or dimethoxytrityl group.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes, particularly type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition containing a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes, particularly type 2 diabetes.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes, particularly type 2 diabetes.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Particular examples of isomers of a compound of formula I is a compound of formula Ia or a compound of formula Ib, wherein the residues have the meaning as described in any of the embodiments. Most particular is a compound of formula Ib.

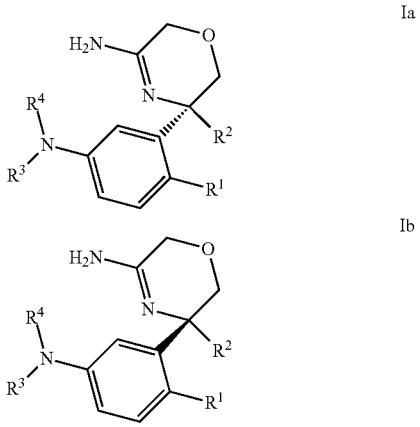

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

The compounds of formula I can be prepared through a number of synthetic routes for example as illustrated in schemes 1-4. The preparation of compounds of formula I of the present invention can be carried out in sequential or convergent synthetic routes. Syntheses of the compounds of the invention are shown in the following schemes 1-4. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of formula I described in the schemes 1-4 can be isolated and purified by methods known to those skilled in the art, such as but not limited to ion exchange chromatography, solid phase extraction, liquid-liquid extraction, silica chromatography, crystallization and preparative HPLC.

According to scheme 1, ketones of general formula IV (wherein Y has the meaning of a leaving group like halogen, e.g. bromo) can be reacted with cyanides, like potassium cyanide, together with ammonium carbonate in polar solvents such as alcohols, e.g. ethanol, water or tetrahydrofuran and mixtures thereof, to form hydantoins of formula V. The hydantoin can then be treated with water along with a base such as sodium hydroxide or a strong acid such as sulfuric acid at temperatures ranging from ambient temperature to reflux to yield the amino acid of formula VI. The amino alcohol of formula VIII is obtained by esterification of the acid of formula VI with a lower alcohol, such as methanol or ethanol, followed by reduction of the resulting amino ester of formula VII with lithium aluminum hydride or other suitable reagents both steps performed under conditions known to those skilled in the art. N-Acylation of the aminoalcohol of formula VIII can be effected by condensation with halogenated acetic acid derivatives, such as chloroacetic acid using condensation reagents like benzotriazole derivatives, e.g. O-(benzotriazol-1-yl)-N,N,N',N'-tetramethyluronium-hexafluorophosphate (HBTU) and the like in inert solvents, or with acid chloride derivatives such as chloroacetyl chloride in presence of a base such as triethylamine in an inert solvent both methods under conditions known to those skilled in the art and yielding acetyl derivatives of formula IX. Lactams of formula X can be prepared by cyclization of the alcohol of formula IX with base, such as potassium tert-butylate, in solvents such as tert-butanol at temperatures ranging from room temperature to reflux. The iminoether of formula XI can be synthesized by treatment of the lactam of formula X with alkyl oxonium salts, e.g. trimethyloxonium tetrafluoroborate or triethyloxonium tetrafluoroborate.

Non commercial ketones of general formula IV can be synthesized by routes such as depicted in scheme 1 or by other routes known to those skilled in the art. Weinreb amides of formula III can be obtained by standard condensation reactions of the acids of formula II with N,O-dimethylhydroxylamine or by the intermediate formation of the acyl chloride of acids of formula II using an agent such as oxalyl chloride or thionyl chloride using standard conditions such as triethylamine/dichloromethane. The amides of formula III can be reacted with organometallics such as methylmagnesium chloride in inert aprotic solvents such as tetrahydrofuran or diethyl ether to yield the desired ketones of formula IV.

Scheme 1: Syntheses of compounds of formula I

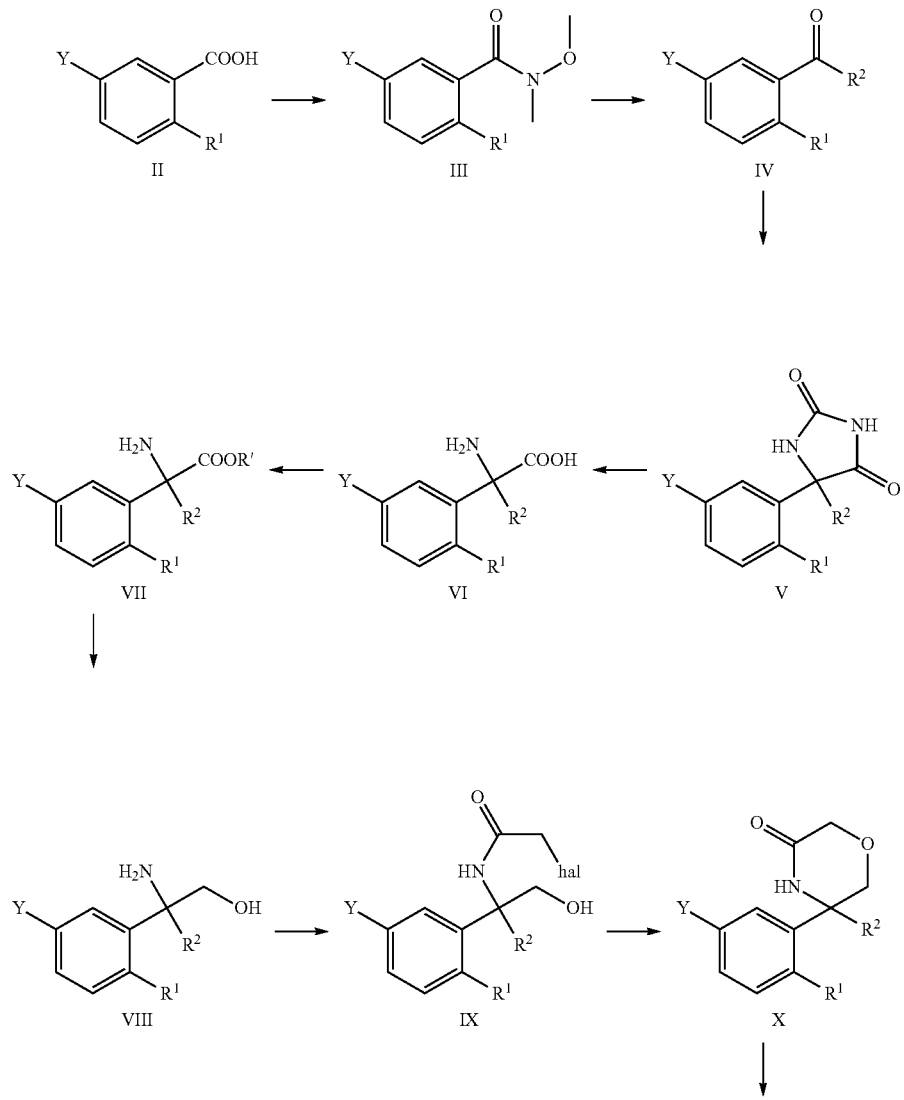

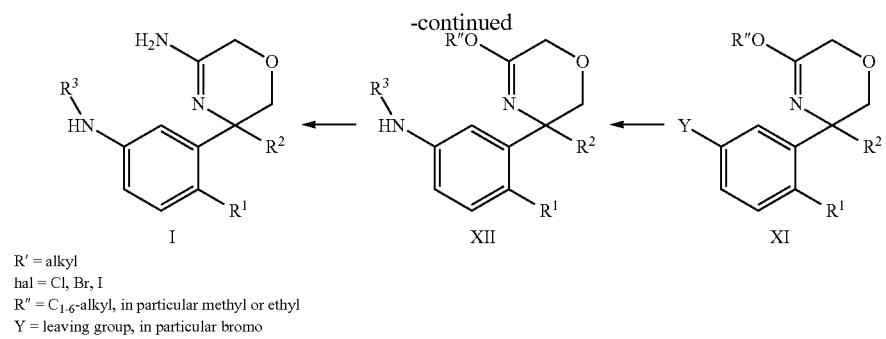

R' = alkyl
hal = Cl, Br, I
R'' = C$_{1-6}$-alkyl, in particular methyl or ethyl
Y = leaving group, in particular bromo For the further transformation to the aniline derivative of formula XII, Pd(0)-catalyzed amination reactions with amines of formula R$^3$—NH$_2$ can be applied. Treatment of the iminoether of formula XII with ammonium salts such as ammonium chloride in polar solvents like alcohols, e.g. methanol, yields the final compound of formula I.

salts such as ammonium chloride in polar solvents like alcohols, e.g. methanol. The protection of the amidine of formula XIV can be accomplished with a protecting group P$^1$, e.g. tert-butoxycarbonyl group or with a triphenylmethyl protecting group, particularly 4,4'-dimethoxytrityl and a base, e.g. an alkyl amine, particularly triethylamine in an inert solvent Scheme 2: Syntheses of compounds of formula I

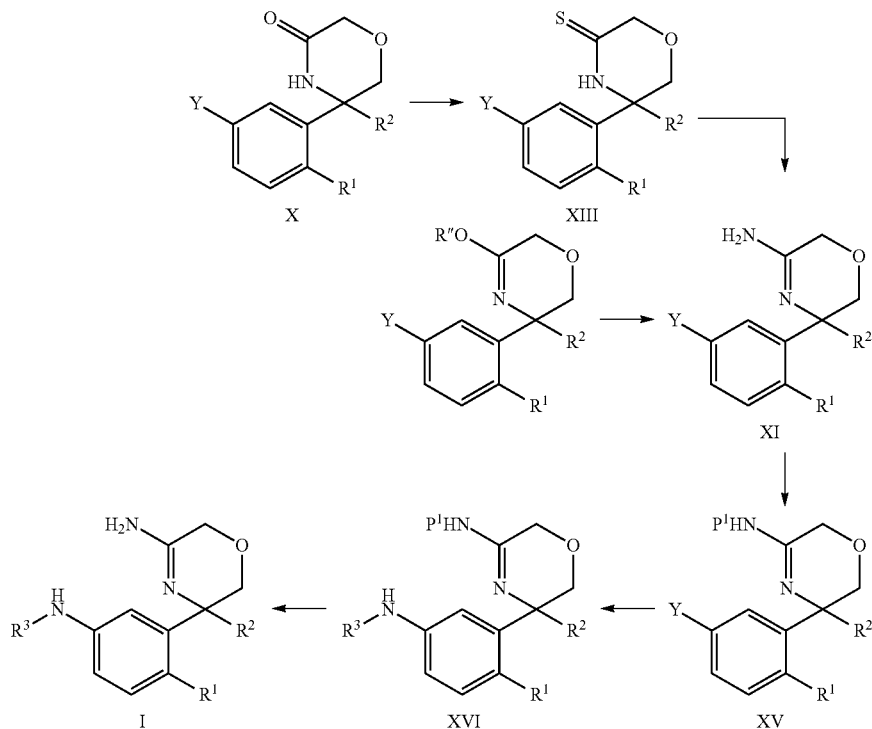

R'' = C$_{1-6}$-alkyl, in particular methyl or ethyl
Y = leaving group, in particular bromo
P$^1$ = amino protecting group, in particular tert-butoxycarbonyl Alternatively, compounds of formula I can be obtained as follows: According to scheme 2, treatment of compounds of formula X with Lawesson's reagent under conditions known to those skilled in the art yields the thiolactam of formula XIII. Further treatment of the thiolactam of formula XIII either with oxidizing reagents like tert-butyl hydroperoxide followed by ammonolysis or by treatment with ammonia in methanol alone yields the intermediate amidine of formula XIV. Intermediates of formula XIV can also be obtained by treatment of the iminoether of formula XI with ammonium such as dichloromethane. For the further transformation to the aniline derivative of formula XVI, metal-catalyzed amination reactions, particularly Pd(0)-catalyzed reactions with amines of formula R$^3$—NH$_2$ can be applied. Deprotection of the amino groups in compounds of formula XVI to yield compounds of formula I can be achieved by reaction with a strong organic acid, such as trifluoroacetic acid, in chlorinated solvents, such as dichloromethane or chloroform, under anhydrous conditions at temperatures between 0° C. and ambient temperature.

Furthermore, compounds of formula I can be obtained as follows: According to scheme 3, the formation of a methyltriphenyl-phosphonium ylide produced by strong base such as butyllithium in solvents such as tetrahydrofuran or toluene at temperatures between −78° C. and 0° C. followed by addition of a ketone of formula IV yields the alkenes of formula XVII. These can then be reacted with a mixture of silver cyanate and iodine in solvents such as diethyl ether or mixtures of ethyl acetate and acetonitrile. The resultant iodoisocyanates of formula XVIII can then be heated with alcohols like tert-butanol and a base like triethylamine or Huenig's base to yield the oxazolidinones of formula XIX. Hydrolysis of the resultant oxazolidinone of formula XIX with aqueous base like lithium hydroxide yields the aminoalcohol of formula VIII.

Scheme 4: Alternative synthesis of intermediate XX.

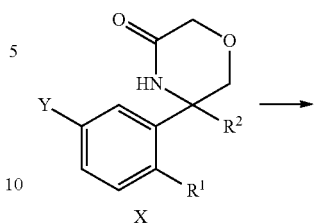

Scheme3: Syntheses of compounds of formula I

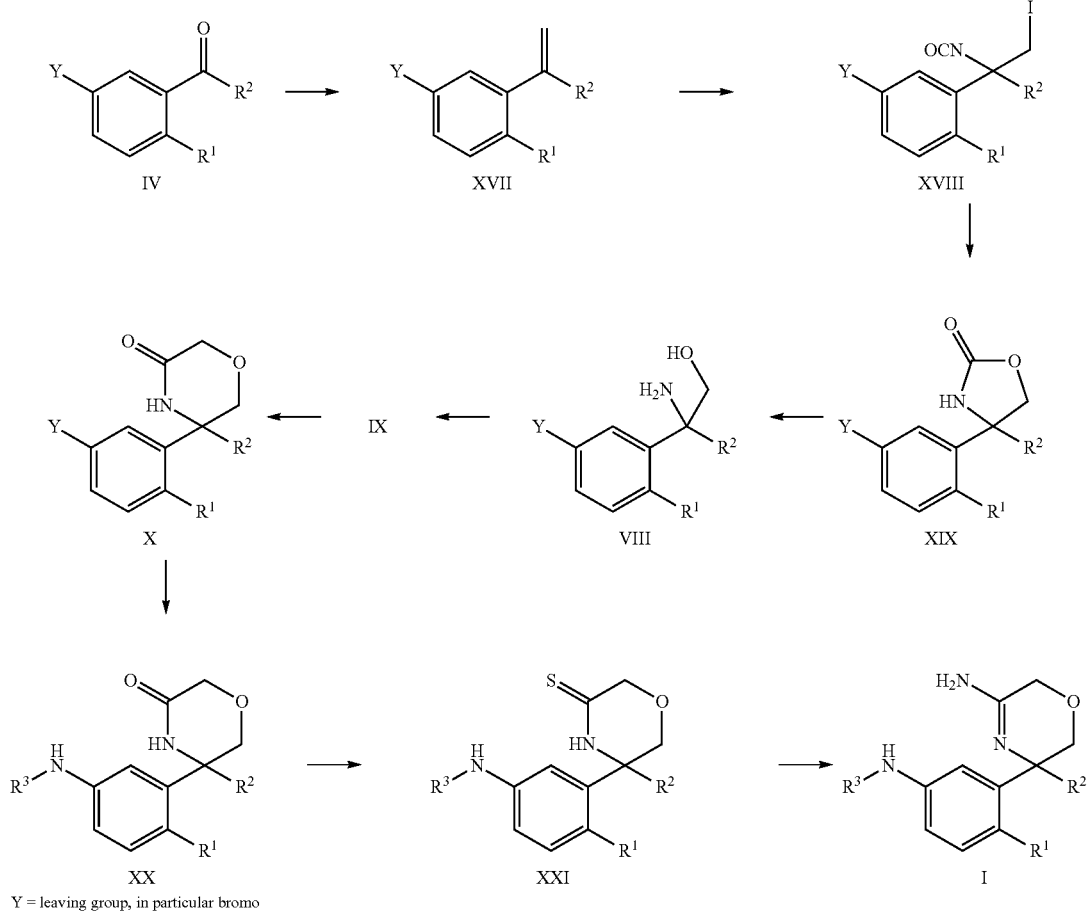

Y = leaving group, in particular bromo

As already described before, N-acylation of the aminoalcohol of formula VIII and cyclization of the resulting compounds of formula IX yield the lactams of formula X. Transformation to the aniline derivatives of formula XX can be accomplished by metal-catalyzed amination reactions, particularly Pd(0)-catalyzed reactions with amines of formula $R^3$—$NH_2$. Reaction of compounds of formula XX with Lawesson's reagent under conditions known to those skilled in the art yields the thiolactams of formula XXI. Further treatment of the thiolactam of formula XXI either with oxidizing reagents like tert-butyl hydroperoxide followed by ammonolysis or by treatment with ammonia in methanol alone yields the final amidine of formula I.

-continued

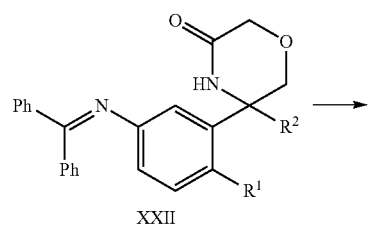

XXII

-continued

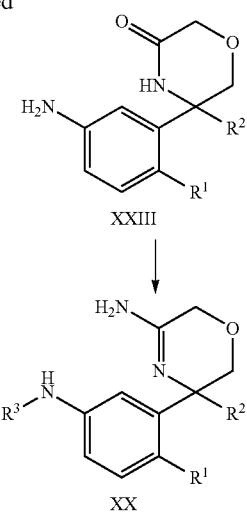

Y = leaving group, in particular bromo

Alternatively, compounds of formula XX are obtained as follows (Scheme 4): Reaction of lactams of formula X with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-phos), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C. yield the intermediate imine of formula XXII. Also the reaction of lactams of formula X with lithium hexamethyldisilazide in the presence of a suitable transition metal catalyst and a suitable ligand, such mentioned above following a protocol as for example described by J. F. Hartwing et al. in Organic Letters 3(17), 2729-32 (2001) can result in an imine of formula XXII.

Cleavage of the benzophenone imine in compounds of formula XXII can be achieved under acidic conditions, e.g. with hydrochloric acid at ambient temperature to produce the anilines of formula XXIII.

Amines of formula XX can be prepared by reductive amination of anilines of formula XXIII with a reducing agent, e.g. sodium borohydride, particularly sodium triacetoxyborohydride, or decaborane and a weak acid, e.g. acetic acid, in a solvent such as tetrahydrofuran or dichloromethane.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% CO$_2$ in a humidified incubator the culture supernatant was harvested for the determination of Aβ340 concentrations. 96well ELISA plates (e.g., Nunc MaxiSorb) were coated with monoclonal antibody which specifically recognize the C-terminal end of Aβ340 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/H$_2$O$_2$ in citric acid buffer. After stopping the reaction with one volume 1 N H$_2$SO$_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640 +Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown in adherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

$IC_{50}$ values of selected examples

| Exam. | Structure | BACE1 cell act. Aβ40 $IC_{50}$ [µM] | BACE2 cell act. $IC_{50}$ [µM] |
|---|---|---|---|
| 1 | 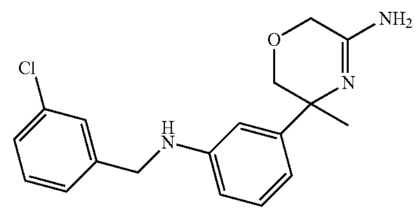 [SMILES: CC1(c2cccc(NCc3cccc(Cl)c3)c2)COCC(N)=N1] | — | — |
| 2 | 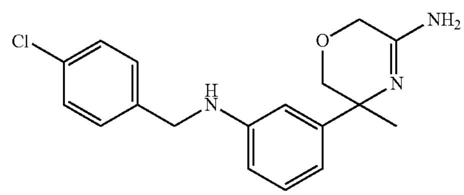 [SMILES: CC1(c2cccc(NCc3ccc(Cl)cc3)c2)COCC(N)=N1] | 0.450 | — |
| 3 | 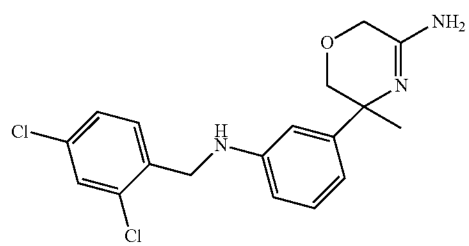 [SMILES: CC1(c2cccc(NCc3ccc(Cl)cc3Cl)c2)COCC(N)=N1] | | |
| 4 | 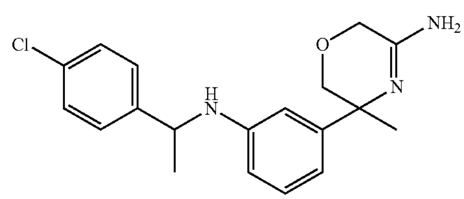 [SMILES: CC(Nc1cccc(C2(C)COCC(N)=N2)c1)c1ccc(Cl)cc1] | | |
| 5 | 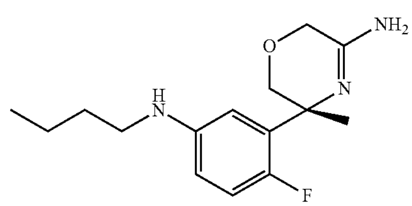 [SMILES: CCCCNc1ccc(F)c([C@]2(C)COCC(N)=N2)c1] | 0.340 | — |
| 6 | 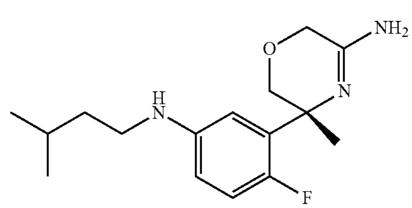 [SMILES: CC(C)CCNc1ccc(F)c([C@]2(C)COCC(N)=N2)c1] | 1.360 | 0.605 |

TABLE 1-continued

IC$_{50}$ values of selected examples

| Exam. | Structure | BACE1 cell act. Aβ40 IC$_{50}$ [µM] | BACE2 cell act. IC$_{50}$ [µM] |
|---|---|---|---|
| 7 | 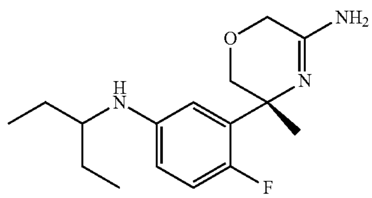 [SMILES: CCC(CC)Nc1ccc(F)c([C@]2(C)COCC(N)=N2)c1] | | |
| 8 | 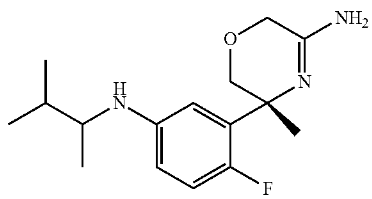 [SMILES: CC(C)C(C)Nc1ccc(F)c([C@]2(C)COCC(N)=N2)c1] | 2.190 | — |
| 9 | 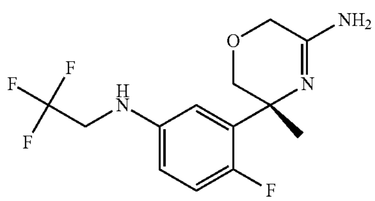 [SMILES: C[C@@]1(c2cc(NCC(F)(F)F)ccc2F)COCC(N)=N1] | 0.350 | — |
| 10 | 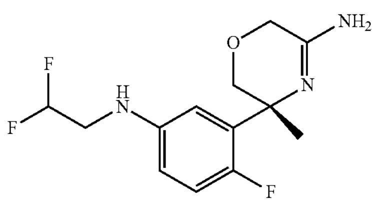 [SMILES: C[C@@]1(c2cc(NCC(F)F)ccc2F)COCC(N)=N1] | 0.410 | — |
| 11 | 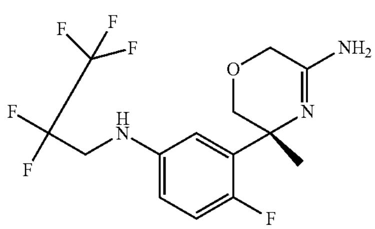 [SMILES: C[C@@]1(c2cc(NCC(F)(F)CC(F)(F)F)ccc2F)COCC(N)=N1] | | |
| 12 | 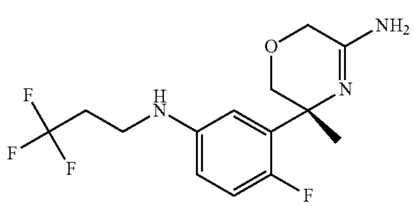 [SMILES: C[C@@]1(c2cc(NCCC(F)(F)F)ccc2F)COCC(N)=N1] | 1.090 | 2.900 |
| 13 | 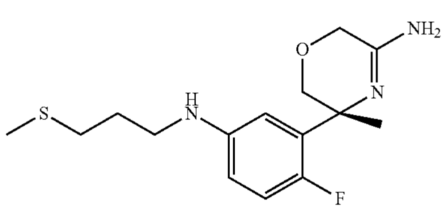 [SMILES: CSCCCNc1ccc(F)c([C@]2(C)COCC(N)=N2)c1] | 0.310 | — |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 14 | 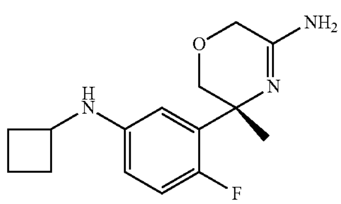 [SMILES: C[C@@]1(c2cc(NC3CCC3)ccc2F)COCC(N)=N1] | 0.260 | 1.170 |
| 15 | 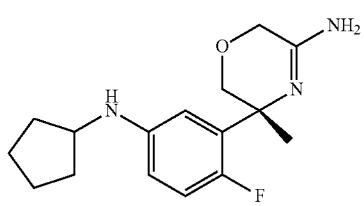 [SMILES: C[C@@]1(c2cc(NC3CCCC3)ccc2F)COCC(N)=N1] | 0.120 | 0.170 |
| 16 | 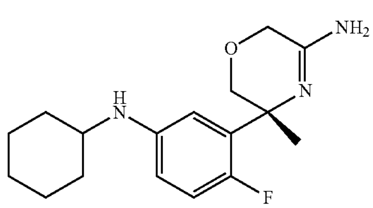 [SMILES: C[C@@]1(c2cc(NC3CCCCC3)ccc2F)COCC(N)=N1] | | |
| 17 | 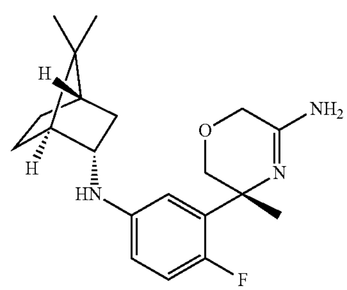 [SMILES: CC1(C)C[C@@H]2CC[C@H]1C[C@@H]2Nc1ccc(F)c([C@]2(C)COCC(N)=N2)c1] | | |
| 18 | 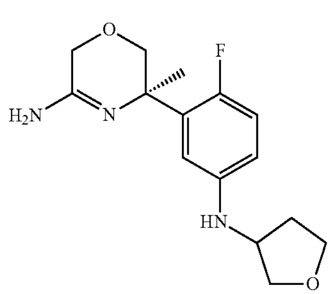 [SMILES: C[C@@]1(c2cc(NC3CCOC3)ccc2F)COCC(N)=N1] | 0.320 | 3.391 |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 19 | 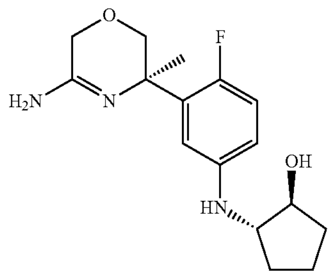 [SMILES: C[C@@]1(c2cc(N[C@H]3CCC[C@@H]3O)ccc2F)COCC(N)=N1] | 1.210 | 3.419 |
| 20 | 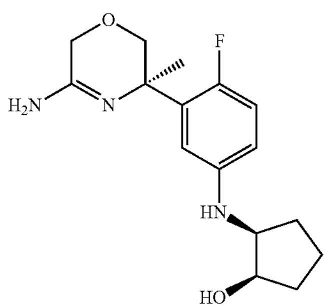 [SMILES: C[C@@]1(c2cc(N[C@H]3CCC[C@H]3O)ccc2F)COCC(N)=N1] | 0.610 | 2.270 |
| 21 | 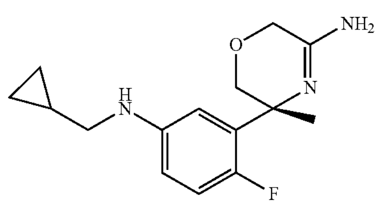 [SMILES: C[C@@]1(c2cc(NCC3CC3)ccc2F)COCC(N)=N1] | 0.130 | 0.279 |
| 22 | 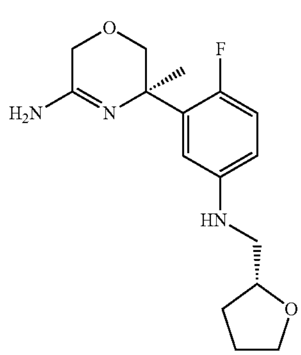 [SMILES: C[C@@]1(c2cc(NC[C@H]3CCCO3)ccc2F)COCC(N)=N1] | 1.110 | 2.430 |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 23 | 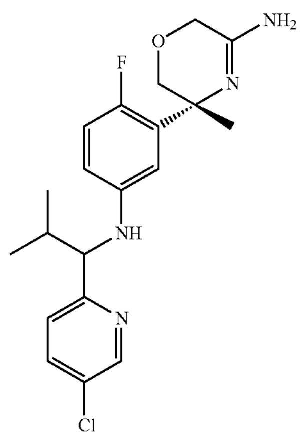 [SMILES: CC(C)C(Nc1ccc(F)c([C@]2(C)COCC(N)=N2)c1)c1ccc(Cl)cn1] | 3.710 | 1.662 |
| 24 | 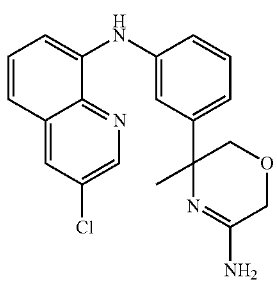 [SMILES: CC1(c2cccc(Nc3cccc4cc(Cl)cnc34)c2)COCC(N)=N1] | 0.250 | 0.018 |
| 25 | 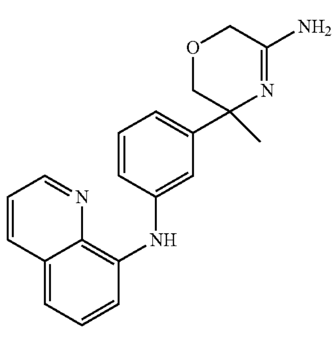 [SMILES: CC1(c2cccc(Nc3cccc4cccnc34)c2)COCC(N)=N1] | | |
| 26 | 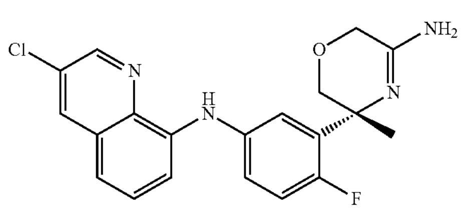 [SMILES: C[C@@]1(c2cc(Nc3cccc4cc(Cl)cnc34)ccc2F)COCC(N)=N1] | 0.160 | 0.077 |

TABLE 1-continued
IC$_{50}$ values of selected examples
| Exam. | Structure | BACE1 cell act. Aβ40 IC$_{50}$ [μM] | BACE2 cell act. IC$_{50}$ [μM] |
|---|---|---|---|
| 27 | 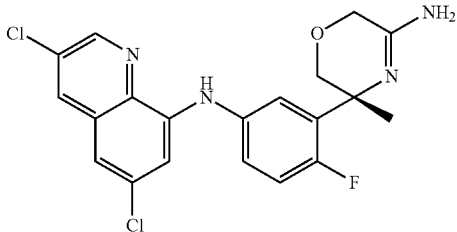 [SMILES: C[C@@]1(c2cc(Nc3cc(Cl)cc4cc(Cl)cnc34)ccc2F)COCC(N)=N1] | 0.660 | 0.558 |
| 28 | 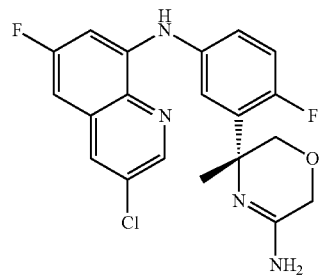 [SMILES: C[C@@]1(c2cc(Nc3cc(F)cc4cc(Cl)cnc34)ccc2F)COCC(N)=N1] | 0.044 | — |
| 29 | 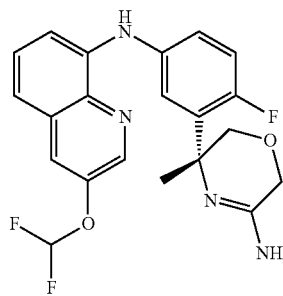 | 0.270 | 2.296 |
| 30 | 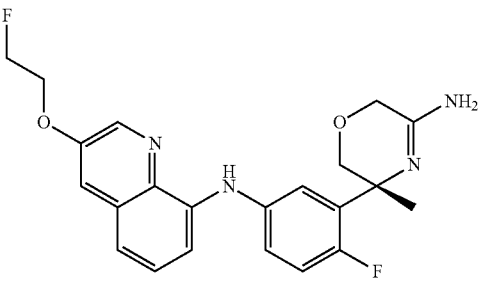 [SMILES: C[C@@]1(c2cc(Nc3cccc4cc(OCCF)cnc34)ccc2F)COCC(N)=N1] | 4.770 | — |
| 31 | 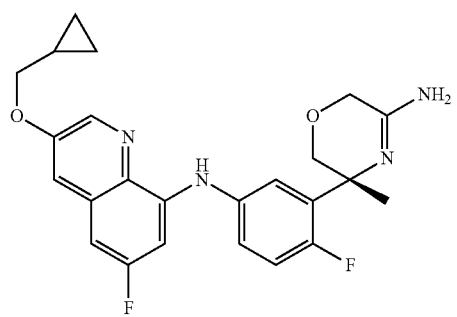 [SMILES: C[C@@]1(c2cc(Nc3cc(F)cc4cc(OCC5CC5)cnc34)ccc2F)COCC(N)=N1] | 6.900 | — |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 32 | 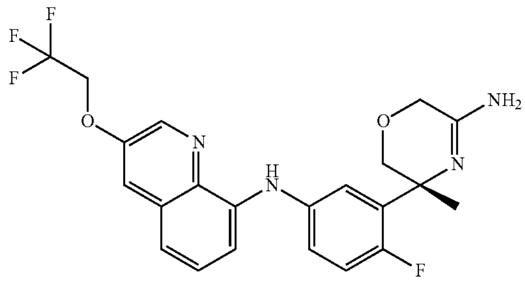 [SMILES: C[C@@]1(c2cc(Nc3cccc4cc(OCC(F)(F)F)cnc34)ccc2F)COCC(N)=N1] | 2.360 | — |
| 33 | 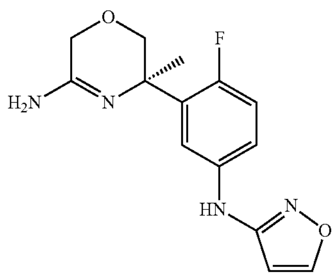 [SMILES: C[C@@]1(c2cc(Nc3ccon3)ccc2F)COCC(N)=N1] | 0.580 | 1.210 |
| 34 | 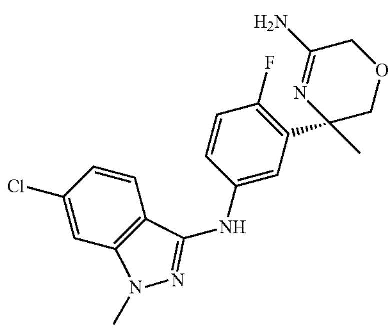 [SMILES: Cn1nc(Nc2ccc(F)c([C@@]3(C)COCC(N)=N3)c2)c2ccc(Cl)cc21] | 1.040 | 1.481 |
| 35 | 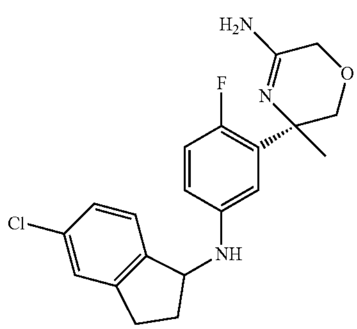 [SMILES: C[C@]1(c2cc(NC3CCc4cc(Cl)ccc43)ccc2F)COCC(N)=N1] | 0.100 | 0.732 |
| 36 | 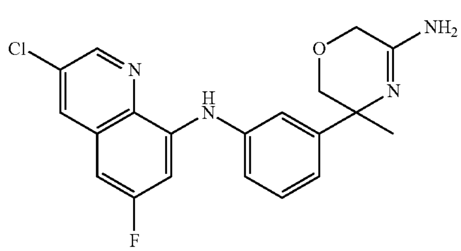 [SMILES: CC1(c2cccc(Nc3cc(F)cc4cc(Cl)cnc34)c2)COCC(N)=N1] | 0.250 | — |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 37 | 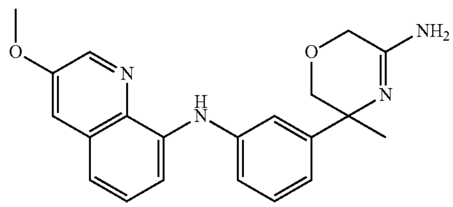 [SMILES: COc1cnc2c(Nc3cccc(C4(C)COCC(N)=N4)c3)cccc2c1] | — | 0.120 |
| 38 | 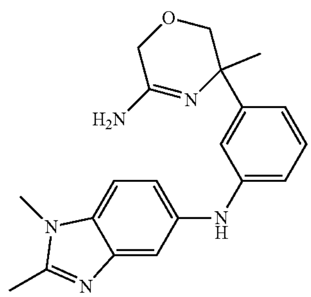 [SMILES: Cc1nc2cc(Nc3cccc(C4(C)COCC(N)=N4)c3)ccc2n1C] | | |
| 39 | 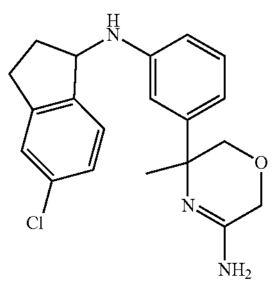 [SMILES: CC1(c2cccc(NC3CCc4cc(Cl)ccc43)c2)COCC(N)=N1] | 0.180 | — |
| 40 | 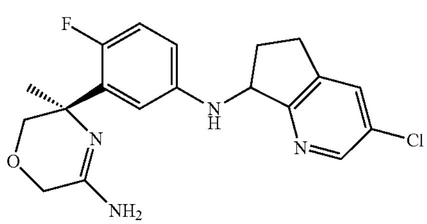 [SMILES: C[C@@]1(c2cc(NC3CCc4cc(Cl)cnc43)ccc2F)COCC(N)=N1] | 0.320 | 1.097 |
| 41 | 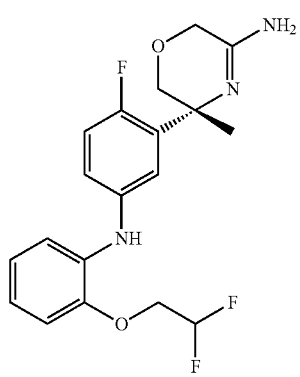 [SMILES: C[C@@]1(c2cc(Nc3ccccc3OCC(F)F)ccc2F)COCC(N)=N1] | 2.140 | 0.010 |

TABLE 1-continued
IC$_{50}$ values of selected examples
| Exam. | Structure | BACE1 cell act. Aβ40 IC$_{50}$ [μM] | BACE2 cell act. IC$_{50}$ [μM] |
|---|---|---|---|
| 42 | 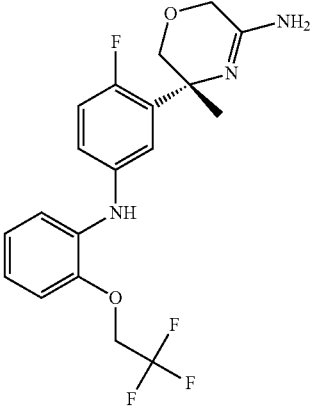 [SMILES: C[C@@]1(c2cc(Nc3ccccc3OCC(F)(F)F)ccc2F)COCC(N)=N1] | 5.200 | — |
| 43 | 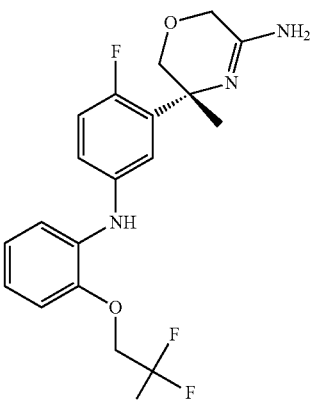 | 3.200 | — |
| 44 | 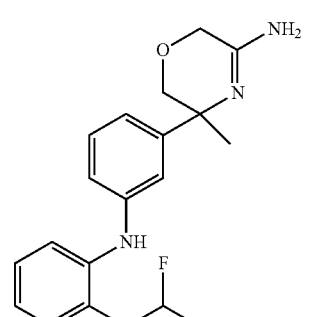 | 0.890 | — |
| 45 | 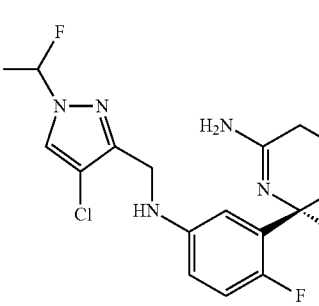 | 0.017 | — |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 46 | (structure) | — | 0.300 |

CYP Inhibition Assay

Inhibition of cytochromes P450 (CYPs) 2C9, 2D6 and 3A4 was assessed using human liver microsomes and CYP-selective substrate metabolism reactions. 50 μl incubations were made up containing (finally) 0.2 mg/ml pooled human liver microsomes, 5 μM substrate (diclofenac for CYP2C9 [4' hydroxylase], dextromethorphan for CYP2D6 [O-demethylase] or midazolam for CYP3A4 [1' hydroxylase]), 0.25 μl, DMSO containing test inhibitor and NADPH regenerating system. Test inhibitor concentrations of 50, 16.7, 5.6, 1.9, 0.6 and 0.2 μM were assessed in singlicate. Incubations were prewarmed to 37° C. for 10 minutes before initiation by addition of NADPH regenerating system. Incubations were quenched after 5 minutes (20 minutes for dextromethorphan) by addition of 50 μl cold acetonitrile containing 20 ng/ml 4-OH-diclofenac-13C6, 20 ng/mL dextrorphan-D3 and 20 ng/mL 1-OH-midazolam-D4. Quenched incubates were stored at −20° C. for at least 1 hour before centrifugation (20,000×g, 20 minutes). Supernatants were removed and diluted 1:1 with water prior to analysis using a RapidFire sample injector system and API4000 mass spectrometer. Peak areas for substrate, metabolite and stable-labelled metabolite standard were determined using MS/MS. The peak area ratios between the metabolite generated by the enzymatic reaction and the internal standard were used in subsequent calculations. The percentage of (DMSO) control activity was calculated for each incubate and IC$_{50}$ values estimated by non-linear regression. Sulfaphenazole, quinidine or ketoconazole were tested in each CYP2C9, CYP2D6 or CYP3A4 inhibition experiment, respectively, to ensure assay sensitivity and reproducibility. (Validated assays for human cytochrome P450 activities, R. L. Walsky and R. S. Obach, Drug Metabolism and Disposition 32: 647-660, 2004. and S. Fowler and H. Zhang, The AAPS Journal, Vol. 10, No. 2, 410-424, 2008.)

| Ex. | CYP IC$_{50}$ [μM][5) | | |
|---|---|---|---|
| | 3A4 | 2D6 | 2C9 |
| 27 | 33 | 4.5 | >50 |
| 34 | 25 | 2.0 | 6.7 |

Cathepsin D and Cathepsin E Fluorescent Substrate Kinetic Assays

General Assay Principle

The MR121 fluorescence assays described below are based on the fact that MR121 forms a non-fluorescent ground state complex with tryptophan. In solution this formation occurs at millimolar concentrations of tryptophan. The mechanism can be used to design a generic biochemical assay for proteases. A substrate peptide is labeled at the N-terminus with tryptophan and at the C-terminus with the fluorophore MR121 (for cathepsin D the 10 amino acid peptide WTSVLMAAPC-MR121 was used; for cathepsin E, MR121-CKLVFFAEDW was used). In absence of protease activity, the substrates remain intact and the MR121 fluorescence is reduced by the high local Trp-concentration. If the substrates are cleaved by the enzymes the MR121 fluorescence is recovered.

Assay Procedure

The fluorescent substrate cathepsin D and cathepsin E kinetic assays were performed at room temperature in 384-well microtiter plates (black with clear flat bottom, non binding surface plates from Corning) in a final volume of 51 μl. The test compounds were serially diluted in DMSO (15 concentrations, ⅓ dilution steps) and 1 μl of diluted compounds were mixed for 10 min with 40 μl of cathepsin D (from human liver, Calbiochem) diluted in assay buffer (100 mM sodium acetate, 0.05% BSA, pH 5.5; final concentration: 200 nM) or with 40 μl of recombinant human cathepsin E (R&D Systems) diluted in assay buffer (100 mM sodium acetate, 0.05% BSA, pH 4.5; final concentration: 0.01 nM). After addition of 10 μl of the cathepsin D substrate WTSVLMAAPC-MR121 diluted in cathepsin D assay buffer (final concentration: 300 nM) or 10 μl of the cathepsin E substrate MR121-CKLVFFAEDW diluted in cathepsin E assay buffer (final concentration: 300 nM), the plates were strongly shaken for 2 minutes. The enzymatic reaction was followed in a plate: vision reader (Perkin Elmer) (excitation wavelength: 630 nm; emission: 695 nm) for at least 30 minutes in a kinetic measurement detecting an increase of MR121 fluorescence during the reaction time. The slope in the linear range of the kinetic was calculated and the IC$_{50}$ of the test compounds were determined using a four parameter equation for curve fitting.

| Ex. | Cathepsin E IC$_{50}$ [μM] | Cathepsin D IC$_{50}$ [μM] |
|---|---|---|
| 29 | 17.6 | 21.1 |
| 36 | 5.0 | 2.6 |

Pharmaceutical Compositions

The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also encompassed by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical compositions conveniently contain about 1-500 mg, particularly 1-100 mg, of a compound of formula I. Examples of compositions according to the invention are:

EXAMPLE A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the Following Composition are Manufactured:

TABLE 6

| possible suppository composition | |
|---|---|
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection Solutions of the Following Composition are Manufactured:

TABLE 7

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the Following Composition are Manufactured:

TABLE 8

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Preparation of Building Block A (RS)-5-(3-Bromo-phenyl)-5-methyl-morpholin-3-one

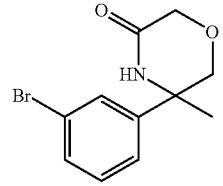

a) (RS)-5-(3-Bromo-phenyl)-5-methyl-imidazolidine-2,4-dione

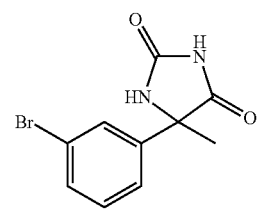

A mixture of 3-bromo-acetophenone (10.0 g, 50 mmol), potassium cyanide (4.96 g, 75 mmol), and ammonium carbonate (33.45 g, 348 mmol) in ethanol (65 ml) was heated in an autoclave at 120° C. for 16 h. For the workup, the reaction mixture was cooled to room temperature, then treated with water (250 ml) and ethyl acetate (500 ml). The aqueous layer was separated and re-extracted with ethyl acetate (250 ml). The combined organic layers were washed twice with saturated sodium chloride solution (2×250 ml), thereafter dried over sodium sulphate, and evaporated at reduced pressure. 13.2 g (98.6%) of (RS)-5-(3-bromo-phenyl)-5-methyl-imidazolidine-2,4-dione were obtained as a white solid. The purity of the product allowed using it in the next step without further purification. Mass (calculated) $C_{10}H_9BrN_2O_2$ [269.099]; (found) $[M-H]^-=267, 269$.

b) (RS)-2-Amino-2-(3-bromo-phenyl)-propionic acid methyl ester

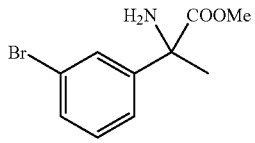

A dispersion of (RS)-2-amino-2-(3-bromo-phenyl)-propionic acid methyl ester (12.81 g, 48 mmol) in 6 N sodium hydroxide solution (95.23 ml) was heated to reflux for 48 h. For the workup, the reaction mixture was cooled with ice and treated with hydrochloric acid (36.5%) until pH 1 was reached. The mixture was evaporated to dryness at reduced pressure. The crude (RS)-2-amino-2-(3-bromo-phenyl)-propionic acid hydrochloride was dispersed in methanol (500 ml) and cooled to 0° C. Within 12 minutes and under ice cooling, thionylchloride (18.02 ml, 246 mmol) was added dropwise. After complete addition, the reaction mixture was heated to reflux for 60 h. For the workup, the reaction mixture was cooled to room temperature and evaporated at reduced pressure. The white residue was treated with a mixture of water and ice (200 ml), triethylamine (16.5 ml), and diethylether (500 ml). The resulting suspension was filtrated over Dicalit, thereafter the aqueous layer was separated and re-extracted with diethylether (250 ml). The combined organic layers were washed with saturated sodium chloride solution (250 ml), dried over sodium sulphate, and evaporated at reduced pressure. 9.39 g (76.7%) of (RS)-2-amino-2-(3-bromo-phenyl)-propionic acid methyl ester were obtained as a light yellow oil. The purity of the product allowed using it in the next step without further purification. Mass (calculated) $C_{10}H_{12}BrNO_2$ [258.117]; (found) $[M+H]^+=258, 260$.

c) (RS)-2-Amino-2-(3-bromo-phenyl)-propan-1-ol

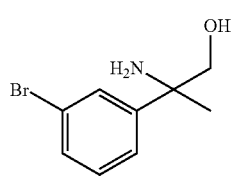

A solution of the (RS)-2-amino-2-(3-bromo-phenyl)-propionic acid methyl ester (9.39 g, mmol) in tetrahydrofuran (360 ml) was treated portionwise at −5° C. with lithiumaluminiumhydride (1.41 g, 36 mmol; 282 mg/2 min). After complete addition, stirring was continued at 0-5° C. for 30 minutes. For the workup, the reaction mixture was cooled to −7° C., and water (9 ml) was added dropwise. Thereafter, 2 N sodium hydroxy solution (9 ml) was added and stirring continued for 15 minutes at room temperature. They grey suspension was filtrated through Dicalite® which was washed with tetrahydrofuran (200 ml). The filtrate was evaporated at reduced pressure. 8.67 g of crude (RS)-2-amino-2-(3-bromo-phenyl)-propan-1-ol were obtained as a colorless oil. The purity of the product allowed using it in the next step without further purification. Mass (calculated) $C_9H_{12}BrNO$ [230.106]; (found) $[M+H]^+=230, 232$.

d) (RS)-N-[1-(3-Bromo-phenyl)-2-hydroxy-1-methyl-ethyl]-2-chloro-acetamide

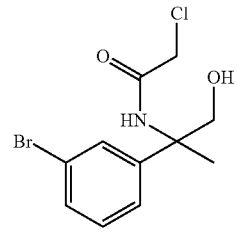 [SMILES: CC(CO)(NC(=O)CCl)c1cccc(Br)c1]

A solution of crude (RS)-2-amino-2-(3-bromo-phenyl)-propan-1-ol (8.38 g, 36 mmol) and triethylamine (6.08 ml, 44 mmol) in acetonitrile (140 ml) was treated dropwise at −2° C. with chloroacetylchloride (3.25 ml, 40 mmol). After complete addition, the orange colored solution was left to warm to room temperature and stirring was continued for 2 h. For the workup, to the reaction was added silica gel (10 g) and it was evaporated at reduced pressure, thereafter, it was purified by chromatography on silica gel using a gradient of dichloromethane/methanol=100/0 to 90/10 as the eluent. 9.62 g (86%) of (RS)-N-[1-(3-bromo-phenyl)-2-hydroxy-1-methyl-ethyl]-2-chloro-acetamide were obtained as a light brown oil. Mass (calculated) $C_{11}H_{13}BrClNO_2$ [306.589]; (found) $[M+H]^+=306, 308$.

e) (RS)-5-(3-Bromo-phenyl)-5-methyl-morpholin-3-one

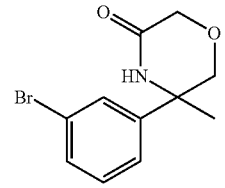

A solution of (RS)-N-[1-(3-bromo-phenyl)-2-hydroxy-1-methyl-ethyl]-2-chloro-acetamide (5.36 g, 17 mmol) in 2-methyl-2-butanol (100 ml) was treated in one portion with potassium tert-butylate (6.66 g, 58 mmol). Initially, the temperature rose to 30° C.; the reaction mixture was left to cool to room temperature and stirring was continued for one hour. For the workup, the reaction mixture was treated with methanol (50 ml), then evaporated at reduced pressure. The residue was purified by chromatography on silica gel using a gradient of dichloromethane/methanol=100/0 to 75/25 as the eluent. 4.18 g (88%) of (RS)-5-(3-bromo-phenyl)-5-methyl-morpholin-3-one were obtained as a white solid. Mass (calculated) $C_{11}H_{12}BrNO_2$ [270.128]; (found) $[M+H]^+=270$ and $[M+2+H]^+=272$.

Preparation of Building Block B (R)-5-(5-Bromo-2-fluoro-phenyl)-5-methyl-morpholin-3-one

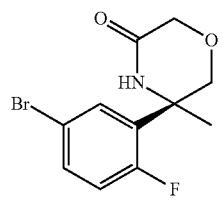 [SMILES: C[C@@]1(c2cc(Br)ccc2F)COCC(=O)N1]

In a reaction sequence analogous to that described for the preparation of Building Block A, (R)-5-(5-bromo-2-fluoro-phenyl)-5-methyl-morpholin-3-one was obtained as follows:

a) 1-(5-Bromo-2-fluoro-phenyl)-ethanone

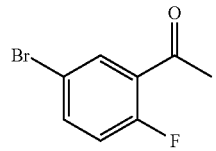

A solution of 5-bromo-2-fluoro-benzoic acid (3.50 g, 16 mmol) in dichloromethane (70 ml) was cooled to 0° C. and treated with triethylamine (1.725 g, 17 mmol), N-(3-dimethylamino-propyl)-N'-ethyl-carbodiimide hydrochloride (3.032 g, 16 mmol), 4-dimethylamino-pyridine (0.097 g, 0.8 mmol), and N,O-dimethyl-hydroxylamine (1.774 g, 18 mmol). The reaction mixture was left to warm to room temperature and stirred for 16 hours. For the workup, the reaction mixture was diluted with dichloromethane (100 ml) and, consecutively, extracted with water (50 ml), citric acid (10%, 50 ml), and saturated sodium hydrogen carbonate solution (50 ml). The organic layer was dried over sodium sulphate, then evaporated. The crude 5-bromo-2-fluoro-N-methoxy-N-methyl-benzamidematerial (3.73 g, 91%) was sufficiently pure and was directly engaged in the next step. In a dried flask, a solution of methylmagnesium chloride (3M in tetrahydrofuran, 5.69 ml, 17 mmol) in tetrahydrofuran (24 ml) was treated at 12-16° C. with a solution of 5-bromo-2-fluoro-N-methoxy-N-methyl-benzamide (3.73 g, 14.2 mmol) in tetrahydrofuran (24 ml). After complete addition, the reaction mixture was heated to reflux. After 20 minutes, the white suspension was quenched under ice cooling with a saturated solution of ammonium chloride (25 ml). After dilution with ethyl acetate (50 ml), the aqueous layer was separated and re-extracted with ethyl acetate (50 ml). The combined organic layers were washed with brine (20 ml), dried over sodium sulphate, and evaporated at reduced pressure. 1-(5-bromo-2-fluoro-phenyl)-ethanone was obtained as a light yellow solid (2.6 g, 84%), which was directly engaged in the next step. $R_f$: 0.55 (silica gel; eluent: heptane/ethyl acetate=4/1).

b) (RS)-5-(5-Bromo-2-fluoro-phenyl)-5-methyl-imidazolidine-2,4-dione

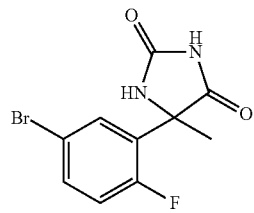

The reaction of 1-(5-bromo-2-fluoro-phenyl)-ethanone with potassium cyanide and ammonium carbonate in ethanol in an autoclave at 120° C. for 16 h yielded the title compound as light yellow solid. Mass (calculated) $C_{10}H_8BrFN_2O_2$ [287.087]; (found) $[M-H]^-=285$ and $[M+2-H]^-=287$.

c) (RS)-2-Amino-2-(5-bromo-2-fluoro-phenyl)-propionic acid methylester

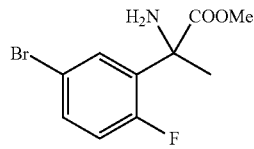

The hydrolysis of the (RS)-5-(5-bromo-2-fluoro-phenyl)-5-methyl-imidazolidine-2,4-dione with 6 N sodium hydroxide solution and esterification of the resulting (RS)-2-amino-2-(5-bromo-2-fluoro-phenyl)-propionic acid with methanol and thionylchloride yielded the (RS)-2-amino-2-(5-bromo-2-fluoro-phenyl)-propionic acid methylester as a light yellow oil. The purity of the product allowed using it in the next step without further purification. Mass (calculated) $C_{10}H_{11}BrFNO_2$ [276.107]; (found) $[M+H]^+=276$ and $[M+2+H]^+=278$.

d) (RS)-2-Amino-2-(5-bromo-2-fluoro-phenyl)-propan-1-ol

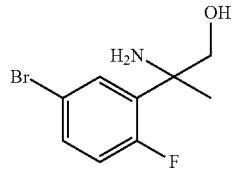

The reduction of the (RS)-2-amino-2-(5-bromo-2-fluoro-phenyl)-propionic acid methylester with lithiumaluminiumhydride in tetrahydrofuran yielded the (RS)-2-amino-2-(5-bromo-2-fluoro-phenyl)-propan-1-ol as a light yellow oil. The purity of the product allowed using it in the next step without further purification. Mass (calculated) C$_9$H$_{11}$BrFNO [248.097]; (found) [M+H]$^+$=248 and [M+2+H]$^+$=250.

e) (RS)-N-[1-(5-Bromo-2-fluoro-phenyl)-2-hydroxy-1-methyl-ethyl]-2-chloro-acetamide

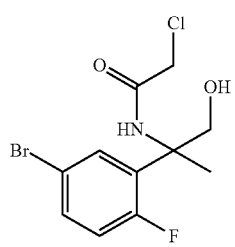 [SMILES: CC(CO)(NC(=O)CCl)c1cc(Br)ccc1F]

The acylation of the (RS)-2-amino-2-(5-bromo-2-fluoro-phenyl)-propan-1-ol with chloroacetylchloride in acetonitrile yielded, after chromatography on silica gel using a gradient of dichloromethane/methanol=100/0 to 80/20 as the eluent, the (RS)-N-[1-(5-bromo-2-fluoro-phenyl)-2-hydroxy-1-methyl-ethyl]-2-chloro-acetamide as a light brown waxy solid. Mass (calculated) C$_{11}$H$_{12}$BrClFNO$_2$ [324.579]; (found) [M+H]$^+$=324 and [M+2+H]$^+$=326.

f) (R)-(+)-N-[1-(5-Bromo-2-fluoro-phenyl)-2-hydroxy-1-methyl-ethyl]-2-chloro-acetamide and (S)-(−)-N-[1-(5-Bromo-2-fluoro-phenyl)-2-hydroxy-1-methyl-ethyl]-2-chloro-acetamide A solution of (RS)-N-[1-(5-bromo-2-fluoro-phenyl)-2-hydroxy-1-methyl-ethyl]-2-chloro-acetamide (2.7 g) in dichloromethane was divided in 100 mg aliquots which were separated on chiral HPLC (Reprosil Chiral NR 8 µm, 250×30 mm, Dr. Maisch GmbH) using a 85:15-mixture of heptane and isopropanol as the eluent. The first eluting enantiomer (retention time: 9.94 min), the (S)-(−)-N-[1-(5-bromo-2-fluoro-phenyl)-2-hydroxy-1-methyl-ethyl]-2-chloro-acetamide, was obtained as a light yellow waxy solid (1.05 g, 39%), and the second eluting enantiomer (retention time: 12.92 min), the (R)-(+)-N-[1-(5-bromo-2-fluoro-phenyl)-2-hydroxy-1-methyl-ethyl]-2-chloro-acetamide, was also obtained as a light yellow waxy solid (1.07 g, 40%), with e.e. >99% each.

g) (R)-5-(5-Bromo-2-fluoro-phenyl)-5-methyl-morpholin-3-one

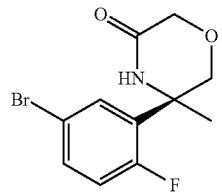 [SMILES: C[C@@]1(c2cc(Br)ccc2F)COCC(=O)N1]

The cyclization of the (R)-N-[1-(5-bromo-2-fluoro-phenyl)-2-hydroxy-1-methyl-ethyl]-2-chloro-acetamide with potassium tert-butylate yielded, after chromatography on silica gel using a gradient of dichloromethane/methanol=100/0 to 75/25 as the eluent, the title compound as a white solid. Mass (calculated) C$_{11}$J$_{11}$BrFNO$_2$ [288.118]; (found) [M+H]$^+$=288 and [M+2+H]$^+$=290.

Preparation of Building Block C (RS)-3-(3-Bromo-phenyl)-5-methoxy-3-methyl-3,6-dihydro-2H [1,4]oxazine

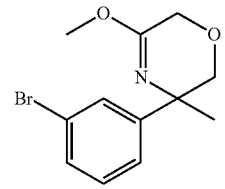 [SMILES: COC1=NC(C)(c2cccc(Br)c2)COC1]

In a vacuum dried flask under an argon atmosphere, a solution of (RS)-5-(3-bromo-phenyl)-5-methyl-morpholin-3-one (3.0 g, 11.1 mmol) in dichloromethane (145 ml) was treated with trimethyloxonium tetrafluoroborate (2.594 g, 17 mmol). The reaction mixture was stirred at room temperature for 17 hours. For the workup, the incomplete reaction was extracted with a saturated solution of sodium hydrogen carbonate (70 ml). The organic layer was dried over sodium sulphate and evaporated. There were obtained 3.12 g of the title compound as a light yellow oil containing about 17% of the starting lactam. Mass (calculated) C$_{12}$H$_{14}$BrNO$_2$ [284.16]; (found) [M+H]$^+$=284 and [M+H]$^+$=286.

Preparation of Building Block D (RS)-[Bis-(4-methoxy-phenyl)-phenyl-methyl]-[5-(3-bromo-phenyl)-5-methyl-5,6-dihydro-2H-[1,4]oxazin-3-yl]-amine

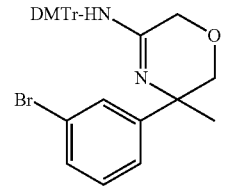

a) (RS)-5-(3-Bromo-phenyl)-5-methyl-5,6-dihydro-2H-[1,4]oxazin-3-ylamine

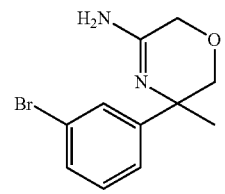

In a vacuum dried flask under an argon atmosphere, a solution of 5-(3-bromo-phenyl)-5-methyl-morpholin-3-one (7.4 g, 27.4 mmol) in dichloromethane (80 ml) was treated with trimethyloxonium tetrafluoroborate (11.6 g, 3 eq). The reaction mixture was stirred at room temperature overnight. The LC-MS profile showed partial conversion into the desired compound so another 1.5 eq of trimethyloxonium tetrafluoroborate were added and the reaction mixture was stirred at room temperature overnight. For the workup, the reaction mixture was washed with a saturated solution of sodium hydrogen-carbonate (50 ml). The organic layer was dried over sodium sulphate and evaporated. The crude product was dissolved in methanol (60 ml) in a microreactor and ammonium chloride (7.4 g, 5.3 eq) was added. The reaction mixture was heated at 100° C. for 16 hours. After cooling, the reaction mixture was filtered and evaporated to dryness, taken up with dichloromethane (30 ml) and filtered again. The solvent was removed and the residue was passed through a SCX (50 g) cartridge, washed with a dichloromethane/methanol mixture and the product was recovered eluting with a solution 2.0 M of ammonia in methanol. The (RS)-5-(3-bromo-phenyl)-5-methyl-5,6-dihydro-2H-[1,4]oxazin-3-ylamine was obtained as a brown oil (3.7 g, 53%). Mass (calculated) $C_{11}H_{13}BrN_2O$ [269.14]; (found) $[M+H]^+=271$.

b) (RS)-[Bis-(4-methoxy-phenyl)-phenyl-methyl]-[5-(3-bromo-phenyl)-5-methyl-5,6-dihydro-2H-[1,4]oxazin-3-yl]-amine

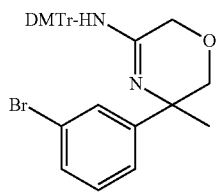

A solution of (RS)-5-(3-bromo-phenyl)-5-methyl-5,6-dihydro-2H-[1,4]oxazin-3-ylamine (3.7 g, 13.8 mmol) and triethylamine (1.5 g, 1.1 eq) in dichloromethane (20 ml) was cooled to 0° C. and 4,4'-dimethoxytriphenylmethyl chloride (5.12 g, 1.1 eq) was added. The reaction mixture was stirred at room temperature overnight. Thereafter, water was added to the mixture and the organic phase was separated, dried over sodium sulphate and concentrated at reduced pressure. The crude was purified by chromatography on silica gel to yield the (RS)-[bis-(4-methoxy-phenyl)-phenyl-methyl]-[5-(3-bromo-phenyl)-5-methyl-5,6-dihydro-2H-[1,4]oxazin-3-yl]-amine as a yellow oil (7.0 g, 99%). Mass (calculated) $C_3H_{31}BrN_2O_3$ [571.52]; (found) $[M+H]^+=571$.

Preparation of Building Block E

[Bis-(4-methoxy-phenyl)-phenyl-methyl]-[(R)-5-(5-bromo-2-fluoro-phenyl)-5-methyl-5,6-dihydro-2H-[1,4]oxazin-3-yl]-amine

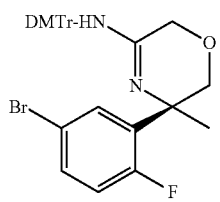

a) (R)-5-(5-Bromo-2-fluoro-phenyl)-5-methyl-5,6-dihydro-2H-[1,4]oxazin-3-ylamine

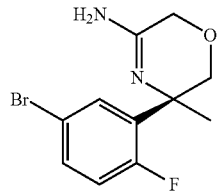 [SMILES: C[C@@]1(c2cc(Br)ccc2F)COCC(N)=N1]

In analogy to step a) in the synthesis of building block D, the treatment of (R)-5-(5-bromo-2-fluoro-phenyl)-5-methyl-morpholin-3-one with trimethyloxonium tetrafluoroborate followed by the nucleophilic substitution with ammonium chloride yielded the title compound; its hydrochloride was obtained as a white solid (74%). Mass (calculated) $C_{11}H_{12}BrFN_2O$ [287.13]; (found) $[M+H]^+=287$, $[M+2+H]^+=289$.

b) [Bis-(4-methoxy-phenyl)-phenyl-methyl]-[(R)-5-(5-bromo-2-fluoro-phenyl)-5-methyl-5,6-dihydro-2H-[1,4]oxazin-3-yl]-amine

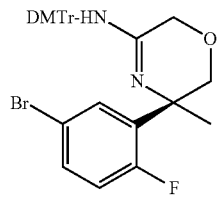

In analogy to step b) in the synthesis of building block D, the reaction of (R)-5-(5-bromo-2-fluoro-phenyl)-5-methyl-5,6-dihydro-2H-[1,4]oxazin-3-ylamine with 4,4'-dimethoxytriphenyl-methyl chloride yielded the title compound as a white solid (72%). Mass (calculated) $C_{32}H_{30}BrFN_2O_3$ [589.51]; (found) $[M+H]^+=589$, $[M+2+H]^+=591$.

Preparation of Building Block F

[Bis-(4-methoxy-phenyl)-phenyl-methyl]-[(RS)-5-(5-bromo-2-fluoro-phenyl)-5-methyl-5,6-dihydro-2H-[1,4]oxazin-3-yl]-amine

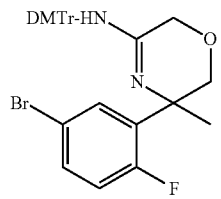

a) (RS)-5-(5-Bromo-2-fluoro-phenyl)-5-methyl-morpholin-3-one

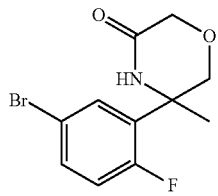

The cyclization of the (RS)-N-[1-(5-bromo-2-fluoro-phenyl)-2-hydroxy-1-methyl-ethyl]-2-chloro-acetamide [preparation of building block B e)] with potassium tert-butylate yielded, after chromatography on silica gel using a gradient of dichloromethane/methanol=100/0 to 75/25 as the eluent, the title compound as a white solid. Mass (calculated) $C_{11}H_{11}BrFNO_2$ [288.118]; (found) $[M+H]^+=288$ and $[M+2+H]^+=290$.

b) (RS)-5-(5-Bromo-2-fluoro-phenyl)-5-methyl-5,6-dihydro-2H-[1,4]oxazin-3-ylamine

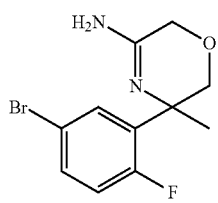

In analogy to step a) in the synthesis of building block D, the treatment of (RS)-5-(5-bromo-2-fluoro-phenyl)-5-methyl-morpholin-3-one with trimethyloxonium tetrafluoroborate followed by the nucleophilic substitution with ammonium chloride yielded the title compound; its hydrochloride was obtained as a white solid. Mass (calculated) $C_{11}H_{12}BrFN_2O$ [287.13]; (found) $[M+H]^+=287$, $[M+2+H]^+=289$.

c) [Bis-(4-methoxy-phenyl)-phenyl-methyl]-[(RS)-5-(5-bromo-2-fluoro-phenyl)-5-methyl-5,6-dihydro-2H-[1,4]oxazin-3-yl]-amine

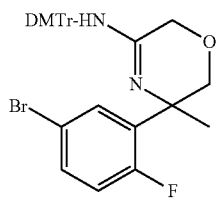

In analogy to step b) in the synthesis of building block D, the reaction of (RS)-5-(5-bromo-2-fluoro-phenyl)-5-methyl-5,6-dihydro-2H-[1,4]oxazin-3-ylamine with 4,4'-dimethoxytriphenyl-methyl chloride yielded the title compound as a white solid. Mass (calculated) $C_{32}H_{30}BrFN_2O_3$ [589.51]; (found) $[M+H]^+=589$, $[M+2+H]^+=591$.

EXAMPLE 1 (Method A)

5-[3-(3-Chloro-benzylamino)-phenyl]-5-methyl-5,6-dihydro-2H-[1,4]oxazin-3-ylamine a) (RS)-(3-Chloro-benzyl)-[3-(5-methoxy-3-methyl-3,6-dihydro-2H-[1,4]oxazin-3-yl)-phenyl]-amine A dried pressure tube was charged consecutively under a nitrogen atmosphere with a solution of (RS)-3-(3-bromo-phenyl)-5-methoxy-3-methyl-3,6-dihydro-2H [1,4]oxazine (150 mg, 0.5 mmol) in toluene (5 ml), sodium tert-butylate (157 mg, 1.6 mmol), 2-di-tert-butylphosphino-2',4',6'-triisopropylbiphenyl (tert-butyl-x-phos) (23 mg, 0.1 mmol), tris(dibenzylideneacetone)-dipalladium chloroform complex (17 mg), and 3-chlorobenzylamine (154 mg, 1.1 mmol). The sealed pressure tube was heated at 100° C. for 15 hours. After cooling, the reaction mixture was evaporated to dryness and directly purified by chromatography on an Isolute flash NH$_2$ column using a gradient of heptane/ethyl acetate=100/0 to 50/50 as the eluent. 85 mg (47%) of (RS)-(3-chloro-benzyl)-[3-(5-methoxy-3-methyl-3,6-dihydro-2H-[1,4]oxazin-3-yl)-phenyl]-amine were obtained as a yellow oil. Mass (calculated) $C_{19}H_{21}ClN_2O_2$ [344.844]; (found) $[M+H]^+=345$.

b) (RS)-5-[3-(3-Chloro-benzylamino)-phenyl]-5-methyl-5,6-dihydro-2H-[1,4]oxazin-3-ylamine In analogy to step a) in the synthesis of building block D, the treatment of (RS)-(β-chloro-benzyl)-[3-(5-methoxy-3-methyl-3,6-dihydro-2H-[1,4]oxazin-3-yl)-phenyl]-amine with ammonium chloride yielded after chromatography on an Isolute flash NH$_2$ column using a gradient of heptane/ethyl acetate=100/0 to 90/10 as the eluent the title compound as a light yellow waxy solid (68%). Mass (calculated) $C_{18}H_{20}ClN_3O$ [329.833]; (found) $[M+H]^+=330$.

EXAMPLES 2-4

In a reaction sequence analogous to that described in Example 1 (method A), the following compounds were obtained starting from the palladium-catalyzed amination of building block C, (RS)-3-(3-bromo-phenyl)-5-methoxy-3-methyl-3,6-dihydro-2H [1,4]oxazine with the corresponding amine followed by the treatment with ammonium chloride:

EXAMPLE 2

5-[3-(4-Chloro-benzylamino)-phenyl]-5-methyl-5,6-dihydro-2H-[1,4]oxazin-3-ylamine With 4-chlorobenzylamine the 5-[3-(4-chloro-benzylamino)-phenyl]-5-methyl-5,6-dihydro-2H-[1,4]oxazin-3-ylamine as a white foam; (calculated) $C_{18}H_{20}ClN_3O$ [329.833]; (found) $[M+H]^+=330$.

EXAMPLE 3

5-[3-(2,4-Dichloro-benzylamino)-phenyl]-5-methyl-5,6-dihydro-2H-[1,4]oxazin-3-ylamine With 2,4-dichlorobenzylamine the 5-[3-(2,4-dichloro-benzylamino)-phenyl]-5-methyl-5,6-dihydro-2H-[1,4]oxazin-3-ylamine as a white foam; (calculated) $C_{18}H_{19}Cl_2N_3O$ [364.274]; (found) $[M+H]^+=364$ and $[M+2+H]^+=366$.

EXAMPLE 4

5-{3-[1-(4-Chloro-phenyl)-ethylamino]-phenyl}-5-methyl-5,6-dihydro-2H-[1,4]oxazin-3-ylamine With (RS)-1-(4-chloro-phenyl)-ethylamine the 5-{3-[1-(4-chloro-phenyl)-ethylamino]-phenyl}-5-methyl-5,6-dihydro-2H-[1,4]oxazin-3-ylamine as a white foam; (calculated) $C_{19}H_{22}ClN_3O$ [343.856]; (found) $[M+H]^+=344$.

EXAMPLE 5 (Method B)

(R)-5-(5-Butylamino-2-fluoro-phenyl)-5-methyl-5,6-dihydro-2H-[1,4]oxazin-3-ylamine a) [Bis-(4-methoxy-phenyl)-phenyl-methyl]-[(R)-5-(5-butylamino-2-fluoro-phenyl)-5-methyl-5,6-dihydro-2H-[1,4]oxazin-3-yl]-amine

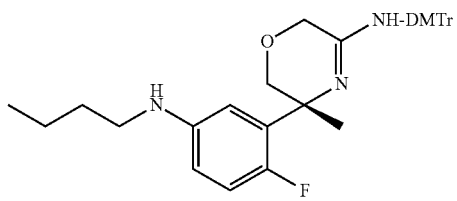

In analogy to step b) in Example 1 the palladium-catalyzed amination of building block E, [bis-(4-methoxy-phenyl)-phenyl-methyl]-[(R)-5-(5-bromo-2-fluoro-phenyl)-5-methyl-5,6-dihydro-2H-[1,4]oxazin-3-yl]-amine, with n-butylamine yielded after flash chromatography on silica gel using a gradient of heptane/ethyl acetate=100/0 to 100/0 as the eluent the title compound as a light yellow oil (88%); (calculated) $C_{18}H_{20}ClN_3O$ [581.74]; (found) $[M+H]^+=582$.

b) (R)-5-(5-Butylamino-2-fluoro-phenyl)-5-methyl-5,6-dihydro-2H-[1,4]oxazin-3-ylamine A solution of [bis-(4-methoxy-phenyl)-phenyl-methyl]-[(R)-5-(5-butylamino-2-fluoro-phenyl)-5-methyl-5,6-dihydro-2H-[1,4]oxazin-3-yl]-amine (26 mg, 44.7 mol) in dichloromethane 2.5 ml) was treated at room temperature with trifluoroacetic acid (17.1 1, 223 mol) for 20 hours. The reaction mixture was evaporated at reduced pressure and the crude product purified by flash chromatography on silica gel using a gradient of dichloromethane/methanol=100/0 to 90/10 as the eluent. The title compound was obtained as a light yellow oil (58%); (calculated) $C_{15}H_{22}FN_3O$ [279.350]; (found) $[M+H]^+=280$.

EXAMPLES 6-23

In a reaction sequence analogous to that described in Example 5 (method B), the following compounds were obtained starting from the palladium-catalyzed amination of building block E, [bis-(4-methoxy-phenyl)-phenyl-methyl]-[(R)-5-(5-bromo-2-fluoro-phenyl)-5-methyl-5,6-dihydro-2H-[1,4]oxazin-3-yl]-amine, with the corresponding amine followed by the cleavage of the protecting group with trifluoroacetic acid:

EXAMPLE 6

(R)-5-(2-fluoro-5-(isopentylamino)phenyl)-5-methyl-5,6-dihydro-2H-1,4-oxazin-3-amine With 3-methyl-butylamine the (R)-5-[2-fluoro-5-(3-methyl-butylamino)-phenyl]-5-methyl-5,6-dihydro-2H-[1,4]oxazin-3-ylamine as a colourless oil; (calculated) $C_{16}H_{24}FN_3O$ [293.380]; (found) $[M+H]^+=294$.

EXAMPLE 7

(R)-5-(2-fluoro-5-(pentan-3-ylamino)phenyl)-5-methyl-5,6-dihydro-2H-1,4-oxazin-3-amine With 1-ethyl-propylamine the (R)-5-[5-(1-ethyl-propylamino)-2-fluoro-phenyl]-5-methyl-5,6-dihydro-2H-[1,4]oxazin-3-ylamine as a colourless oil; (calculated) $C_{16}H_{24}FN_3O$ [293.380]; (found) $[M+H]^+=294$.

EXAMPLE 8

(5R)-5-(2-fluoro-5-(3-methylbutan-2-ylamino)phenyl)-5-methyl-5,6-dihydro-2H-1,4-oxazin-3-amine With (RS)-1,2-dimethyl-propylamine the (5R)-5-(2-fluoro-5-(3-methylbutan-2-ylamino)phenyl)-5-methyl-5,6-dihydro-2H-1,4-oxazin-3-amine as a colourless oil; (calculated) $C_{16}H_{24}FN_3O$ [293.380]; (found) $[M+H]^+=294$.

EXAMPLE 9

(R)-5-(2-fluoro-5-(2,2,2-trifluoroethylamino)phenyl)-5-methyl-5,6-dihydro-2H-1,4-oxazin-3-amine With 2,2,2-trifluoro-ethylamine the (R)-5-[2-Fluoro-5-(2,2,2-trifluoro-ethylamino)-phenyl]-5-methyl-5,6-dihydro-2H-[1,4]oxazin-3-ylamine as a light yellow oil; (calculated) $C_{13}H_{15}F_4N_3O$ [305.270]; (found) $[M+H]^+=306$.

EXAMPLE 10

(R)-5-[5-(2,2-Difluoro-ethylamino)-2-fluoro-phenyl]-5-methyl-5,6-dihydro-2H-[1,4]oxazin-3-ylamine With 2,2-difluoro-ethylamine the (R)-5-[5-(2,2-Difluoro-ethylamino)-2-fluoro-phenyl]-5-methyl-5,6-dihydro-2H-[1,4]oxazin-3-ylamine as a light yellow oil; (calculated) $C_{13}H_{16}F_3N_3O$ [287.280]; (found) $[M+H]^+=288$.

EXAMPLE 11

(R)-5-(2-fluoro-5-(2,2,3,3,3-pentafluoropropylamino)phenyl)-5-methyl-5,6-dihydro-2H-1,4-oxazin-3-amine With 2,2,3,3,3-pentafluoro-propylamine the (R)-5-[2-fluoro-5-(2,2,3,3,3-pentafluoro-propylamino)-phenyl]-5-methyl-5,6-dihydro-2H-[1,4]oxazin-3-ylamine as a light yellow foam; (calculated) $C_{14}H_{15}F_6N_3O$ [355.280]; (found) $[M+H]^+=356$.

EXAMPLE 12

(R)-5-(2-fluoro-5-(3,3,3-trifluoropropylamino)phenyl)-5-methyl-5,6-dihydro-2H-1,4-oxazin-3-amine With 3,3,3-trifluoro-propylamine the (R)-5-(2-fluoro-5-(3,3,3-trifluoropropylamino)-phenyl]-5-methyl-5,6-dihydro-2H-[1,4]oxazin-3-ylamine as a light yellow solid; (calculated) $C_{14}H_{17}F_3N_3O$ [319.300]; (found) $[M+H]^+=320$.

EXAMPLE 13

(R)-5-(2-fluoro-5-(3-(methylthio)propylamino)phenyl)-5-methyl-5,6-dihydro-2H-1,4-oxazin-3-amine With 3-methylsulfanyl-propylamine the (R)-5-[2-fluoro-5-(3-methylsulfanyl-propylamino)-phenyl]-5-methyl-5,6-dihydro-2H-[1,4]oxazin-3-ylamine as a colourless oil; (calculated) $C_{15}H_{22}FN_3OS$ [311.420]; (found) $[M+H]^+=312$.

EXAMPLE 14

(R)-5-(5-Cyclobutylamino-2-fluoro-phenyl)-5-methyl-5,6-dihydro-2H-[1,4]oxazin-3-ylamine With cyclobutylamine the (R)-5-(5-cyclobutylamino-2-fluoro-phenyl)-5-methyl-5,6-dihydro-2H-[1,4]oxazin-3-ylamine as a light yellow oil; (calculated) $C_{15}H_{20}FN_3O$ [277.340]; (found) $[M+H]^+=278$.

EXAMPLE 15

(R)-5-(5-(cyclopentylamino)-2-fluorophenyl)-5-methyl-5,6-dihydro-2H-1,4-oxazin-3-amine With cyclopentylamine the (R)-5-(5-cyclopentylamino-2-fluorophenyl)-5-methyl-5,6-dihydro-2H-[1,4]oxazin-3-ylamine as a light yellow oil; (calculated) $C_{16}H_{22}FN_3O$ [291.360]; (found) $[M+H]^+=292$.

EXAMPLE 16

(R)-5-(5-(cyclohexylamino)-2-fluorophenyl)-5-methyl-5,6-dihydro-2H-1,4-oxazin-3-amine With cyclohexylamine the (R)-5-(5-cyclohexylamino-2-fluorophenyl)-5-methyl-5,6-dihydro-2H-[1,4]oxazin-3-ylamine as a light yellow solid; (calculated) $C_{17}H_{24}FN_3O$ [305.390]; (found) $[M+H]^+=306$.

EXAMPLE 17

5-[(R)-5-((1R,2R,4R)-7,7-dimethyl-bicyclo[2.2.1]hept-2-ylamino)-2-fluoro-phenyl]-5-methyl-5,6-dihydro-2H-[1,4]oxazin-3-ylamine With (1R,2R,4R)-7,7-dimethyl-bicyclo[2.2.1]hept-2-ylamine the 5-[(R)-5-((1R,2R,4R)-7,7-dimethyl-bicyclo[2.2.1]hept-2-ylamino)-2-fluoro-phenyl]-5-methyl-5,6-dihydro-2H-[1,4]oxazin-3-ylamine as a light yellow solid; (calculated) $C_{20}H_{28}FN_3O$ [345.450]; (found) $[M+H]^+=346$.

EXAMPLE 18

(R)-5-[2-Fluoro-5-(tetrahydro-furan-3-ylamino)-phenyl]-5-methyl-5,6-dihydro-2H-[1,4]oxazin-3-ylamine With tetrahydro-furan-3-ylamine the (R)-5-[2-Fluoro-5-(tetrahydro-furan-3-ylamino)-phenyl]-5-methyl-5,6-dihydro-2H-[1,4]oxazin-3-ylamine as a light brown waxy solid; (calculated) $C_{15}H_{20}FN_3O_2$ [293.340]; (found) $[M+H]^+=294$.

EXAMPLE 19

(1S,2S)-2-(3-((R)-5-amino-3-methyl-3,6-dihydro-2H-1,4-oxazin-3-yl)-4-fluorophenylamino)cyclopentanol With (1S,2S)-2-amino-cyclopentanol the (1S,2S)-2-[3-((R)-5-amino-3-methyl-3,6-dihydro-2H-[1,4]oxazin-3-yl)-4-fluoro-phenylamino]-cyclopentanol as a light brown waxy solid; (calculated) $C_{16}H_{22}FN_3O_2$ [307.360]; (found) $[M+H]^+=308$.

EXAMPLE 20

(1R,2S)-2-(3-((R)-5-amino-3-methyl-3,6-dihydro-2H-1,4-oxazin-3-yl)-4-fluorophenylamino)cyclopentanol With (1R,2S)-2-amino-cyclopentanol the (1R,2S)-2-[3-((R)-5-amino-3-methyl-3,6-dihydro-2H-[1,4]oxazin-3-yl)-4-fluoro-phenylamino]-cyclopentanol as a light brown waxy solid; (calculated) $C_{16}H_{22}FN_3O_2$ [307.360]; (found) $[M+H]^+=308$.

EXAMPLE 21

(R)-5-(5-(cyclopropylmethylamino)-2-fluorophenyl)-5-methyl-5,6-dihydro-2H-1,4-oxazin-3-amine With cyclopropylmethyl-amine the (R)-5-(5-(cyclopropylmethylamino)-2-fluorophenyl)-5-methyl-5,6-dihydro-2H-1,4-oxazin-3-amine as a white solid; (calculated) $C_{15}H_{20}FN_3O$ [277.340]; (found) $[M+H]^+=278$.

EXAMPLE 22

(R)-5-(2-fluoro-5-(((R)-tetrahydrofuran-2-yl)methylamino)phenyl)-5-methyl-5,6-dihydro-2H-1,4-oxazin-3-amine With [(R)-1-(tetrahydro-furan-2-yl)]-methylamine the (R)-5-(2-fluoro-5-(((R)-tetrahydrofuran-2-yl)methylamino)phenyl)-5-methyl-5,6-dihydro-2H-1,4-oxazin-3-amine as a light brown waxy solid; (calculated) $C_{16}H_{22}FN_3O_2$ [307.360]; (found) $[M+H]^+=308$.

EXAMPLE 23

(R)-5-{5-[1-(5-Chloro-pyridin-2-yl)-2-methyl-propylamino]-2-fluoro-phenyl}-5-methyl-5,6-dihydro-2H-[1,4]oxazin-3-ylamine or (R)-5-{5-[1-(5-Chloro-pyridin-2-yl)-2-methyl-propylamino]-2-fluoro-phenyl}-5-methyl-5,6-dihydro-2H-[1,4]oxazin-3-ylamine hydrochloride With (RS)-1-(5-chloro-pyridin-2-yl)-2-methyl-propylamine the (R)-5-{5-[1-(5-Chloro-pyridin-2-yl)-2-methyl-propylamino]-2-fluoro-phenyl}-5-methyl-5,6-dihydro-2H-[1,4]oxazin-3-ylamine hydrochloride; (calculated) $C_{20}H_{24}ClFN_4O$ [390.16+35.98]; (found) $[M+H]^+=391$

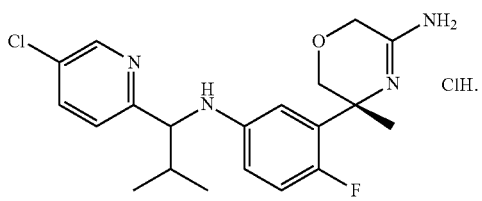 [SMILES: CC(C)C(Nc1ccc(F)c([C@]2(C)COCC(N)=N2)c1)c1ccc(Cl)cn1 ; Cl]

EXAMPLE 24 (Method C)

[3-(5-Amino-3-methyl-3,6-dihydro-2H-[1,4]oxazin-3-yl)-phenyl]-(3-chloro-quinolin-8-yl)-amine or [3-(5-Amino-3-methyl-3,6-dihydro-2H-[1,4]oxazin-3-yl)-phenyl]-(3-chloro-quinolin-8-yl)-amine hydrochloride

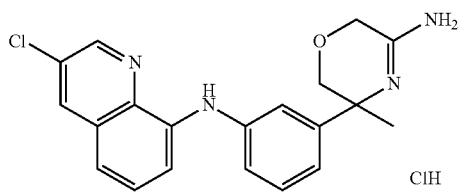 [SMILES: CC1(c2cccc(Nc3cccc4cc(Cl)cnc34)c2)COCC(N)=N1 ; Cl]

a) (RS)-5-[3-(3-Chloro-quinolin-8-ylamino)-phenyl]-5-methyl-morpholin-3-one

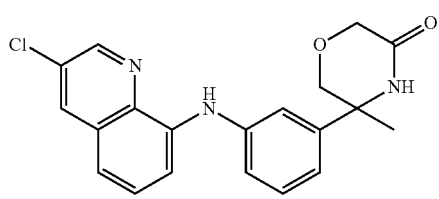 [SMILES: CC1(c2cccc(Nc3cccc4cc(Cl)cnc34)c2)COCC(=O)N1]

In analogy to step b) in Example 1 the palladium-catalyzed amination of building block A, (RS)-5-(3-bromo-phenyl)-5-methyl-morpholin-3-one, with 3-chloro-quinolin-8-ylamine (CAS139399-66-9) yielded the title compound in 72%; (calculated) $C_{20}H_{18}ClN_3O_2$ [367.84]; (found) $[M+H]^+=368$.

b) (RS)-5-[3-(3-Chloro-quinolin-8-ylamino)-phenyl]-5-methyl-morpholine-3-thione

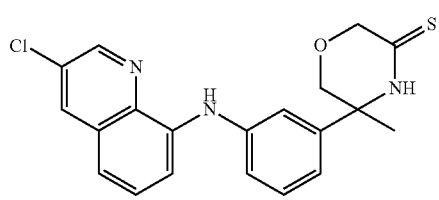

A solution of (RS)-5-[3-(3-chloro-quinolin-8-ylamino)-phenyl]-5-methyl-morpholin-3-one (368 mg, 1.1 mmol) in tetrahydrofuran was treated with Lawesson's reagent (500 mg, 1.2 mmol) at room temperature during 3 hours. The progress of the reaction was checked by LC-MS. For the workup, the reaction mixture was evaporated at reduced pressure. The residue was partitioned between water (5 ml) and ethyl acetate (5 ml), then the organic layer separated, dried over sodium sulphate and evaporated. The crude product was purified by flash chromatography on silica gel using a gradient of cyclohexane/ethyl acetate as the eluent yielding 300 mg (71%) of (RS)-5-[3-(3-chloro-quinolin-8-ylamino)-phenyl]-5-methyl-morpholine-3-thione; (calculated) $C_{20}H_{18}ClN_3OS$ [383.90]; (found) $[M+H]^+=384$.

c) [3-(5-Amino-3-methyl-3,6-dihydro-2H-[1,4]oxazin-3-yl)-phenyl]-(3-chloro-quinolin-8-yl)-amine and [3-(5-Amino-3-methyl-3,6-dihydro-2H-[1,4]oxazin-3-yl)-phenyl]-(3-chloro-quinolin-8-yl)-amine hydrochloride A dried pressure tube was charged under an argon atmosphere with a dispersion of (RS)-5-[3-(3-chloro-quinolin-8-ylamino)-phenyl]-5-methyl-morpholine-3-thione (300 mg, 0.8 mmol) in ammonia in methanol (7 M, 8 ml). The tube was sealed and heated at 100° C. for 3 hours. After cooling, the reaction mixture was evaporated to dryness, the residue dissolved in dichloromethane and loaded onto a SCX-cartridge. A 1:1-mixture of dichloromethane and methanol was passed through the column to remove impurities. Thereafter, the product was eluted with ammonia in methanol (2 M). The crude product was purified by mass triggered preparative HPLC yielding 46 mg (16%) of the title compound; treatment with hydrochloric acid yielded in the corresponding hydrochloride (calculated) $C_{20}H_{19}ClN_4O$ [366.85]; (found) $[M+H]^+=367$.

EXAMPLE 25

[3-(5-Amino-3-methyl-3,6-dihydro-2H-[1,4]oxazin-3-yl)-phenyl]-quinolin-8-yl-amine or [3-(5-Amino-3-methyl-3,6-dihydro-2H-[1,4]oxazin-3-yl)-phenyl]-quinolin-8-yl-amine hydrochloride In a reaction sequence analogous to that described in Example 24 (method C), the palladium-catalyzed amination of building block A with quinolin-8-ylamine followed by the oxygen-sulphur-exchange with Lawesson's reagent and the ammonolysis of the corresponding morpholine-3-thione yielded the title compound; (calculated) $C_{20}H_{20}N_4O$ [332.41]; (found) $[M+H]^+=333$.

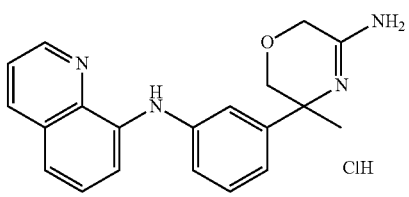 [SMILES: CC1(c2cccc(Nc3cccc4cccnc34)c2)COCC(N)=N1 ; Cl]

EXAMPLES 26-35

In a reaction sequence analogous to that described in Example 5 (method B), the following compounds were obtained starting from the palladium-catalyzed amination of building block E, [bis-(4-methoxy-phenyl)-phenyl-methyl]-[(R)-5-(5-bromo-2-fluoro-phenyl)-5-methyl-5,6-dihydro- 2H-[1,4]oxazin-3-yl]-amine, with the corresponding amine followed by the cleavage of the protecting group with trifluoroacetic acid:

EXAMPLE 26

[3-((R)-5-Amino-3-methyl-3,6-dihydro-2H-[1,4]oxazin-3-yl)-4-fluoro-phenyl]-(3-chloro-quinolin-8-yl)-amine or [3-((R)-5-Amino-3-methyl-3,6-dihydro-2H-[1,4]oxazin-3-yl)-4-fluoro-phenyl]-(3-chloro-quinolin-8-yl)-amine hydrochloride With 3-chloro-quinolin-8-ylamine (CAS139399-66-9) the [3-((R)-5-Amino-3-methyl-3,6-dihydro-2H-[1,4]oxazin-3-yl)-4-fluoro-phenyl]-(3-chloro-quinolin-8-yl)-amine; treatment with hydrochloric acid yielded the corresponding hydrochloride (calculated) $C_{20}H_{18}ClFN_4O$ [384.840]; (found) $[M+H]^+=385$.

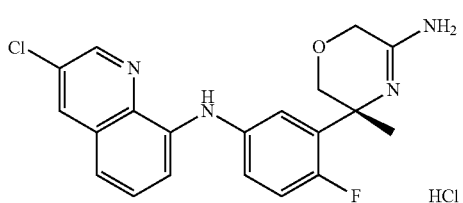 [SMILES: C[C@@]1(c2cc(Nc3cccc4cc(Cl)cnc34)ccc2F)COCC(N)=N1 ; Cl]

EXAMPLE 27

[3-((R)-5-Amino-3-methyl-3,6-dihydro-2H-[1,4]oxazin-3-yl)-4-fluoro-phenyl]-(3,6-dichloro-quinolin-8-yl)-amine or [3-((R)-5-Amino-3-methyl-3,6-dihydro-2H-[1,4]oxazin-3-yl)-4-fluoro-phenyl]-(3,6-dichloro-quinolin-8-yl)-amine hydrochloride With 3,6-dichloro-quinolin-8-ylamine [CAS158117-56-7, H. Gershon et al. Monatshefte für Chemie (1994), 125 (6-7), 723-30] the [3-((R)-5-Amino-3-methyl-3,6-dihydro-2H-[1,4]oxazin-3-yl)-4-fluoro-phenyl]-(3,6-dichloro-quinolin-8-yl)-amine; treatment with hydrochloric acid yielded the corresponding hydrochloride (calculated) $C_{20}H_{17}Cl_2FN_4O$ [419.29]; (found) $[M+H]^+=419$.

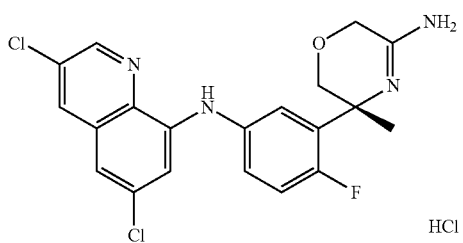 [SMILES: C[C@@]1(c2cc(Nc3cc(Cl)cc4cc(Cl)cnc34)ccc2F)COCC(N)=N1 ; Cl]

EXAMPLE 28

[3-((R)-5-Amino-3-methyl-3,6-dihydro-2H-[1,4]oxazin-3-yl)-4-fluoro-phenyl]-(3-chloro-6-fluoro-quinolin-8-yl)-amine or [3-((R)-5-Amino-3-methyl-3,6-dihydro-2H-[1,4]oxazin-3-yl)-4-fluoro-phenyl]-(3-chloro-6-fluoro-quinolin-8-yl)-amine hydrochloride With 3-chloro-6-fluoro-quinolin-8-ylamine [CAS515170-52-2, H. Gershon et al. Monatshefte für Chemie (1994), 125 (6-7), 723-30] the [3-((R)-5-Amino-3-methyl-3,6-dihydro-2H-[1,4]oxazin-3-yl)-4-fluoro-phenyl]-(3-chloro-6-fluoro-quinolin-8-yl)-amine; treatment with hydrochloric acid yielded the corresponding hydrochloride (calculated) $C_{20}H_{17}ClF_2N_4O$ [402.83]; (found) $[M+H]^+=403$.

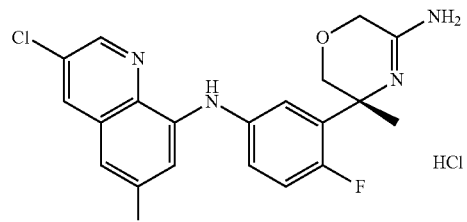

EXAMPLE 29

[3-((R)-5-Amino-3-methyl-3,6-dihydro-2H-[1,4]oxazin-3-yl)-4-fluoro-phenyl]-(3-difluoromethoxy-quinolin-8-yl)-amine or [3-((R)-5-Amino-3-methyl-3,6-dihydro-2H-[1,4]oxazin-3-yl)-4-fluoro-phenyl]-(3-difluoromethoxy-quinolin-8-yl)-amine hydrochloride With 3-difluoromethoxy-quinolin-8-ylamine the [3-((R)-5-Amino-3-methyl-3,6-dihydro-2H-[1,4]oxazin-3-yl)-4-fluoro-phenyl]-(3-difluoromethoxy-quinolin-8-yl)-amine; treatment with hydrochloric acid yielded the corresponding hydrochloride (calculated) $C_{21}H_{19}F_3N_4O_2$ [416.41]; (found) $[M+H]^+=417$.

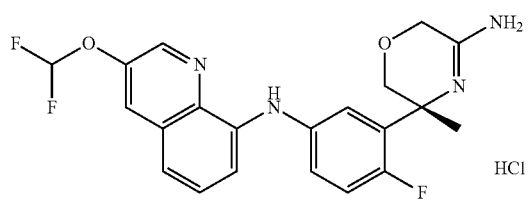 [SMILES: C[C@@]1(c2cc(Nc3cccc4cc(OC(F)F)cnc34)ccc2F)COCC(N)=N1 ; Cl]

The 3-difluoromethoxy-quinolin-8-ylamine was obtained as follows:

a) 3-Difluoromethoxy-8-nitro-quinoline

A solution of 8-nitro-quinolin-3-ol (CAS25369-37-3) (500 mg, 2.63 mmol) in dimethylformamide (5 ml) was treated with sodium chlorodifluoroacetate (481 mg, 3.15 mmol). The mixture was heated to 100° C. overnight under a nitrogen atmosphere. For the workup, the reaction mixture was cooled to room temperature, then saturated aqueous sodium carbonate solution and dichloromethane were added. The organic layer was separated, dried over sodium sulphate, then evaporated. The crude product was purified by chromatography on silica gel using a gradient of cyclohexane/ethyl acetate=9:1 to 8:1 as the eluent yielding 100 mg (16%) of the 3-difluoromethoxy-8-nitro-quinoline as a yellow solid; (calculated) $C_{10}H_6F_2N_2O_3$ [240.2]; (found) $[M+H]^+=241$.

b) 3-Difluoromethoxy-quinolin-8-ylamine

The starting 3-difluoromethoxy-8-nitro-quinoline (100 mg, 0.4 mmol) was dissolved in ethanol in order to obtain a final solution of 0.05M and reduced using H-Cube™ [hydrogenation reactor, ThalesNano Inc.]; conditions: 60° C., hydrogen, palladium on charcoal 10% as the catalyst, flow 1 ml/min, 1 cycle). For the workup, the solvent was evaporated, and the 3-difluoromethoxy-quinolin-8-ylamine was obtained as a yellow oil (55 mg, 63%) which was used in the next step without further purification; (calculated) $C_{10}H_8F_2N_2O$ [210.2]; (found) $[M+H]^+=211$.

EXAMPLE 30

[3-((R)-5-Amino-3-methyl-3,6-dihydro-2H-[1,4]oxazin-3-yl)-4-fluoro-phenyl]-[3-(2-fluoro-ethoxy)-quinolin-8-yl]-amine or [3-((R)-5-Amino-3-methyl-3,6-dihydro-2H-[1,4]oxazin-3-yl)-4-fluoro-phenyl]-[3-(2-fluoro-ethoxy)-quinolin-8-yl]-amine hydrochloride With 3-(2-fluoro-ethoxy)-quinolin-8-ylamine the [3-((R)-5-Amino-3-methyl-3,6-dihydro-2H-[1,4]oxazin-3-yl)-4-fluoro-phenyl]-[3-(2-fluoro-ethoxy)-quinolin-8-yl]-amine; treatment with hydrochloric acid (2M) in ether yielded the corresponding hydrochloride (calculated) $C_{22}H_{22}F_2N_4O_2$ [412.44]; (found) $[M+H]^+=413$.

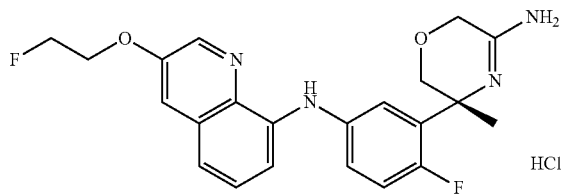 [SMILES: C[C@@]1(c2cc(Nc3cccc4cc(OCCF)cnc34)ccc2F)COCC(N)=N1 ; Cl]

The 3-(2-fluoro-ethoxy)-quinolin-8-ylamine was obtained as follows:

a) 3-(2-Fluoro-ethoxy)-8-nitro-quinoline

A solution of 8-nitro-quinolin-3-ol (500 mg, 2.63 mmol), methanesulphonic acid 2,2-difluoro-ethyl ester (463 mg, 2.9 mmol), ad potassium carbonate (810 mg, 5.86 mmol) in dimethylformamide (7 ml) was heated at 100° C. for 16 hours. For the workup, the reaction mixture was cooled to room temperature, then saturated aqueous sodium carbonate solution and dichloromethane were added. The organic layer was separated, dried over sodium sulphate, then evaporated. The crude product was purified by chromatography on silica gel using a gradient of cyclohexane/ethyl acetate=10:1 to 1:1 as the eluent yielding 150 mg (24%) of the 3-(2-fluoro-ethoxy)-8-nitro-quinoline as a yellow solid; (calculated) $C_{11}H_9FN_2O_3$ [236.2]; (found) $[M+H]^+=237$.

b) 3-(2-Fluoro-ethoxy)-quinolin-8-ylamine

The title compound was obtained in a manner analogous to that described in Example 29b) starting from 3-(2-fluoro-ethoxy)-8-nitro-quinoline and applying the H-Cube™ technology and yielding 110 mg (84%) of 3-(2-fluoro-ethoxy)-quinolin-8-ylamine as a pale yellow oil; (calculated) $C_{11}H_{11}FN_2O$ [206.2]; (found) $[M+H]^+=207$.

EXAMPLE 31

[3-((R)-5-Amino-3-methyl-3,6-dihydro-2H-[1,4]oxazin-3-yl)-4-fluoro-phenyl]-(3-cyclopropyl-methoxy-6-fluoro-quinolin-8-yl)-amine or [3-((R)-5-Amino-3-methyl-3,6-dihydro-2H-[1,4]oxazin-3-yl)-4-fluoro-phenyl]-(3-cyclopropylmethoxy-6-fluoro-quinolin-8-yl)-amine hydrochloride With 3-cyclopropylmethoxy-6-fluoro-quinolin-8-ylamine the [3-((R)-5-Amino-3-methyl-3,6-dihydro-2H-[1,4]oxazin-3-yl)-4-fluoro-phenyl]-(3-cyclopropylmethoxy-6-fluoro-quinolin-8-yl)-amine; treatment with hydrochloric acid (2M) in ether yielded the corresponding hydrochloride (calculated) $C_{24}H_{24}F_2N_4O_2$ [438.48]; (found) $[M+H]^+=439$.

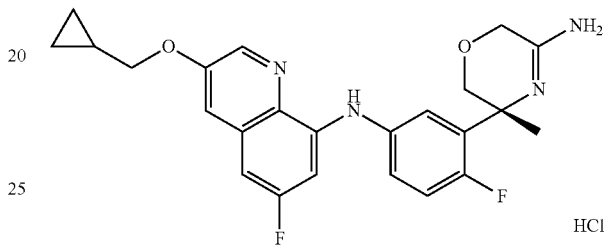

The 3-cyclopropylmethoxy-6-fluoro-quinolin-8-ylamine was obtained as follows:

a) 6-Fluoro-8-nitro-quinoline

4-Fluoro-2-nitro-phenylamine (15 g, 96 mmol) was added to a mixture of 4-nitrophenol (9.5 g, 144 mmol) and glycerol (27 ml), then concentrated sulphuric acid (8.3 ml, 154 mmol) was added dropwise. The mixture was stirred at 130° C. for 4 hours. For the workup, the reaction mixture was cooled to room temperature, then poured into ice-water. The precipitate was filtered and the aqueous phase was made basic with sodium hydroxide (15% solution). There were obtained 2.0 g (11%) of 6-fluoro-8-nitro-quinoline as a brown solid; (calculated) $C_9H_5FN_2O_2$ [192.2]; (found) $[M+H]^+=193$.

b) 6-Fluoro-8-nitro-quinolin-3-ol

A solution of 6-fluoro-8-nitro-quinoline (900 mg, 4.7 mmol) in acetic acid (10 ml) was treated at room temperature with hydrogen peroxide (30% in water (1.6 ml), then it was stirred at 70° C. for 5 hours. For the workup, the reaction mixture was cooled and poured into ice-water. The precipitate was filtered, washed with water, collected and dried. 6-Fluoro-8-nitro-quinolin-3-ol was obtained as a brown solid (285 mg, 29%); (calculated) $C_9H_5FN_2O_3$ [208.2]; (found) $[M-H]^-=207$.

c) 3-Cyclopropylmethoxy-6-fluoro-8-nitro-quinoline

A solution of 6-fluoro-8-nitro-quinolin-3-ol (1.285 g, 6.21 mmol) and cesium carbonate (4.046 g, 12.42 mmol) in dimethylsulfoxide (5 ml) was treated with bromomethyl-cyclopropane (1.09 g, 8.1 mmol). After stirring at room temperature overnight water (250 ml) was added and the mixture was extracted with ethyl acetate (2×20 ml) and dichloromethane (2×20 ml). The organic layers were collected, dried and evaporated. The crude product was purified by chromatography on silica gel using a 9:1-mixture of cyclohexane/ethyl acetate as the eluent. 3-Cyclopropylmethoxy-6-fluoro-8-nitro-quinoline was obtained as a yellow solid (600 mg, 45%); (calculated) $C_{13}H_{11}FN_2O_3$ [262.2]; (found) $[M+H]^+=263$.

d) 3-Cyclopropylmethoxy-6-fluoro-quinolin-8-ylamine

The title compound was obtained in a manner analogous to that described in Example 29 b) starting from 3-cyclopropylmethoxy-6-fluoro-8-nitro-quinoline and applying the H-Cube™ technology and yielding 520 mg (98%) of 3-cyclopropylmethoxy-6-fluoro-quinolin-8-ylamine as a yellow solid; (calculated) $C_{13}H_{13}FN_2O$ [232.2]; (found) $[M+H]^+=233$.

EXAMPLE 32

[3-((R)-5-Amino-3-methyl-3,6-dihydro-2H-[1,4] oxazin-3-yl]-4-fluoro-phenyl]-[3-(2,2,2-trifluoro-ethoxy)-quinolin-8-yl]-amine or [3-((R)-5-Amino-3-methyl-3,6-dihydro-2H-[1,4]oxazin-3-yl]-4-fluoro-phenyl]-[3-(2,2,2-trifluoro-ethoxy)-quinolin-8-yl]-amine hydrochloride With 3-(2,2,2-trifluoro-ethoxy)-quinolin-8-ylamine the [3-((R)-5-Amino-3-methyl-3,6-dihydro-2H-[1,4]oxazin-3-yl]-4-fluoro-phenyl]-[3-(2,2,2-trifluoro-ethoxy)-quinolin-8-yl]-amine; treatment with hydrochloric acid (2M) in ether yielded the corresponding hydrochloride (calculated) $C_{22}H_{20}F_4N_4O_2$ [448.42]; (found) $[M+H]^+=449$.

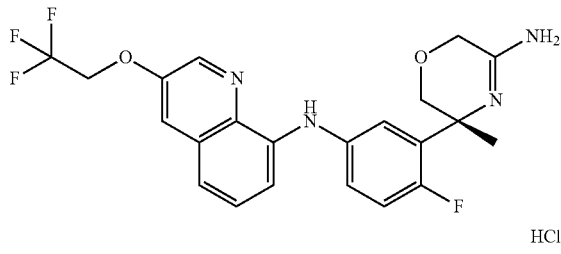 [SMILES: C[C@@]1(c2cc(Nc3cccc4cc(OCC(F)(F)F)cnc34)ccc2F)COCC(N)=N1 ; Cl]

The 3-(2,2,2-trifluoro-ethoxy)-quinolin-8-ylamine was obtained as follows:

a) 8-Nitro-3-(2,2,2-trifluoro-ethoxy)-quinoline

In a manner analogous to that described in Example 30 a) the alkylation of the 8-nitro-quinolin-3-ol (CAS25369-37-3) with methanesulfonic acid 2,2,2-trifluoro-ethyl ester yielded the title compound as a yellow solid (yield 18%); (calculated) $C_{11}H_7F_3N_2O_3$ [272.2]; (found) $[M+H]^+=273$.

b) 3-(2,2,2-Trifluoro-ethoxy)-quinolin-8-ylamine

The title compound was obtained in a manner analogous to that described in Example 29 b) starting from 8-nitro-3-(2,2,2-trifluoro-ethoxy)-quinoline (130 mg, 0.5 mmol). Applying the H-Cube™ technology yielded the 3-(2,2,2-trifluoro-ethoxy)-quinolin-8-ylamine as a yellow oil (yield 86%); (calculated) $C_{11}H_9F_3N_2O$ [242.2]; (found) $[M+H]^+=243$.

EXAMPLE 33

(R)-5-[2-Fluoro-5-(isoxazol-3-ylamino)-phenyl]-5-methyl-5,6-dihydro-2H-[1,4]oxazin-3-ylamine or (R)-5-[2-Fluoro-5-(isoxazol-3-ylamino)-phenyl]-5-methyl-5,6-dihydro-2H-[1,4]oxazin-3-ylamine trifluoroacetate With isoxazol-3-ylamine (CAS1750-42-1) the (R)-5-[2-Fluoro-5-(isoxazol-3-ylamino)-phenyl]-5-methyl-5,6-dihydro-2H-[1,4]oxazin-3-ylamine as the trifluoroacetate in the form of a light brown waxy solid; (calculated) $C_{14}H_{15}FN_4O_2$ [290.30]; (found) $[M+H]^+=291$.

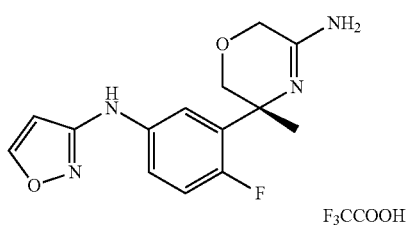

EXAMPLE 34

(S)-5-(5-(6-chloro-1-methyl-1H-indazol-3-ylamino)-2-fluorophenyl)-5-methyl-5,6-dihydro-2H-1,4-oxazin-3-amine With 6-chloro-1-methyl-1H-indazol-3-ylamine (CAS1031927-22-6) the [3-((R)-5-amino-3-methyl-3,6-dihydro-2H-[1,4]oxazin-3-yl)-4-fluoro-phenyl]-(6-chloro-1-methyl-1H-indazol-3-yl)-amine as a light grey solid; (calculated) $C_{19}H_{19}ClFN_5O$ [387.84]; (found) $[M+H]^+=388$.

EXAMPLE 35

(S)-5-[5-(5-Chloro-indan-1-ylamino)-2-fluoro-phenyl]-5-methyl-5,6-dihydro-2H-[1,4]oxazin-3-ylamine or (S)-5-[5-(5-Chloro-indan-1-ylamino)-2-fluoro-phenyl]-5-methyl-5,6-dihydro-2H-[1,4]oxazin-3-ylamine hydrochloride With (RS)-5-chloro-indan-1-ylamine (CAS67120-39-2) the (S)-5-[5-(5-Chloro-indan-1-ylamino)-2-fluoro-phenyl]-5-methyl-5,6-dihydro-2H-[1,4]oxazin-3-ylamine as an off-white solid; treatment with hydrochloric acid (2M) in ether yielded the corresponding hydrochloride (calculated) $C_{20}H_{21}ClFN_3O$ [373.86]; (found) $[M+H]^+=374$.

EXAMPLE 36-39

In a reaction sequence analogous to that described in Example 5 (method B), the following compounds were obtained starting from the palladium-catalyzed amination of building block D, (RS)-[bis-(4-methoxy-phenyl)-phenyl-methyl]-[5-(3-bromo-phenyl)-5-methyl-5,6-dihydro-2H-[1,4]oxazin-3-yl]-amine, with the corresponding amine followed by the cleavage of the protecting group with trifluoroacetic acid:

EXAMPLE 36

[3-(5-Amino-3-methyl-3,6-dihydro-2H-[1,4]oxazin-3-yl)-phenyl]-(3-chloro-6-fluoro-quinolin-8-yl)-amine or [3-(5-Amino-3-methyl-3,6-dihydro-2H-[1,4]oxazin-3-yl)-phenyl]-(3-chloro-6-fluoro-quinolin-8-yl)-amine hydrochloride With 3-chloro-6-fluoro-quinolin-8-ylamine [CAS515170-52-2, H. Gershon et al. Monatshefte für Chemie (1994), 125 (6-7), 723-30] the [3-(5-Amino-3-methyl-3,6-dihydro-2H-[1,4]oxazin-3-yl)-phenyl]-(3-chloro-6-fluoro-quinolin-8-yl)-amine; treatment with hydrochloric acid (2M) in ether yielded the corresponding hydrochloride (calculated) $C_{20}H_{18}ClFN_4O$ [384.84]; (found) $[M+H]^+=385$.

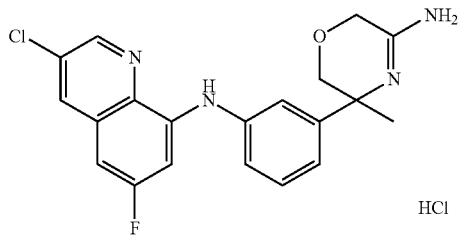 [SMILES: CC1(c2cccc(Nc3cc(F)cc4cc(Cl)cnc34)c2)COCC(N)=N1 ; Cl]

EXAMPLE 37

[3-(5-Amino-3-methyl-3,6-dihydro-2H-[1,4]oxazin-3-yl)-phenyl]-(3-methoxy-quinolin-8-yl)-amine or [3-(5-Amino-3-methyl-3,6-dihydro-2H-[1,4]oxazin-3-yl)-phenyl]-(3-methoxy-quinolin-8-yl)-amine hydrochloride With 3-methoxy-quinolin-8-ylamine the [3-(5-Amino-3-methyl-3,6-dihydro-2H-[1,4]oxazin-3-yl)-phenyl]-(3-methoxy-quinolin-8-yl)-amine; treatment with hydrochloric acid (2M) in ether yielded the corresponding hydrochloride (calculated) $C_{21}H_{22}N_4O_2$ [362.44]; (found) $[M+H]^+=363$.

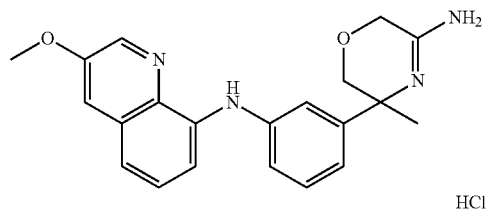 [SMILES: COc1cnc2c(Nc3cccc(C4(C)COCC(N)=N4)c3)cccc2c1 ; Cl]

The 3-methoxy-quinolin-8-ylamine was obtained as follows:

a) 8-Nitro-3-methoxy-quinoline

In a manner analogous to that described in Example 30 a) the alkylation of the 8-nitro-quinolin-3-ol (CAS25369-37-3) with iodomethane yielded the title compound as a yellow solid (yield 26%).

b) 3-Methoxy-quinolin-8-ylamine

The title compound was obtained in a manner analogous to that described in Example 29 b) starting from 8-nitro-3-methoxy-quinoline. Applying the H-Cube™ technology yielded the 3-Methoxy-quinolin-8-ylamine in 94% yield; (calculated) $C_{10}H_{10}N_2O$ [174.2]; (found) $[M+H]^+=175$.

EXAMPLE 38

[3-(5-Amino-3-methyl-3,6-dihydro-2H-[1,4]oxazin-3-yl)-phenyl]-(1,2-dimethyl-1H-benzoimidazol-5-yl)-amine With 1,2-dimethyl-1H-benzoimidazol-5-ylamine (CAS102872-45-7) the [3-(5-Amino-3-methyl-3,6-dihydro-2H-[1,4]oxazin-3-yl)-phenyl]-(1,2-dimethyl-1H-benzoimidazol-5-yl)-amine; (calculated) $C_{20}H_{23}N_5O$ [349.44]; (found) $[M+H]^+=350$.

EXAMPLE 39

5-[3-(5-Chloro-indan-1-ylamino)-phenyl]-5-methyl-5,6-dihydro-2H-[1,4]oxazin-3-ylamine or 5-[3-(5-Chloro-indan-1-ylamino)-phenyl]-5-methyl-5,6-dihydro-2H-[1,4]oxazin-3-ylamine hydrochloride With (RS)-5-chloro-indan-1-ylamine (CAS67120-39-2) the 5-[3-(5-Chloro-indan-1-ylamino)-phenyl]-5-methyl-5,6-dihydro-2H-[1,4]oxazin-3-ylamine; treatment with hydrochloric acid (2M) in ether yielded the corresponding hydrochloride (calculated) $C_{20}H_{22}ClN_3O$ [355.87]; (found) $[M+H]^+=356$, $[M+H+2]^+=358$.

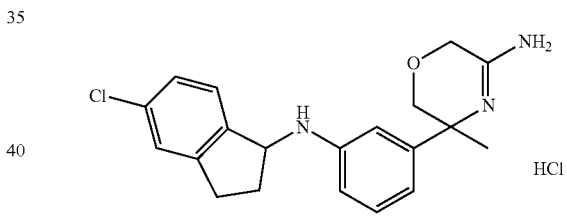

EXAMPLE 40

[3-((R)-5-Amino-3-methyl-3,6-dihydro-2H-[1,4]oxazin-3-yl)-4-fluoro-phenyl]-(3-chloro-6,7-dihydro-5H-[1]pyrindin-7-yl)-amine a) (R)-5-(5-Amino-2-fluoro-phenyl)-5-methyl-morpholin-3-one

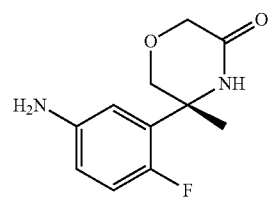

A solution of (R)-5-(5-bromo-2-fluoro-phenyl)-5-methyl-morpholin-3-one (building block B) (1.0 g, 3.47 mmol) in toluene (61 ml) was treated with benzophenonimine (1.26 g, 6.94 mmol), tris(dibenzylideneacetone)-dipalladium chloroform complex (108 mg, 0.104 mmol), 2-di-tert-butylphosphino-2',4',6'-triisopropylbiphenyl (147 mg, 0.347 mmol) and sodium tert-butoxide (1.0 g, 10.4 mmol). The mixture was heated to 105° C. and stirred at this temperature for 18 hours. Even though following TLC (silica gel; heptane:ethyl acetate=1:1) the reaction was not completed, the mixture was stirred with hydrochloric acid (1M, 50 ml) for 45 minutes. Solid sodium hydrogen carbonate was added until pH 8 was reached and the mixture was extraced with ethyl acetate. The combined organic layers were dried over sodium sulphate and evaporated at reduced pressure. The crude material was purified by flash chromatography on silica gel using a gradient of heptane/ethyl acetate=100:0 to 20:80 as the eluent. The (R)-5-(5-amino-2-fluoro-phenyl)-5-methyl-morpholin-3-one was obtained as a dark red oil (312 mg, 40%); (calculated) $C_{11}H_{13}FN_2O_2$ [224.24]; (found) [M+H]$^+$=225.

b) (R)-5-[5-((RS)-3-Chloro-6,7-dihydro-5H-[1]pyrindin-7-ylamino)-2-fluoro-phenyl]-5-methyl-morpholin-3-one

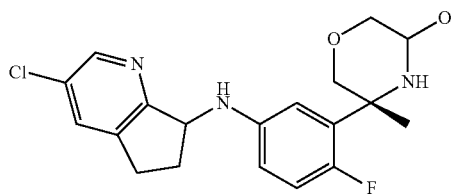 [SMILES: C[C@@]1(c2cc(NC3CCc4cc(Cl)cnc43)ccc2F)COCC(O)N1]

A solution of 3-chloro-5,6-dihydro-[1]pyrindin-7-one (34.5 mg, 0.21 mmol) and (R)-5-(5-amino-2-fluoro-phenyl)-5-methyl-morpholin-3-one (50.1 mg, 0.22 mmol) in a mixture of methanol (7.3 ml) and dichloromethane (0.9 ml) was treated with decaborane (6.9 mg, 0.21 mmol). The reaction mixture was stirred at room temperature for 22 hours. For the workup, the mixture was poured into a saturated aqueous solution of sodium hydrogen carbonate, thereafter extracted with ethyl acetate. The combined organic layers were dried over sodium sulphate, then evaporated at reduced pressure. The crude material was purified by flash chromatography on silica gel using a gradient of heptane/ethyl acetate=100:0 to 20:80 as the eluent. The (R)-5-[5-((RS)-3-chloro-6,7-dihydro-5H-[1]pyrindin-7-ylamino)-2-fluoro-phenyl]-5-methyl-morpholin-3-one was obtained as an orange solid (50 mg, 71%); (calculated) $C_{19}H_{19}ClFN_3O_2$ [375.83]; (found) [M]$^+$=376, [M+2]$^+$=378.

c) (R)-5-[5-((RS)-3-Chloro-6,7-dihydro-5H-[1]pyrindin-7-ylamino)-2-fluoro-phenyl]-5-methyl-morpholin-3-thione

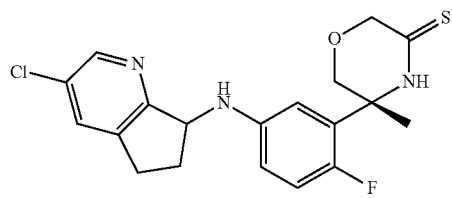 [SMILES: C[C@@]1(c2cc(NC3CCc4cc(Cl)cnc43)ccc2F)COCC(=S)N1]

A solution of (R)-5-[5-((RS)-3-chloro-6,7-dihydro-5H-[1]pyrindin-7-ylamino)-2-fluoro-phenyl]-5-methyl-morpholin-3-one (76 mg, 0.2 mmol) in dioxane (3 ml) was treated with Lawesson's reagent (53.2 mg, 0.13 mmol). The reaction mixture was stirred at 80° C. for 3 hours. For the workup, the mixture was quenched with a saturated aqueous solution of sodium hydrogen carbonate, thereafter extracted with ethyl acetate. The combined organic layers were dried over sodium sulphate, then evaporated at reduced pressure. The crude material was purified by flash chromatography on silica gel using a gradient of heptane/ethyl acetate=100:0 to 45:55 as the eluent. The (R)-5-[5-((RS)-3-chloro-6,7-dihydro-5H-[1]pyrindin-7-ylamino)-2-fluoro-phenyl]-5-methyl-morpholin-3-thione was obtained as a white solid (58 mg, 73%); (calculated) $C_{19}H_{19}ClFN_3OS$ [391.90]; (found) [M+H]$^+$=392, [M+2+H]$^+$=394.

c) [3-((R)-5-Amino-3-methyl-3,6-dihydro-2H-[1,4]oxazin-3-yl)-4-fluoro-phenyl]-((RS)-3-chloro-6,7-dihydro-5H-[1]pyrindin-7-yl)-amine In a pressure tube (R)-5-[5-((RS)-3-chloro-6,7-dihydro-5H-[1]pyrindin-7-ylamino)-2-fluoro-phenyl]-5-methyl-morpholin-3-thione (58 mg, 0.15 mmol) was dissolved in a solution of ammonia in methanol (7M, 0.5 ml). Then tert-butyl hydroperoxide (70% in water) (0.07 ml, 0.74 mmol) was added. The tube was sealed and the mixture stirred for 4 hours at room temperature. For the workup, the solution was evaporated at reduced pressure. NMR analysis showed still starting material. The residue was redissolved in a solution ammonia in methanol (7M, 0.5 ml) and heated to 50° C. for 3 days. Thereafter, another 0.5 ml were added, then after 1 day another 0.071 ml (0.74 mmol) of tert-butyl hydroperoxide. After stirring at room temperature for 4.5 hours the reaction mixture was quenched with a saturated aqueous solution of sodium carbonate, thereafter extracted with ethyl acetate. The combined organic layers were dried over sodium sulphate, then evaporated at reduced pressure. The crude material was purified by flash chromatography on silica gel using a gradient of heptane/ethyl acetate=100:0 to 0:100 as the eluent. The [3-((R)-5-amino-3-methyl-3,6-dihydro-2H-[1,4]oxazin-3-yl)-4-fluoro-phenyl]-((RS)-3-chloro-6,7-dihydro-5H-[1]pyrindin-7-yl)-amine was obtained as a white foam (33 mg, 60%); (calculated) $C_{19}H_{20}ClFN_4O$ [374.85]; (found) [M+H]$^+$=375.

The (RS)-3-chloro-6,7-dihydro-5H-[1]pyrindin-7-ylamine was prepared as follows:

a) 3-Chloro-6,7-dihydro-5H-[1]pyrindine

A solution of 5-chloro-2-(pent-4-ynyl)pyrimidine (H. C. van der Plas, Tetrahedron 1989, 45, 5151-5162) (4.95 g (27.4 mmol) in nitrobenzene (50 ml) was heated to 210° C. for 1.5 hours under a continuous stream of nitrogen. The reaction was followed by TLC (silica gel, heptane: ethyl acetate=2:1; UV detection 254 nm). After completion, the reaction mixture was purified by flash chromatography on silica gel using a gradient of heptane/ethyl acetate=100:0 to 80:20 as the eluent. The 3-chloro-6,7-dihydro-5H-[1]pyrindine was obtained as a light brown solid (3.21 g, 76%); (calculated) $C_8H_8ClN$ [153.61]; (found) [M+H]$^+$=154.

b) 3-Chloro-6,7-dihydro-5H-[1]pyrindine 1-oxide

A solution of 3-chloro-6,7-dihydro-5H-[1]pyrindine (3.03 g, 19.7 mmol) in acetic acid (19.7 ml) was treated at room temperature with hydrogen peroxide (3.45 ml, 39.5 mmol). The mixture was heated to 70° C. and stirred at this temperature overnight. After completion, the reaction mixture was allowed to cool and was concentrated at reduced pressure. Water was added and the mixture was evaporated again. This procedure was repeated another 2 times. The residue was dissolved in ethyl acetate, washed with a saturated aqueous solution of sodium hydrogen carbonate and brine, then dried over sodium sulphate and evaporated at reduced pressure. The crude 3-chloro-6,7-dihydro-5H-[1]pyrindine 1-oxide was obtained as dark green crystals (2.07 g, 62%). (calculated) $C_8H_8ClNO$ [169.61]; (found) $[M+H]^+$=170.

c) Acetic acid 3-chloro-6,7-dihydro-5H-[1]pyrindin-7-yl ester

A solution of 3-chloro-6,7-dihydro-5H-[1]pyrindine 1-oxide (2.07 g, 12.2 mmol) in acetic acid anhydride (62.2 ml, 659 mmol) was stirred at 110° C. for 20 hours. For the workup, the solvent was removed at reduced pressure and the residue quenched with saturated aqueous solution of sodium hydrogen carbonate. The aqueous phase was extracted with dichloromethane, the resulting organic layers combined and dried over sodium sulphate. After evaporation of the solvent, the residue was purified by flash chromatography on silica gel using a gradient of heptane/ethyl acetate=100:0 to 70:30 as the eluent. The acetic acid 3-chloro-6,7-dihydro-5H-[1]pyrindin-7-yl ester was obtained as a red liquid (1.57 g, 61%); (calculated) $C_{10}H_{10}ClNO_2$ [211.65]; (found) $[M+H]^+$=212.

d) 3-Chloro-6,7-dihydro-5H-[1]pyrindin-7-ol

A solution of acetic acid 3-chloro-6,7-dihydro-5H-[1]pyrindin-7-yl ester (1.57 g, 7.42 mmol) in methanol (35.7 ml) was treated with 1M sodium hydroxide (8.9 ml). The mixture was stirred at room temperature for 1.5 hours. The reaction was followed by TLC (silica gel, heptane: ethyl acetate=1:1; UV detection 254 nm). After completion, the reaction mixture was treated with water and extracted with dichloromethane. The combined organic layers were dried over sodium sulphate, then evaporated leaving a dark red liquid (1.15 g, 91%) which crystallised on standing. Following NMR the product was pure enough for the next step of the synthesis; (calculated) $C_8H_8ClNO$ [169.61]; (found) $[M+H]^+$=170.

e) 3-Chloro-5,6-dihydro-[1]pyrindin-7-one

A solution of 3-chloro-6,7-dihydro-5H-[1]pyrindin-7-ol (570 mg, 3.36 mmol) in dimethylsulphoxide (17.7 ml) was treated at room temperature with triethylamine (2.81 ml, 20.2 mmol) followed by sulphur trioxide-pyridine complex (1.6 g, 10.1 mmol). The solution was stirred at room temperature for 1 hour. After completion, the reaction mixture was treated with water and extracted with dichloromethane. The combined organic layers were dried over sodium sulphate, then evaporated leaving a dark red liquid. The crude material was purified by flash chromatography on silica gel using a gradient of heptane/ethyl acetate=70:30 to 30:70 as the eluent. The 3-chloro-5,6-dihydro-[1]pyrindin-7-one was obtained as a pink solid (472 mg, 84%); (calculated) $C_8H_6ClNO$ [167.60]; (found) $[M+H]^+$=168.

EXAMPLES 41-43

In a reaction sequence analogous to that described in Example 5 (method B), the following compounds were obtained starting from the palladium-catalyzed amination of building block E, (RS)-[bis-(4-methoxy-phenyl)-phenyl-methyl]-[5-(3-bromo-phenyl)-5-methyl-5,6-dihydro-2H-[1,4] oxazin-3-yl]-amine, with the corresponding amine followed by the cleavage of the protecting group with trifluoroacetic acid:

EXAMPLE 41

(R)-5-{5-[2-(2,2-Difluoro-ethoxy)-phenylamino]-2-fluoro-phenyl}-5-methyl-5,6-dihydro-2H-[1,4]oxazin-3-ylamine or (R)-5-{5-[2-(2,2-Difluoro-ethoxy)-phenylamino]-2-fluoro-phenyl}-5-methyl-5,6-dihydro-2H-[1,4]oxazin-3-ylamine hydrochloride With 2-(2,2-difluoro-ethoxy)-phenylamine [CAS937606-78-5] the (R)-5-{5-[2-(2,2-Difluoro-ethoxy)-phenylamino]-2-fluoro-phenyl}-5-methyl-5,6-dihydro-2H-[1,4]oxazin-3-ylamine hydrochloride; (calculated) $C_{19}H_{20}F_3N_3O_2$ [379.39]; (found) $[M+H]^+$=380.

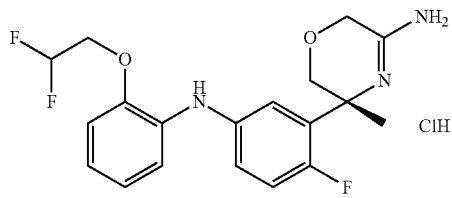 [SMILES: C[C@@]1(c2cc(Nc3ccccc3OCC(F)F)ccc2F)COCC(N)=N1 ; Cl]

EXAMPLE 42

(R)-5-{2-Fluoro-5-[2-(2,2,2-trifluoro-ethoxy)-phenylamino]-phenyl}-5-methyl-5,6-dihydro-2H-[1,4] oxazin-3-ylamine or (R)-5-{2-Fluoro-5-[2-(2,2,2-trifluoro-ethoxy)-phenylamino]-phenyl}-5-methyl-5,6-dihydro-2H-[1,4]oxazin-3-ylamine hydrochloride With 2-(2,2,2-trifluoro-ethoxy)-phenylamine [CAS57946-60-8] the (R)-5-{2-Fluoro-5-[2-(2,2,2-trifluoro-ethoxy)-phenylamino]-phenyl}-5-methyl-5,6-dihydro-2H-[1,4]oxazin-3-ylamine hydrochloride; (calculated) $C_{19}H_{19}F_4N_3O_2$ [397.38]; (found) $[M+H]^+$=398.

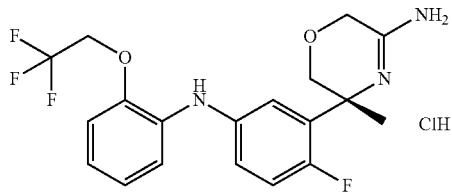 [SMILES: C[C@@]1(c2cc(Nc3ccccc3OCC(F)(F)F)ccc2F)COCC(N)=N1 ; Cl]

EXAMPLE 43

(R)-5-{2-Fluoro-5-[2-(2-fluoro-ethoxy)-phenylamino]-phenyl}-5-methyl-5,6-dihydro-2H-[1,4] oxazin-3-ylamine or (R)-5-{2-Fluoro-5-[2-(2-fluoro-ethoxy)-phenylamino]-phenyl}-5-methyl-5,6-dihydro-2H-[1,4]oxazin-3-ylamine hydrochloride With 2-(2-fluoro-ethoxy)-phenylamine [CAS1547-11-1] the (R)-5-{2-Fluoro-5-[2-(2-fluoro-ethoxy)-phenylamino]-phenyl}-5-methyl-5,6-dihydro-2H-[1,4]oxazin-3-ylamine hydrochloride; (calculated) $C_{19}H_{21}F_2N_3O_2$ [361.39]; (found) $[M+H]^+$=362.

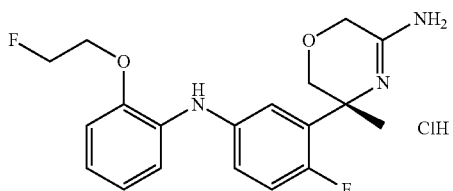
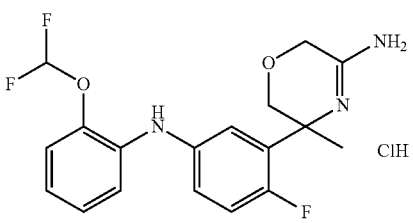 [SMILES: CC1(c2cc(Nc3ccccc3OC(F)F)ccc2F)COCC(N)=N1 ; Cl]

The 2-(2,2-difluoro-ethoxy)-phenylamine was obtained as follows:

a) 1-(2,2-Difluoro-ethoxy)-2-nitro-benzene

In a microwave tube a mixture of 1-fluoro-2-nitrobenzene (100 mg, 0.7 mmol), potassium carbonate (193 mg, 1.4 mmol), and 2,2-difluoroethanol in N,N-dimethylformamide (2 ml) was heated in a microwave oven at 120° C. for 20 minutes. For the workup, the reactrion mixture was poured into water (5 ml). The precipitated product was filtered and the aqueous layer was extracted with ether. The combined organic layers were dried and evaporated to yield together with the precipitated material 130 mg (85%) of the 1-(2,2-difluoro-ethoxy)-2-nitro-benzene which was sufficiently pure to be engaged in the next step without further purification; (calculated) $C_8H_7F_2NO_3$ [203.15]; (found) $[M+H]^+$=204.

b) 2-(2,2-Difluoro-ethoxy)-phenylamine

The 1-(2,2-difluoro-ethoxy)-2-nitro-benzene (2.16 mmol) was dissolved in a 1:1-mixture of ethanol and ethyl acetate in order to obtain a final concentration of 0.05M. Hydrogenation was performed at 60° C., 1 bar of hydrogen and with palladium on charcoal (10%) as the catalyst. After evaporation of the solvent the title compound was obtained in 90% yield and could be used in the next step without further purification; (calculated) $C_8H_9F_2NO$ [173.16]; (found) $[M+H]^+$=174.

In close analogy to the aforementioned reaction sequence the 2-(2,2,2-trifluoro-ethoxy)-phenylamine and the 2-(2-fluoro-ethoxy)-phenylamine were obtained.

EXAMPLE 44

5-[3-(2-Difluoromethoxy-phenylamino)-phenyl]-5-methyl-5,6-dihydro-2H-[1,4]oxazin-3-ylamine or 5-[3-(2-Difluoromethoxy-phenylamino)-phenyl]-5-methyl-5,6-dihydro-2H-[1,4]oxazin-3-ylamine hydrochloride In a reaction sequence analogous to that described in Example 5 (method B), the palladium-catalyzed amination of building block F, (RS)-[bis-(4-methoxy-phenyl)-phenyl-methyl]-[5-(3-bromo-phenyl)-5-methyl-5,6-dihydro-2H-[1,4] oxazin-3-yl]-amine, with 2-difluoromethoxy-phenylamine (CAS22236-04-0) followed by the cleavage of the protecting group with trifluoroacetic acid yielded the 5-[3-(2-Difluoromethoxy-phenylamino)-phenyl]-5-methyl-5,6-dihydro-2H-[1,4]oxazin-3-ylamine hydrochloride; (calculated) $C_{18}H_{219}F_2N_3O_2$ [347.37]; (found) $[M+H]^+$=348.

EXAMPLE 45

(R)-5-{5-[(4-Chloro-1-difluoromethyl-1H-pyrazol-3-ylmethyl)-amino]-2-fluoro-phenyl}-5-methyl-5,6-dihydro-2H-[1,4]oxazin-3-ylamine a) (R)-5-[5-(Benzhydrylidene-amino)-2-fluoro-phenyl]-5-methyl-morpholin-3-one

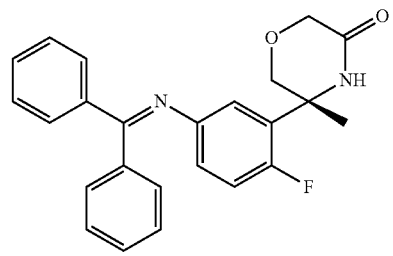 [SMILES: C[C@@]1(c2cc(N=C(c3ccccc3)c3ccccc3)ccc2F)COCC(=O)N1]

Under a nitrogen atmosphere a solution of (R)-5-(5-bromo-2-fluoro-phenyl)-5-methyl-morpholin-3-one (building block B) (1.2 g, 4.17 mmol) in toluene (20 ml) was treated with benzophenonimine (1.59 g, 8.33 mmol), tris(dibenzylideneacetone)-dipalladium chloroform complex (133 mg, 0.125 mmol), tert-butyl X-phos (182 mg, 0.417 mmol) and sodium tert-butoxide (1.24 g, 12.5 mmol). The mixture was stirred in a sealed tube at 105° C. for 18 hours. For the workup, the brown reaction mixture was evaporated and the residue directly purified by flash chromatography on a silica-amine phase using a gradient of heptane/ethyl acetate=100:0 to 40:60 as the eluent. The (R)-5-[5-(benzhydrylidene-amino)-2-fluoro-phenyl]-5-methyl-morpholin-3-one was obtained as a yellow solid (1.53 g, 95%); (calculated) $C_{24}H_{21}FN_2O_2$ [388.45]; (found) $[M+H]^+$=389.

b) (R)-5-[5-(Benzhydrylidene-amino)-2-fluoro-phenyl]-5-methyl-morpholin-3-thione

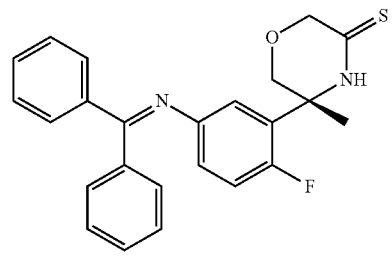 [SMILES: C[C@@]1(c2cc(N=C(c3ccccc3)c3ccccc3)ccc2F)COCC(=S)N1]

A solution of (R)-5-[5-(benzhydrylidene-amino)-2-fluoro-phenyl]-5-methyl-morpholin-3-one (1.53 g, 3.94 mmol) in dioxane (30 ml) was treated with Lawesson's reagent (1.3 g, 3.15 mmol). The orange coloured suspension was heated in a sealed tube at 80° C. for 18 hours. For the workup, the meanwhile green coloured reaction mixture was evaporated at reduced pressure and the residue directly purified by flash chromatography on a silica-amine phase using a gradient of heptane/ethyl acetate=100:0 to 40:60 as the eluent. The (R)-5-[5-(benzhydrylidene-amino)-2-fluoro-phenyl]-5-methyl-morpholin-3-thione was obtained as a yellow solid (0.803 g, 50%); (calculated) $C_{24}H_{21}FN_2OS$ [404.51]; (found) $[M+H]^+=405$.

c) (R)-5-(5-Amino-2-fluoro-phenyl)-5-methyl-morpholine-3-thione Hydrochloride

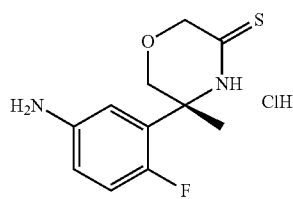 [SMILES: C[C@@]1(c2cc(N)ccc2F)COCC(=S)N1 ; Cl]

A solution of (R)-5-[5-(benzhydrylidene-amino)-2-fluoro-phenyl]-5-methyl-morpholin-3-thione (0.795 g, 1.97 mmol) in dioxane (10 ml) was treated dropwise at room temperature with hydrochloric acid (1M). The yellow reaction mixture was stirred at room temperature overnight. For the workup, the solution was evaporated at reduced pressureand. The yellow oil was dissolved in ether (15 ml), and the solution was extracted with hydrochloric acid (1M, 15 ml). The aqueous layer was extracted with ether (15 ml), then the combined organic layers were extracted with hydrochloric acid (1M, 5 ml). The combined aqueous layers were evaporated at reduced pressure and yielded the (R)-5-(5-amino-2-fluoro-phenyl)-5-methyl-morpholine-3-thione hydrochloride as a yellow solid (0.47 g, 87%) which was pure enough to be engaged in the next step without further purification; (calculated) $C_{11}H_{13}FN_2OS$ [240.30]; (found) $[M+H]^+=241$.

d) (R)-5-{5-[(4-Chloro-1-difluoromethyl-1H-pyrazol-3-ylmethyl)-amino]-2-fluoro-phenyl}-5-methyl-morpholine-3-thione

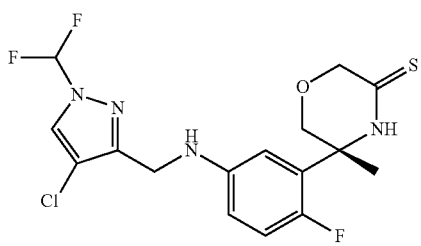 [SMILES: C[C@@]1(c2cc(NCc3nn(C(F)F)cc3Cl)ccc2F)COCC(=S)N1]

In a 5 ml-reaction tube under an inert atmosphere a mixture of (R)-5-(5-amino-2-fluoro-phenyl)-5-methyl-morpholine-3-thione (48 mg, 0.2 mmol) and 4-chloro-1-difluoromethyl-1H-pyrazole-3-carbaldehyde (20 mg, 0.11 mmol) in methanol (0.3 ml) was stirred at room temperature for 1 hour. Then decaborane (24 mg, 0.2 mmol) was added in one portion and the mixture warmed to 45° C. for 15 hours. For the workup, the light yellow solution was quenched with sodium carbonate (10% solution), the methanol removed at reduced pressure and then the residue extracted three times with ethyl acetate. The combined organic layers were dried over sodium sulphate, then evaporated at reduced pressure. The crude product was purified by preparative HPLC using a gradient of water (+0.1% triethylamine) and acetonitrile (90:10 to 10:90). The (R)-5-{5-[(4-chloro-1-difluoromethyl-1H-pyrazol-3-ylmethyl)-amino]-2-fluoro-phenyl}-5-methyl-morpholine-3-thione was obtained as a colourless foam (49 mg, 60%); (calculated) $C_{16}H_{16}ClF_3N_4OS$ [404.84]; (found) $[M+H]^+=405$.

e) (R)-5-{5-[(4-Chloro-1-difluoromethyl-1H-pyrazol-3-ylmethyl)-amino]-2-fluoro-phenyl}-5-methyl-5,6-dihydro-2H-[1,4]oxazin-3-ylamine In a manner analogous to that described in Example 40c) the ammonolysis of the (R)-5-{5-[(4-chloro-1-difluoromethyl-1H-pyrazol-3-ylmethyl)-amino]-2-fluoro-phenyl}-5-methyl-morpholine-3-thione in presence of tert-butyl hydroperoxide yielded the title compound as a colourless foam; (calculated) $C_{16}H_{17}ClF_3N_5O$ [387.79]; (found) $[M+H]^+=388$.

The 4-chloro-1-difluoromethyl-1H-pyrazole-3-carbaldehyde was obtained as follows:

a) 1-Difluoromethyl-1H-pyrazole-3-carboxylic acid methyl ester

A solution of 1-difluoromethyl-1H-pyrazole-3-carboxylic acid (CAS925179-02-8) (500 mg, 3.1 mmol) in methanol (18 ml) was cooled to 0° C. and treated with sulphuric acid (98%, 0.2 ml, 3.1 mmol). The mixture was heated to reflux for 2 hours. For the workup, the solution was cooled and concentrated at reduced pressure. The residue was partitioned between ethyl acetate (25 ml) and water (30 ml). The organic layer was separated, washed with water until the water phase showed a neutral pH. After drying over sodium sulphate, the organic layer was evaporated at reduced pressure. The 1-difluoromethyl-1H-pyrazole-3-carboxylic acid methyl ester was obtained as a colorless liquid (535 mg, 99%) pure enough to be engaged in the next step without further purification; (calculated) $C_6H_6F_2N_2O_2$ [176.12]; (found) $[M+H]^+=177$.

b) 4-Chloro-1-difluoromethyl-1H-pyrazole-3-carboxylic acid methyl ester

A mixture of 1-difluoromethyl-1H-pyrazole-3-carboxylic acid methyl ester (535 mg, 3 mmol) and N-chloro-succinimide (1.22 g, 9.1 mmol) in N,N-dimethylformamide (5 ml) was heated at 50° C. overnight. The reaction mixture was cooled, poured into water (20 ml), then extracted with ethyl acetate. The organic layer was separated, washed with water, dried over sodium sulphate, finally evaporated at reduced pressure. The yellowish crude material was purified by chromatography on silica gel using a 3:1-mixture of cyclohexane and ethyl acetate as the eluent. The 4-chloro-1-difluoromethyl-1H-pyrazole-3-carboxylic acid methyl ester was obtained as a white solid (540 mg, 84%); (calculated) $C_6H_5ClF_2N_2O_2$ [210.57]; (found) $[M]^+=210$.

c) 4-Chloro-1-difluoromethyl-1H-pyrazole-3-carboxylic acid

A solution of 4-chloro-1-difluoromethyl-1H-pyrazole-3-carboxylic acid methyl ester (540 mg, 2.6 mmol) in tetrahydrofuran (18 ml) was treated at room temperature with a solution of lithium hydroxide (135 mg, 5.6 mmol) in a 1:1-mixture of water and methanol (12 ml). After 1 hour the reaction was complete, and the solvents were evaporated at reduced pressure. The residue was dissolved in water (10 ml) and acidified with hydrochloric acid (2M). Extraction with ethyl acetate, drying of the organic layer over sodium sulphate, and evaporation at reduced pressure yielded a white solid (555 mg) which was triturated with pentane (10 ml). The solid material was filtered, washed with pentane and dried. After drying at reduced pressure the 4-chloro-1-difluoromethyl-1H-pyrazole-3-carboxylic acid was obtained as a white solid (477 mg, 95%); (calculated) $C_5H_3ClF_2N_2O_2$ [196.540]; (found) $[M'H]^-=195$.

d) 4-Chloro-1-difluoromethyl-1H-pyrazole-3-carboxylic acid methoxy-methyl-amide A suspension of 4-chloro-1-difluoromethyl-1H-pyrazole-3-carboxylic acid (880 mg, 4.5 mmol) and N,O-dimethylhydroxylamine hydrochloride (459 mg, 4.7 mmol) in dichloromethane (30 ml) was treated at room temperature with N-methylmorpholine (476 mg, 4.7 mmol). Thereafter, in three portions 1-ethyl-3-(3-dimethylaminopropyl)carbodiimide hydrochloride (901 mg, 4.7 mmol) was added. The solution was stirred at room temperature overnight. For the workup, the reaction mixture was treated dropwise with hydrochloric acid (1M, 30 ml) and stirred for 10 minutes. The organic layer was separated, washed with water, then dried over sodium sulphate and evaporated. The crude material was purified by chromatography on silica gel using a 2:1-mixture of cyclohexane and ethyl acetate as the eluent. The 4-chloro-1-difluoromethyl-1H-pyrazole-3-carboxylic acid methoxy-methyl-amide was obtained as a colourless oil (930 mg, 87%).

e) 4-Chloro-1-difluoromethyl-1H-pyrazole-3-carbaldehyde

A solution of 4-chloro-1-difluoromethyl-1H-pyrazole-3-carboxylic acid methoxy-methyl-amide (930 mg, 3.9 mmol) in tetrahydrofuran (30 ml) was cooled to 0° C. and treated dropwise with a solution of lithium aluminium hydride in tetrahydrofuran (1M, 2 ml). Stirring was continued at 0° C. for 45 minutes. In order to complete the reaction, another 2 ml of the solution of lithium aluminium hydride in tetrahydrofuran (1M) was added. After 45 minutes the reaction mixtures was cooled to −15° C. and a saturated solution of potassium hydrogensulphate (25 ml) was added dropwise. Stirring was continued at −15° C. for 10 minutes, then ether (30 ml) was added and again stirred for 30 minutes. Thereafter, the reaction mixture was left to warm to room temperature, the organic layer separated, washed with water, finally dried over sodium sulphate and evaporated. The crude material was purified by chromatography on silica gel using a 4:1-mixture of cyclohexane and ethyl acetate as the eluent. The 4-chloro-1-difluoromethyl-1H-pyrazole-3-carbaldehyde was obtained as a colourless oil (582 mg, 83%).

EXAMPLE 46

[3-(5-Amino-3-methyl-3,6-dihydro-2H-[1,4]oxazin-3-yl)-phenyl]-(2-cyclopropyl-benzooxazol-4-yl)-amine or [3-(5-Amino-3-methyl-3,6-dihydro-2H-[1,4]oxazin-3-yl)-phenyl]-(2-cyclopropyl-benzooxazol-4-yl)-amine hydrochloride

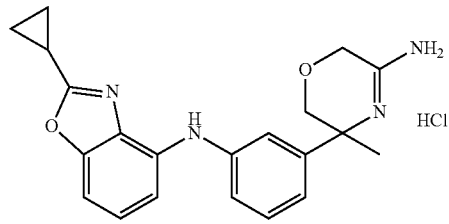 [SMILES: CC1(c2cccc(Nc3cccc4oc(C5CC5)nc34)c2)COCC(N)=N1 ; Cl]

In a reaction sequence analogous to that described in Example 5 (method B), the palladium-catalyzed amination of building block D, (RS)-[bis-(4-methoxy-phenyl)-phenyl-methyl]-[5-(3-bromo-phenyl)-5-methyl-5,6-dihydro-2H-[1,4]oxazin-3-yl]-amine, with 2-cyclopropyl-benzooxazol-4-ylamine [CAS 1159546] followed by the cleavage of the protecting group with trifluoroacetic acid yielded the title compound; purification on a SCX-cartridge, elution with a 1:1-mixture of dichloromethane and methanol followed by ammonia in methanol (2 M), and, finally treatment with hydrochloric acid (calculated) $C_{21}J_{22}N_4O_2$ [362.44]; (found) $[M+H]^+=363$.

The invention claimed is:
1. A compound of formula I

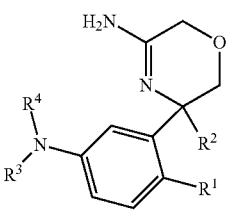

wherein
R1 is selected from the group consisting of
i) hydrogen,
ii) halogen, and
iii) $C_{1-6}$-alkyl,
$R^2$ is $C_{1-6}$-alkyl,
$R^3$ is selected from the group consisting of
i) aryl,
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
iii) aryl-$C_{1-6}$-alkyl,
iv) aryl-$C_{1-6}$-alkyl, wherein the aryl is substituted by 1-4 substituents individually selected from cyano, cyano-$C_{1-6}$-alkyl, halogen, halogen-$C_{1-6}$-alkoxy, halogen-1 $C_{1-6}$-alkyl, $C_{1-6}$-alkoxy, $C_{1-6}$-alkoxy- $C_{1-6}$-alkyl and $C_{1-6}$-alkyl, v) heteroaryl,
vi) heteroaryl substituted by 1-4 substituents individually selected from amido, cyano, cyano-$C_{1-6}$-alkyl, $C_{3-7}$-cycloalkyl, $C_{3-7}$-cycloalkyl-$C_{2-6}$-alkenyl, $C_{3-7}$-cycloalkyl-$C_{2-6}$-alkynyl, $C_{3-7}$-cycloalkyl-$C_{1-6}$-alkyl, $C_{3-7}$-cycloalkyl-$C_{1-6}$-alkoxy, halogen, halogen-$C_{1-6}$-alkoxy, halogen-$C_{1-6-alkyl}$, $C_{1-6}$-alkoxy, $C_{1-6}$-alkoxy-$C_{1-6}$-alkyl, $C_{2-6}$-alkenyl, $C_{2-6}$-alkynyl, $C_{1-6}$-alkyl and nitro,
vii) heteroaryl-$C_{1-6}$-alkyl,
viii) heteroaryl-$C_{1-6}$-alkyl, wherein the heteroaryl is substituted by 1-4 substituents individually selected from amido, cyano, cyano-$C_{1-6}$-alkyl, $C_{3-7}$-cycloalkyl, $C_{3-7}$-cycloalkyl-$C_{2-6}$-alkenyl, $C_{3-7}$-cycloalkyl-$C_{2-6}$-alkynyl, $C_{3-7}$-cycloalkyl-$C_{1-6}$-alkyl, $C_{3-7}$-cycloalkyl-$C_{1-6}$-alkoxy, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl, $C_{1-6}$-alkyl and nitro,
ix) $C_{1-6}$-alkyl,
x) $C_{1-6}$-alkyl substituted by 1-5 substituents individually selected from cyano, halogen, ydroxyl, $C_{1-6}$-alkyl—S— and $C_{1-6}$-alkoxy,
xi) $C_{3-7}$-cycloalkyl,
xii) $C_{3-7}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, ydroxyl, $C_{1-6}$-alkoxy, $C_{1-6}$-alkoxy-$C_{1-6}$-alkyl and $C_{1-6}$-alkyl,
xiii) $C_{3-7}$-cycloalkyl-$C_{1-6}$-alkyl,
xiv) $C_{3-7}$-cycloalkyl-$C_{1-6}$-alkyl, wherein the $C_{3-7}$-cycloalkyl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
xv) heterocyclyl,
xvi) heterocyclyl substituted by 1-4 substituents individually selected from ano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
xvii) heterocyclyl-$C_{1-6}$-alkyl, and
xviii) heterocyclyl-$C_{1-6}$-alkyl, wherein the heterocyclyl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-1 alkyl; and
$R^4$ is hydrogen;
or a pharmaceutically acceptable salt thereof.

2. The compound of claim 1, wherein
$R^1$ is selected from the group consisting of
i) hydrogen and
ii) halogen;
$R^2$ is $C_{1-6}$-alkyl;
$R^3$ is selected from the group consisting of
i) aryl substituted by 1-2 substituents individually halogen and halogen-$C_{1-6}$-alkoxy,
ii) aryl-$C_{1-6}$-alkyl, wherein the aryl is substituted by 1-2 halogen,
iii) heteroaryl,
iv) heteroaryl substituted by 1-2 substituents individually selected from $C_{3-7}$-cycloalkyl, $C_{3-7}$-cycloalkyl-$C_{1-6}$-alkoxy, halogen, halogen-$C_{1-6}$-alkoxy, $C_{1-6}$-alkoxy and $C_{1-6}$-alkyl,
v) heteroaryl-$C_{1-6}$-alkyl, wherein the heteroaryl is substituted by 1-2 substituents individually selected from halogen and $C_{1-6}$-alkyl,
vi) $C_{1-6}$-alkyl,
vii) $C_{1-6}$-alkyl substituted by 1-5 halogen or $C_{1-6}$-alkyl—S—,
viii) $C_{3-7}$-cycloalkyl,
ix) $C_{3-7}$-cycloalkyl substituted by 1-2 substituents individually selected from hydroxy and $C_{1-6}$-alkyl,
x) $C_{3-7}$-cycloalkyl-$C_{1-6}$-alkyl,
xi) heterocyclyl, and
xii) heterocyclyl-$C_{1-6}$-alkyl; and
$R^4$ is hydrogen.

3. The compound of claim 1, wherein $R^1$ is halogen.
4. The compound of claim 3, wherein $R^1$ is F.
5. The compound of claim 1, wherein $R^1$ is hydrogen.
6. The compound of claim 1, wherein $R^2$ is methyl.
7. The compound of claim 1, wherein $R^3$ is selected from the group consisting of
i) aryl substituted by 1-2 substituents individually selected from halogen and halogen-$C_{1-6}$-alkoxy,
ii) aryl-$C_{1-6}$-alkyl, wherein the aryl is substituted by 1-2 halogen,
iii) heteroaryl,
iv) heteroaryl substituted by 1-2 substituents individually selected from $C_{3-7}$-cycloalkyl, $C_{3-7}$-cycloalkyl-$C_{1-6}$-alkoxy, halogen, halogen-$C_{1-6}$-alkoxy, $C_{1-6}$- alkoxy and $C_{1-6}$-alkyl,
v) heteroaryl-$C_{1-6}$-alkyl, wherein the heteroaryl is substituted by 1-2 substituents individually selected from halogen and halogen-$C_{1-6}$-alkyl,
vi) $C_{1-6}$-alkyl,
vii) $C_{1-6}$-alkyl substituted by 1-5 halogen or $C_{1-6}$-alkyl—S—,
viii) $C_{3-7}$-cycloalkyl,
ix) $C_{3-7}$-cycloalkyl substituted by 1-2 substituents individually selected from hydroxy and $C_{1-6}$-alkyl,
x) $C_{3-7}$-cycloalkyl-$C_{1-6}$-alkyl,
xi) heterocyclyl, and
xii) heterocyclyl-$C_{1-6}$-alkyl.

8. The compound of claim 1, wherein $R^3$ is selected from the group consisting of
i) aryl substituted by 1-2 substituents individually selected from halogen and halogen-$C_{1-6}$-alkoxy,
ii) $C_{3-7}$-cycloalkyl,
iii) heteroaryl substituted by 1-2 substituents individually selected from halogen and $C_{1-6}$-alkoxy, and
iv) heteroaryl-$C_{1-6}$-alkyl, wherein the heteroaryl is substituted by 1-2 substituents individually selected from halogen and halogen-$C_{1-6}$-alkyl.

9. The compound of claim 1, wherein $R^3$ is selected from the group consisting of
i) benzyl substituted by 1 or 2 chloro,
ii) phenyl-CH(CH3)-, wherein the phenyl is substituted by chloro,
iii) phenyl substituted by difluoromethoxy, 2-fluoro-ethoxy, 2,2-difluoro-ethoxy or 2,2,2-trifluoro-ethoxy,
iv) ethyl substituted by 1 or 2 or 3 fluoro,
v) propyl substituted by 1 or 2 or 3 or 4 or 5 fluoro,
vi) propyl substituted —S—CH3,
vii) butyl,
viii) isopentyl,
ix) 2-ethyl-propyl,
x) 1,2-dimethyl-propyl,
xi) cyclopropyl unsubstituted or substituted by OH,
xii) cyclobutyl,
xiii) cyclopentyl substituted by OH,
xiv) cyclohexyl,
xv) bicyclo[2.2.1]heptanyl substituted by 1 or 2 methyl,
xvi) tetrahydrofuranyl,
xvii) cyclopropyl-$CH_2$-,
xviii) tetrahydrofuranyl-$CH_2$-,
xix) pyridinyl-CH(CH(CH3)$_2$)-, wherein the pyridinyl is substituted by chloro, xx) quinolinyl unsubstituted or substituted by 1 or 2 chloro, fluoro and chloro, difluoromethoxy, 2-fluoro-ethoxy, fluoro and cyclopropylmethoxy, 2,2,2-trifluoro-ethoxy or methoxy, xxi) isoxazolyl, xxii) 1H-indazolyl substituted by chloro and methyl, xxiii) indanyl substituted by chloro, xxiv) 1H-benzoimidazolyl substituted by 1 or 2 methyl, xxv) 6,7-dihydro-5H-[1]pyridinyl substituted by chloro, xxvi) 1H-pyrazolyl substituted by difluoromethyl and chloro, and xxvii) benzoxazolyl substituted by cyclopropyl.

10. The compound of claim 9, wherein $R^3$ is selected from the group consisting of i) phenyl substituted by 2,2-difluoro-ethoxy,
ii) cyclopropyl,
iii) quinolinyl substituted by chloro,
iv) quinolinyl substituted by chloro and fluoro,
v) quinolinyl substituted by methoxy,
vi) indanyl substituted by chloro, and
vii) 1H-pyrazolyl substituted by difluoromethyl and chloro.

11. The compound of claim 1, selected from the group consisting of

5-[3-(3-Chloro-benzylamino)-phenyl]-5-methyl-5,6-dihydro-2H-[1,4]oxazin-3-ylamine, (1R,2S)-2-(3-((R)-5-amino-3-methyl-3,6-dihydro-2H-1,4-oxazin-3-yl)-4-fluorophenylamino)cyclopentanol, (1S,2S)-2-(3-((R)-5-amino-3-methyl-3,6-dihydro-2H-1,4-oxazin-3-yl)-4-fluorophenylamino)cyclopentanol, (5R)-5-(2-fluoro-5-(3-methylbutan-2-ylamino)phenyl)-5-methyl-5,6-dihydro-2H-1,4-oxazin-3-amine, (R)-5-(2-fluoro-5-(((R)-tetrahydrofuran-2-yl)methylamino)phenyl)-5-methyl-5,6-dihydro-2H-1,4-oxazin-3-amine, (R)-5-(2-fluoro-5-(2,2,2-trifluoroethylamino)phenyl)-5-methyl-5,6-dihydro-2H-1,4-oxazin-3-amine, (R)-5-(2-fluoro-5-(2,2,3,3,3-pentafluoropropylamino)phenyl)-5-methyl-5,6-dihydro-2H-1,4-oxazin-3-amine, (R)-5-(2-fluoro-5-(3-(methylthio)propylamino)phenyl)-5-methyl-5,6-dihydro-2H-1,4-oxazin-3-amine, and (R)-5-(2-fluoro-5-(3,3,3-trifluoropropylamino)phenyl)-5-methyl-5,6-dihydro-2H-1,4-oxazin-3-amine, or a pharmaceutical acceptable salt thereof.

12. The compound of claim 1, selected from the group consisting of (R)-5-(2-fluoro-5-(isopentylamino)phenyl)-5-methyl-5,6-dihydro-2H-1,4-oxazin-3-amine, (R)-5-(2-fluoro-5-(pentan-3-ylamino)phenyl)-5-methyl-5,6-dihydro-2H-1,4-oxazin-3-amine, 5-[(R)-5-(((1R,2R,4R)-7,7-dimethyl-bicyclo[2.2.1]hept-2-ylamino)-2-fluoro-phenyl]-5-methyl-5,6-dihydro-2H-[1,4]oxazin-3-ylamine, (R)-5-(5-((4-chloro-1-(difluoromethyl)-1H-pyrazol-3-yl)methylamino)-2-fluorophenyl)-5-methyl-5,6-dihydro-2H-1,4-oxazin-3-amine, (R)-5-[5-(2,2-Difluoro-ethylamino)-2-fluoro-phenyl]-5-methyl-5,6-dihydro-2H-[1,4]oxazin-3-ylamine, (R)-5-(5-(butylamino)-2-fluorophenyl)-5-methyl-5,6-dihydro-2H-1,4-oxazin-3-amine, (R)-5-(5-(cyclohexylamino)-2-fluorophenyl)-5-methyl-5,6-dihydro-2H-1,4-oxazin-3-amine, (R)-5-(5-(cyclopentylamino)-2-fluorophenyl)-5-methyl-5,6-dihydro-2H-1,4-oxazin-3-amine, and (R)-5-(5-(cyclopropylmethylamino)-2-fluorophenyl)-5-methyl-5,6-dihydro-2H-1,4-oxazin-3-amine, or a pharmaceutical acceptable salt thereof.

13. The compound of claim 1, selected from the group consisting of (R)-5-(5-Cyclobutylamino-2-fluoro-phenyl)-5-methyl-5,6-dihydro-2-[1,4]oxazin-3-ylamine, (R)-5[2-Fluoro-5-(isoxazol-3-ylamino)-phenyl]-5-methyl-5,6-dihydro-2H-[1,4]oxazin-3-ylamine, (R)-5[-2-Fluoro-5-(tetrahydro-furan-3-ylamino)-phenyl]-5-methyl--5,6-dihydro-2H-[1,4]oxazin-3-ylamine, (R)-5-{2-Fluoro-5[-2-(2,2,2-trifluoro-ethoxy)-phenylamino]-phenyl}-5-methyl-5,6-dihydro-2H-[1,4]oxazin-3-ylamine, (R)-5-{2-Fluoro-5-[-2-(2-fluoro-ethoxy)-phenylamino]-phenyl}-5-methyl-5,6-dihydro-2H-[1,4]oxazin-3-ylamine, (R)-5-{5-[1-(5-Chloro-pyridin-2-yl)-2-methyl-propylamino]-2-fluoro-phenyl}-5-methyl-5,6-dihydro-2H-[1,4]oxazin-3-ylamine, (R)-5-{5[2-(2,2-Difluoro-ethoxy)-phenylamino]-2-fluoro-phenyl}-5-methyl--5,6-dihydro-2H-[1,4]oxazin-3-ylamine, (S)-5-(5-(6-chloro-1-methyl-1H -indazol-3-ylamino)-2-fluorophenyl)-5-methyl--5,6dihydro-2H-1,4-oxazin-3-amine, and (S)-5[-5-(5-Chloro-indan-1-ylamino)-2-fluoro-phenyl]-5-methyl--5,6-dihydro-2H-[1,4]oxazin-3-ylamine, or a pharmaceutical acceptable salt thereof.

14. The compound of claim 1, selected from the group consisting of

[3-((R)-5-Amino-3-methyl-3,6-dihydro-2H-[1,4]oxazin-3-yl)-4-fluoro-phenyl]-(3-chloro-quinolin-8-yl)-amine,

[3-((R)-5-Amino-3-methyl-3,6-dihydro-2H-[1,4]oxazin-3-yl)-4-fiuoro-phenyl]-(3,6-dichloro-quinolin-8-yl)-amine,

[3-((R)-5-Amino-3-methyl-3,6-dihydro-2H-[1,4]oxazin-3-yl)-4-fluoro-phenyl]-(3-chloro-6-fluoro-quinolin-8-yl)-amine,

[3-((R)-5-Amino-3-methyl-3,6-dihydro-2H-[1,4]oxazin-3-yl)-4-fiuoro-phenyl]-(3-difluoromethoxy-quinolin-8-yl)-amine,

[3-((R)-5-Amino-3-methyl-3,6-dihydro-2H-[1,4]oxazin-3-yl)-4-fluoro-phenyl]-[3-(2-fluoro-ethoxy)-quinolin-8-yl]-amine,

[3-((R)-5-Amino-3-methyl-3,6-dihydro-2H-[1,4]oxazin-3-yl)-4-fluoro-phenyl]-(3cyclopropylmethoxy-6-fluoro-quinolin-8-yl)-amine,

[3-((R)-5-Amino-3-methyl-3,6-dihydro-2H-[1,4]oxazin-3-yl)-4-fluoro-phenyl]-[3-(2,2,2trifluoro-ethoxy)-quinolin-8-yl]-amine,

[3-((R)-5-Amino-3-methyl-3,6-dihydro-2H-[1,4]oxazin-3-yl)-4-fluoro-phenyl]-(3-chloro 6,7-dihydro-5H-[1]pyridin-7-yl)-amine, and

[3-(5-Amino-3-methyl-3,6-dihydro-2H-[1,4]oxazin-3-yl)-phenyl]-(1,2-dimethyl-1H benzoimidazol-5-yl)-amine, or a pharmaceutical acceptable salt thereof.

15. The compound of claim 1, selected from the group consisting of

[3-(5-Amino-3-methyl-3,6-dihydro-2H-[1,4]oxazin-3-yl)-phenyl]-(2-cyclopropyl-benzooxazol-4-yl)-amine,

[3-(5-Amino-3-methyl-3,6-dihydro-2H-[1,4]oxazin-3-yl)-phenyl]-(3-chloro-quinolin-8-yl)-amine,

[3-(5-Amino-3-methyl-3,6-dihydro-2H-[1,4]oxazin-3-yl)-phenyl]-(3-chloro-6-fluoro-quinolin-8-yl)-amine,

[3-(5-Amino-3-methyl-3,6-dihydro-2H-[1,4]oxazin-3-yl)-phenyl]-(3-methoxy-quinolin-8-yl)-amine,

[3-(5-Amino-3-methyl-3,6-dihydro-2H-[1,4]oxazin-3-yl)-phenyl]-quinolin-8-yl-amine, 5-[3-(2,4-Dichloro-benzylamino)-phenyl]-5-methyl--5,6-dihydro-2H-[1,4]oxazin-3-ylamine, 5-[3-(2-Difluoromethoxy-phenylamino)-phenyl]-5-methyl--5,6-dihydro-2H-[1,4]oxazin-3-ylamine, 5-[3-(4-Chloro-benzylamino)-phenyl]-5-methyl-5,6-dihydro-2H-[1,4]oxazin-3-ylamine, 5-[3-(5-Chloro-indan-1-ylamino)-phenyl]-5-methyl-5,6-dihydro-2H-[1,4]oxazin-3-ylamine, and 5-{3-[1-(4-Chloro-phenyl)-ethylamino]-phenyl}-5-methyl-5,6-dihydro-2H-[1,4]oxazin-3-ylamine, or a pharmaceutical acceptable salt thereof.

16. The compound of claim 1, selected from the group consisting of (R)-5-(5-(cyclopentylamino)-2-fluorophenyl)-5-methyl-5,6-dihydro-2H-1,4-oxazin-3-amine, (R)-5-(5-((4-chloro-1-(difluoromethyl)-1H-pyrazol-3-yl)methylamino)-2-fluorophenyl-5-methyl-5,6-dihydro-2H-1,4-oxazin-3-amine hydrochloride, (R)-5-{5[2-(2,2-Difluoro-ethoxy)-phenylamino]-2-fluoro-phenyl}-5-methyl-5,6-dihydro-2H-[1,4]oxazin-3-ylamine hydrochloride, (S)-5-[5-(5-Chloro-indan-1-ylamino)-2-fluoro-phenyl]-5-methyl--5,6-dihydro-2H-[1,4]oxazin-3-ylamine hydrochloride,

[3-((R)-5-Amino-3-methyl-3,6-dihydro-2H-[1,4]oxazin-3-yl)-4-fluoro-phenyl]-(3-chloro-quinolin-8-yl)-amine hydrochloride,

[3-((R)-5-Amino-3-methyl-3,6-dihydro-2H-[1,4]oxazin-3-yl)-4-fluoro-phenyl]-(3-chloro-6-fluoro-quinolin-8-yl)-amine hydrochloride,

[3-(5-Amino-3-methyl-3,6-dihydro-2H-[1,4]oxazin-3-yl)-phenyl]-(3-chloro-quinolin-8-yl)-amine hydrochloride,

[3-(5-Amino-3-methyl-3,6-dihydro-2H-[1,4]oxazin-3-yl)-phenyl]-(3-methoxy-quinolin-8-yl)-amine hydrochloride, and 5-[3-(5-Chloro-indan-1-ylamino)-phenyl]-5-methyl-5,6-dihydro-2H-[1,4]oxazin-3-ylamine, or a pharmaceutical acceptable salt thereof.

17. A pharmaceutical composition comprising a therapeutically effective amount of a compound of formula I

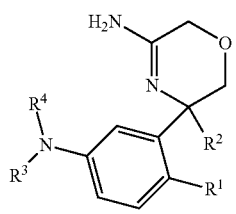

wherein $R^1$ is selected from the group consisting of
iv) hydrogen,
v) halogen, and
vi) $C_{1-6}$-alkyl;

$R^2$ is $C_{1-6}$-alkyl;

$R^3$ is selected from the group consisting of xix) aryl, xx) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl, xxi) aryl-$C_{1-6}$-alkyl, xxii) aryl-$C_{1-6}$-alkyl, wherein the aryl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl, xxiii) heteroaryl, xxiv) heteroaryl substituted by 1-4 substituents individually selected from amido, cyano, cyano-$C_{1-6}$-alkyl, $C_{3-7}$-cycloalkyl, $C_{3-7}$-cycloalkyl-$C_{2-6}$-alkenyl, $C_{3-7}$-cycloalkyl-$C_{2-6}$-alkynyl, $C_{3-7}$-cycloalkyl-$C_{1-6}$-alkyl, $C_{3-7}$-cycloalkyl-$C_{1-6}$-alkoxy, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl, $C_{1-6}$-alkyl and nitro, xxv) heteroaryl-$C_{1-6}$-alkyl, xxvi) heteroaryl-$C_{1-6}$-alkyl, wherein the heteroaryl is substituted by 1-4 substituents individually selected from amido, cyano, cyano-$C_{1-6}$-alkyl, $C_{3-7}$-cycloalkyl, $C_{3-7}$-cycloalkyl-$C_{2-6}$-alkenyl, $C_{3-7}$-cycloalkyl-$C_{2-6}$-alkynyl, $C_{3-7}$-cycloalkyl-$C_{1-6}$-alkyl, $C_{3-7}$-cycloalkyl-$C_{1-6}$-alkoxy, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl, $C_{1-6}$-alkyl and nitro, xxvii) $C_{1-6}$-alkyl, xxviii) $C_{1-6}$-alkyl substituted by 1-5 substituents individually selected from cyano, halogen, ydroxyl, $C_{1-6}$-alkyl-S— and $C_{1-6}$-alkoxy, xxix) $C_{3-7}$-cycloalkyl, xxx) $C_{3-7}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, ydroxyl, $C_{1-6}$-alkoxy, $C_{1-6}$-alkoxy-$C_{1-6}$-alkyl and $C_{1-6}$-alkyl, xxxi) $C_{3-7}$-cycloalkyl-$C_{1-6}$-alkyl, xxxii) $C_{3-7}$-cycloalkyl-$C_{1-6}$-alkyl, wherein the $C_{3-7}$-cycloalkyl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl, xxxiii) heterocyclyl, xxxiv) heterocyclyl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl, xxxv) heterocyclyl-$C_{1-6}$-alkyl, and xxxvi) heterocyclyl-$C_{1-6}$-alkyl, wherein the heterocyclyl is substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl; and $R^4$ is hydrogen;

or a pharmaceutically acceptable salt thereof and a pharmaceutically acceptable carrier and/or a pharmaceutically acceptable auxiliary substance.

* * * * *